(12) United States Patent
Cowan et al.

(10) Patent No.: US 10,046,106 B2
(45) Date of Patent: Aug. 14, 2018

(54) BLADDER SYRINGE FLUID DELIVERY SYSTEM

(75) Inventors: Kevin P. Cowan, Allison Park, PA (US); Raymond C. Hoffman, Gibsonia, PA (US); Arthur E. Uber, III, Pittsburgh, PA (US); Bernard J. Hobi, Apollo, PA (US); Vincent S. Rossitto, Apollo, PA (US); Jaroslaw Wlodarczyk, Lower Burrell, PA (US); Matthew Schrauder, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 989 days.

(21) Appl. No.: 13/881,072

(22) PCT Filed: Oct. 25, 2011

(86) PCT No.: PCT/US2011/057701
§ 371 (c)(1),
(2), (4) Date: Apr. 23, 2013

(87) PCT Pub. No.: WO2012/061140
PCT Pub. Date: May 10, 2012

(65) Prior Publication Data
US 2013/0211248 A1 Aug. 15, 2013

Related U.S. Application Data

(60) Provisional application No. 61/406,453, filed on Oct. 25, 2010.

(51) Int. Cl.
*A61M 37/00* (2006.01)
*A61M 5/00* (2006.01)
(Continued)

(52) U.S. Cl.
CPC ............ *A61M 5/007* (2013.01); *A61M 5/148* (2013.01); *A61M 5/1452* (2013.01); *A61M 5/2425* (2013.01); *A61M 5/31511* (2013.01)

(58) Field of Classification Search
CPC .... A61M 5/007; A61M 5/1452; A61M 5/148; A61M 5/31511; A61M 5/2425; A61M 2005/3128; A61M 5/31513
(Continued)

(56) References Cited

U.S. PATENT DOCUMENTS

| 798,093 A | 8/1905 | Dean |
|---|---|---|
| 817,054 A | 4/1906 | Gay |

(Continued)

FOREIGN PATENT DOCUMENTS

| CN | 1323229 A | 11/2001 |
|---|---|---|
| CN | 1665562 A | 9/2005 |

(Continued)

OTHER PUBLICATIONS

International Search Report for Counterpart PCT Application No. PCT/US1999/027574.
(Continued)

*Primary Examiner* — Edelmira Bosques
(74) *Attorney, Agent, or Firm* — Joseph L. Kent; David Schramm; James R. Stevenson

(57) ABSTRACT

A bladder syringe for a fluid delivery system includes a cylindrical body, a cap-bladder assembly, a plunger element disposed in the cylindrical body, and a mounting assembly to secure the cap-bladder assembly to the cylindrical body. The cylindrical body has a distal end and a proximal end and defines a throughbore. The cap-bladder assembly is adapted for connection to the distal end of the cylindrical body, and includes a cap body and a bladder. The cap body defines an interior cavity and a distal discharge conduit and is adapted
(Continued)

to engage the distal end of the cylindrical body. A disc-shaped bladder is disposed within the interior cavity and typically includes a central membrane portion. The plunger element is disposed in the throughbore of the cylindrical body and is vented to enable evacuation of the space between the plunger element and the cap-bladder assembly in the cylindrical body.

41 Claims, 83 Drawing Sheets

(51) Int. Cl.
  *A61M 5/145* (2006.01)
  *A61M 5/148* (2006.01)
  *A61M 5/24* (2006.01)
  *A61M 5/315* (2006.01)
(58) Field of Classification Search
  USPC .......................................................... 604/131
  See application file for complete search history.

(56) References Cited

U.S. PATENT DOCUMENTS

| | | |
|---|---|---|
| 937,029 A | 10/1909 | Strong et al. |
| 1,388,946 A | 8/1921 | Goold |
| 2,514,575 A | 7/1950 | Hein |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,161,194 A | 12/1964 | Chapman |
| 3,161,195 A | 12/1964 | Taylor |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,301,293 A | 1/1967 | Santelli |
| 3,340,869 A | 9/1967 | Bane |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauh et al. |
| 3,507,278 A | 4/1970 | Werding |
| 3,527,215 A | 9/1970 | De Witt |
| 3,557,788 A | 1/1971 | Swartz |
| 3,613,963 A | 10/1971 | Berkmuller |
| 3,618,846 A | 11/1971 | Poli |
| 3,699,961 A | 10/1972 | Szpur |
| 3,785,367 A | 1/1974 | Fortin et al. |
| 3,826,409 A | 7/1974 | Chilcoate |
| 3,873,003 A | 3/1975 | Seiferth et al. |
| 3,938,514 A | 2/1976 | Boucher |
| 3,998,223 A | 12/1976 | Dawe |
| 4,006,736 A | 2/1977 | Kranys et al. |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,349,129 A | 9/1982 | Amneus |
| 4,411,656 A | 10/1983 | Cornett, III |
| 4,419,096 A | 12/1983 | Leeper et al. |
| 4,438,845 A | 3/1984 | Mochow |
| 4,444,310 A | 4/1984 | Odell |
| 4,526,296 A | 7/1985 | Berger et al. |
| 4,677,980 A | 7/1987 | Reilly et al. |
| 4,741,733 A | 5/1988 | Winchell et al. |
| 4,743,243 A | 5/1988 | Vaillancourt |
| 4,753,638 A | 6/1988 | Peters |
| 4,758,226 A | 7/1988 | Carre |
| 4,773,458 A | 9/1988 | Touzani |
| 4,850,807 A | 7/1989 | Frantz |
| 4,904,239 A | 2/1990 | Winchell et al. |
| 5,000,739 A | 3/1991 | Kulisz et al. |
| 5,011,477 A | 4/1991 | Winchell et al. |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,300,031 A | 4/1994 | Neer et al. |
| 5,312,018 A | 5/1994 | Evezich |
| 5,316,452 A | 5/1994 | Bogen et al. |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,378,233 A | 1/1995 | Haber et al. |
| 5,383,858 A | 1/1995 | Reilly et al. |
| 5,397,157 A | 3/1995 | Hempel et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,731,053 A | 3/1998 | Kuhn et al. |
| D394,212 S | 5/1998 | Mazda |
| 5,758,789 A | 6/1998 | Shin et al. |
| 5,779,675 A | 7/1998 | Reilly et al. |
| 5,785,691 A | 7/1998 | Vetter et al. |
| 5,794,107 A | 8/1998 | Russell |
| D397,930 S | 9/1998 | Mazda |
| D397,931 S | 9/1998 | Mazda |
| D397,932 S | 9/1998 | Mazda |
| D397,933 S | 9/1998 | Mazda |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |

(56) References Cited

U.S. PATENT DOCUMENTS

| | | | |
|---|---|---|---|
| 5,899,889 A | 5/1999 | Futagawa et al. | |
| 5,913,844 A | 6/1999 | Ziemba et al. | |
| RE36,377 E | 11/1999 | Gilbert | |
| 5,976,112 A | 11/1999 | Lyza, Jr. | |
| 5,979,326 A | 11/1999 | Ohinata | |
| 5,980,489 A | 11/1999 | Kriesel | |
| 6,050,957 A * | 4/2000 | Desch | A61B 5/15003 |
| | | | 600/579 |
| 6,056,724 A | 5/2000 | Lacroix | |
| 6,062,437 A | 5/2000 | Mascitelli | |
| 6,063,058 A | 5/2000 | Sakamoto | |
| 6,077,252 A | 6/2000 | Siegel | |
| 6,083,204 A | 7/2000 | Malerba et al. | |
| 6,105,815 A | 8/2000 | Mazda | |
| 6,139,530 A * | 10/2000 | Hiejima | A61M 5/14526 |
| | | | 604/140 |
| 6,142,976 A | 11/2000 | Kubo | |
| 6,216,915 B1 | 4/2001 | Harman et al. | |
| 6,250,505 B1 | 6/2001 | Petit | |
| 6,270,482 B1 | 8/2001 | Rosoff et al. | |
| 6,273,152 B1 | 8/2001 | Buehler et al. | |
| 6,315,761 B1 | 11/2001 | Shcherbina et al. | |
| 6,319,235 B1 | 11/2001 | Yoshino | |
| 6,322,542 B1 | 11/2001 | Nilson et al. | |
| 6,328,715 B1 | 12/2001 | Dragan et al. | |
| 6,332,876 B1 | 12/2001 | Poynter et al. | |
| 6,450,993 B1 | 9/2002 | Lin | |
| 6,465,024 B1 | 10/2002 | Di Scala et al. | |
| 6,485,471 B1 | 11/2002 | Zivitz et al. | |
| 6,494,824 B1 * | 12/2002 | Apple | A61N 5/1002 |
| | | | 600/3 |
| 6,497,684 B2 | 12/2002 | Witowski | |
| 6,544,246 B1 | 4/2003 | Niedospial, Jr. | |
| 6,558,358 B2 | 5/2003 | Rosoff | |
| 6,578,738 B1 | 6/2003 | Keller | |
| 6,620,134 B1 | 9/2003 | Trombley, III et al. | |
| 6,634,524 B1 | 10/2003 | Helmenstein | |
| 6,652,489 B2 | 11/2003 | Trocki et al. | |
| 6,702,143 B2 | 3/2004 | Wang | |
| 6,723,074 B1 | 4/2004 | Halseth | |
| 6,726,657 B1 | 4/2004 | Dedig et al. | |
| 6,773,417 B2 | 8/2004 | Fitzgibbons et al. | |
| 6,840,164 B2 | 1/2005 | Eastman | |
| 6,866,039 B1 | 3/2005 | Wright et al. | |
| 6,869,419 B2 | 3/2005 | Dragan et al. | |
| RE38,770 E | 8/2005 | Gilbert et al. | |
| 7,004,213 B2 | 2/2006 | Hansen | |
| 7,011,650 B2 | 3/2006 | Rosoff et al. | |
| 7,192,549 B2 | 3/2007 | Hansen | |
| 7,250,039 B2 | 7/2007 | Fitzgerald | |
| 7,309,463 B2 | 12/2007 | Hansen | |
| 7,419,478 B1 | 9/2008 | Reilly et al. | |
| 7,497,843 B1 | 3/2009 | Castillo et al. | |
| 7,513,378 B2 | 4/2009 | Mori et al. | |
| 7,597,683 B2 | 10/2009 | Myhrberg et al. | |
| 7,621,395 B2 | 11/2009 | Mogensen et al. | |
| 7,666,169 B2 | 2/2010 | Cowan et al. | |
| 7,686,788 B2 | 3/2010 | Freyman et al. | |
| 7,740,792 B2 | 6/2010 | Haury et al. | |
| 7,802,691 B2 | 9/2010 | Musalek et al. | |
| 8,133,203 B2 | 3/2012 | Hack | |
| 8,992,482 B2 * | 3/2015 | Fojtik | A61M 5/204 |
| | | | 604/187 |
| 2001/0018575 A1 | 8/2001 | Lyza, Jr. | |
| 2002/0091361 A1 | 7/2002 | Rosoff et al. | |
| 2003/0210985 A1 | 11/2003 | Feygin et al. | |
| 2003/0216695 A1 | 11/2003 | Yang | |
| 2004/0068224 A1 | 4/2004 | Couvillon, Jr. et al. | |
| 2007/0167910 A1 | 7/2007 | Tennican et al. | |
| 2008/0091147 A1 * | 4/2008 | Lee | A61M 5/165 |
| | | | 604/190 |
| 2009/0218243 A1 | 9/2009 | Gym et al. | |
| 2010/0234812 A1 | 9/2010 | Parker et al. | |
| 2011/0101035 A1 | 5/2011 | Beebe | |
| 2011/0218499 A1 | 9/2011 | Cahen | |
| 2013/0163364 A1 | 6/2013 | Park | |

FOREIGN PATENT DOCUMENTS

| | | |
|---|---|---|
| DE | 29818399 | 2/2000 |
| EP | 1086661 A2 | 3/2001 |
| FR | 1288915 A | 3/1962 |
| FR | 2350109 | 12/1977 |
| GB | 2214819 A | 9/1989 |
| WO | 199820920 | 5/1998 |
| WO | 1999024098 A1 | 5/1999 |
| WO | 01/17590 | 3/2001 |
| WO | 2008002483 A2 | 1/2008 |
| WO | 2013163364 | 10/2013 |

OTHER PUBLICATIONS

The Supplementary European Search Report dated Apr. 20, 2015 from corresponding EP Application No. 13780936.4.
Written Opinion for counterpart PCT Application No. PCT/US2011/57701.
International Search Report from U.S. International Searching Authority dated Jul. 8, 2013 concerning International Patent Application No. PCT/US2013/037763 filed Apr. 23, 2013, 4 pages.
Written Opinion from U.S. International Searching Authority dated Aug. 7, 2013 concerning International Patent Application No. PCT/US2013/037763 filed Apr. 23, 2013, 10 pages.
The International Preliminary Report on Patentability of PCT Application No. PCT/US2013/034896.
International Preliminary Report on Patentability from corresponding PCT Application No. PCT/US2013/037763.
International Search Report for counterpart PCT Application No. PCT/US2011/57701 dated Feb. 13, 2012.
"Extended European Search Report dated Mar. 14, 2016 from EP13778257", dated Mar. 14, 2016.
International Preliminary Report on Patentability from corresponding PCT Application No. PCT/US2013/035884, dated Jun. 11, 2013.
International Search Report and Written Opinion of the International Searching Authority in counterpart PCT Application No. PCT/US/2013/035884 dated Jun. 28, 2013.
International Preliminary Report on Patentability, International Search Report, and Written Opinion from related PCT Application No. PCT/US2013/035884.

\* cited by examiner

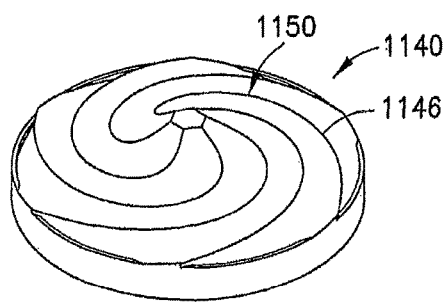
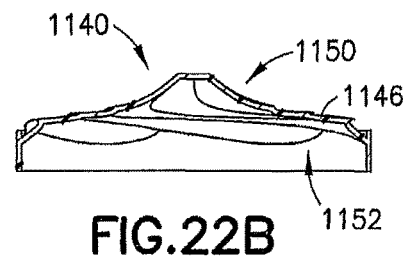
FIG.22A
FIG.22B
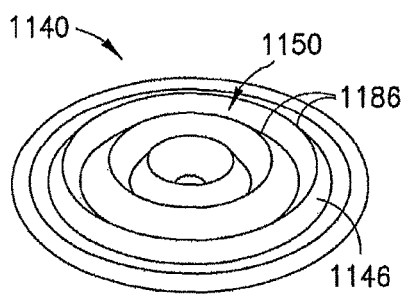
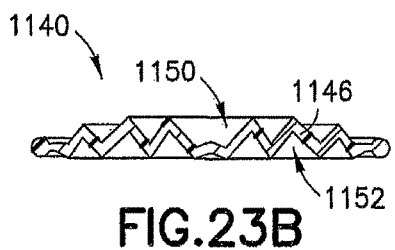
FIG.23A
FIG.23B
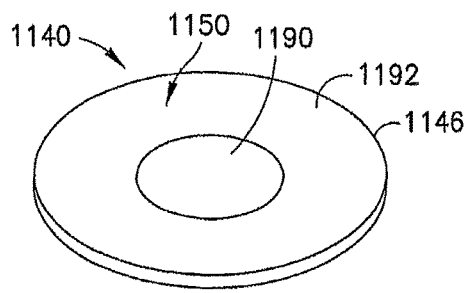
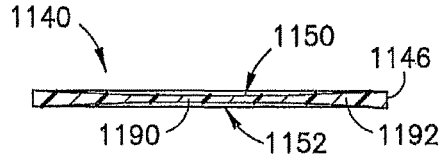
FIG.24A
FIG.24B

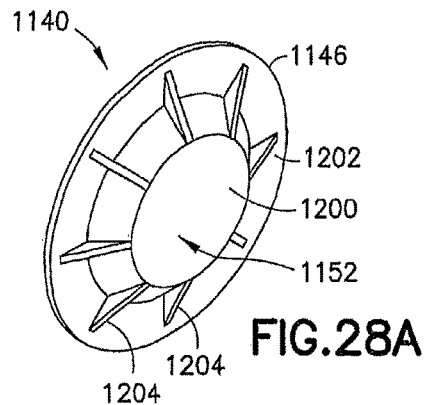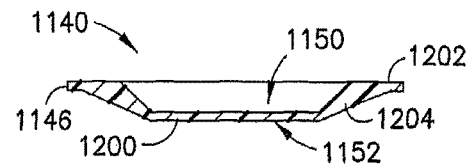
FIG.28A  FIG.28B
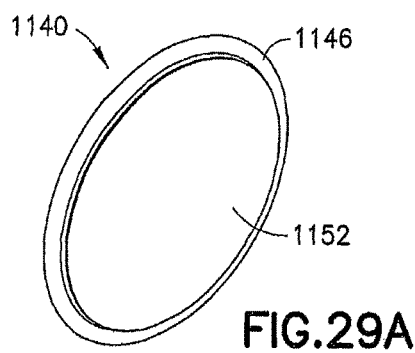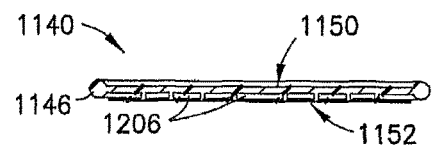
FIG.29A  FIG.29B
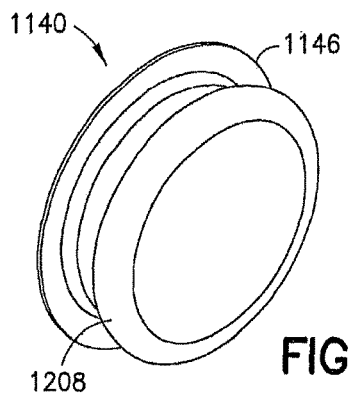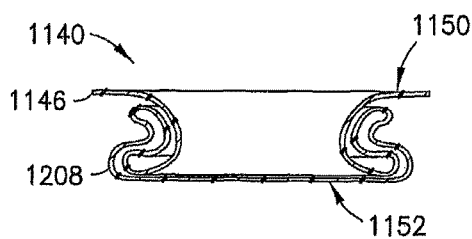
FIG.30A  FIG.30B

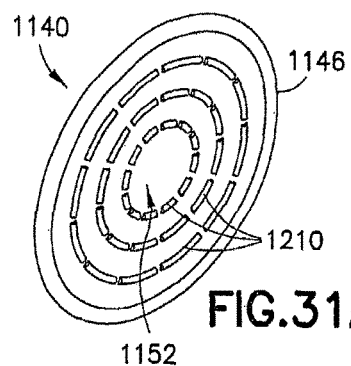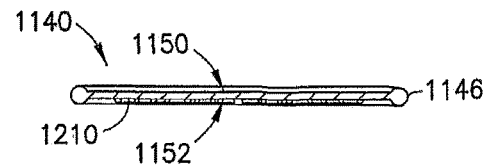
FIG.31A FIG.31B
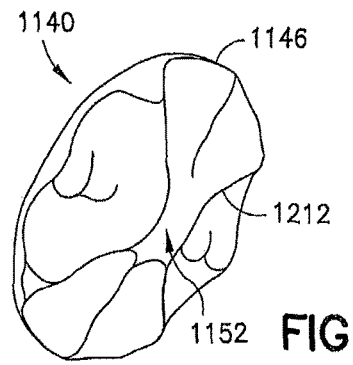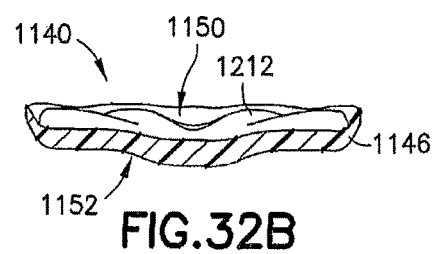
FIG.32A FIG.32B
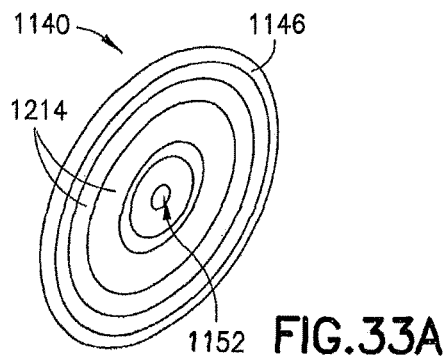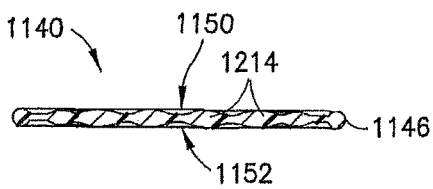
FIG.33A FIG.33B

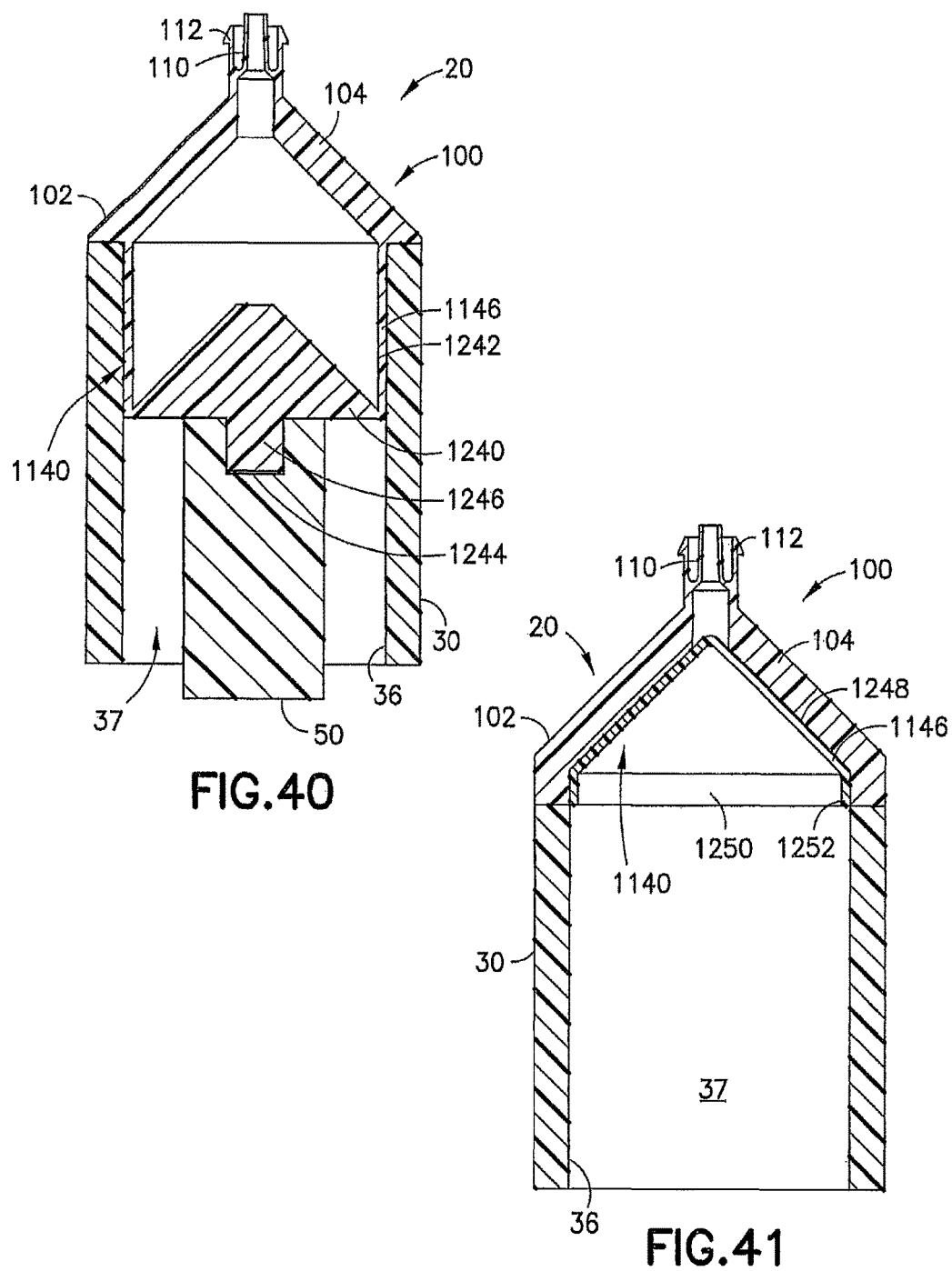

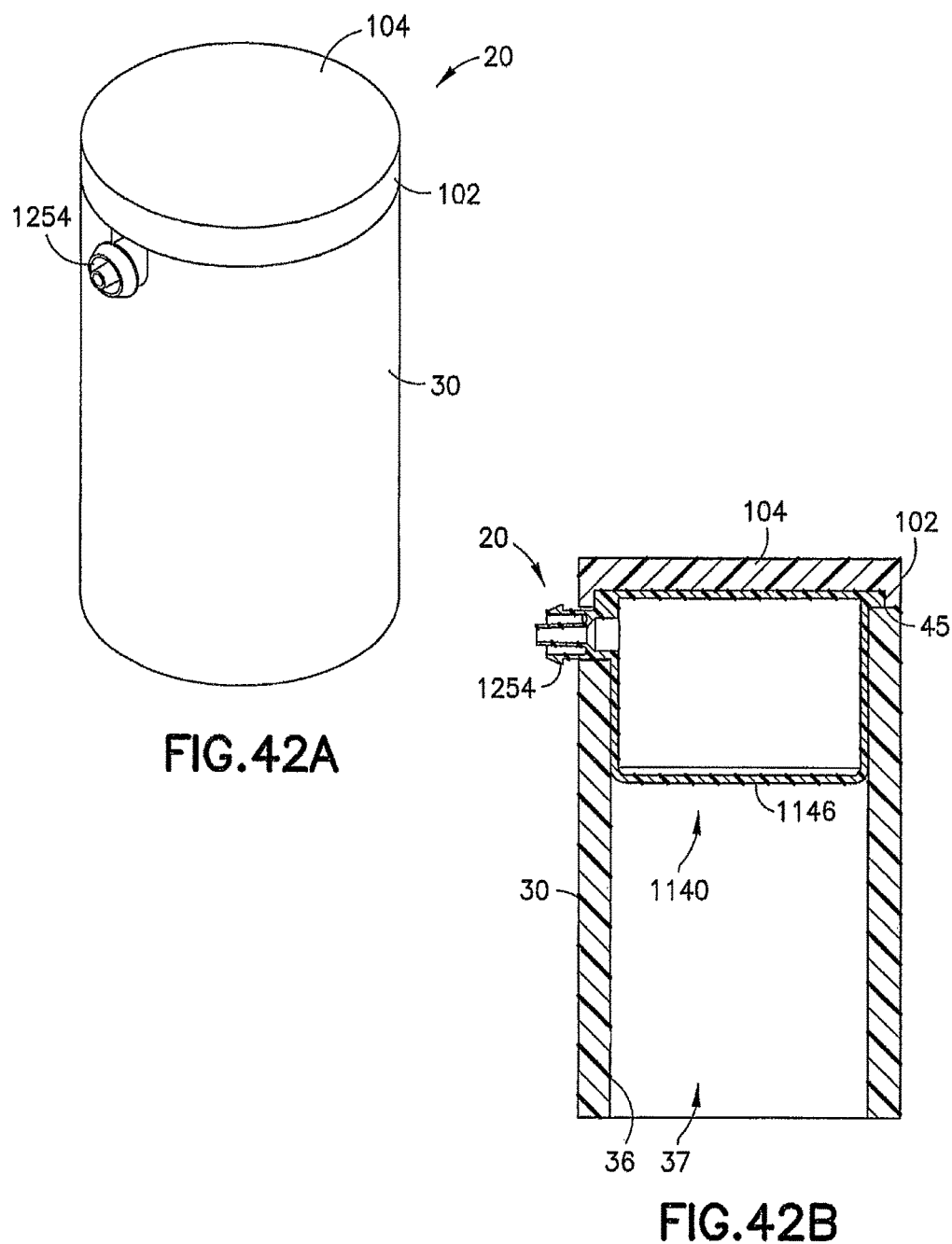

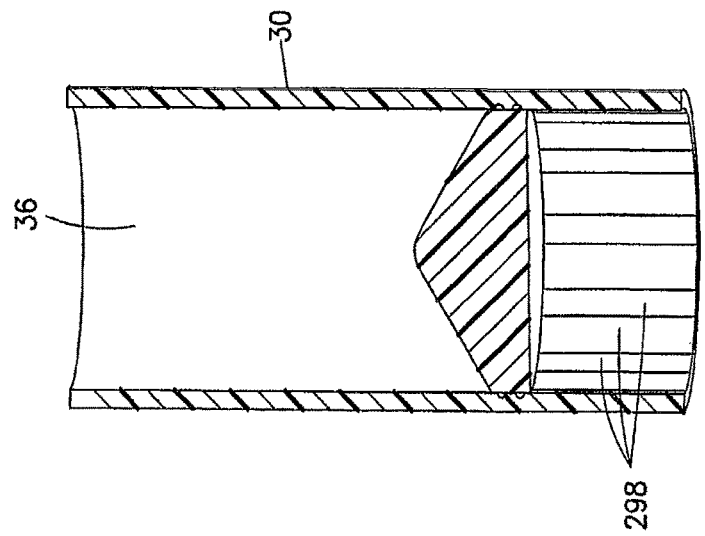
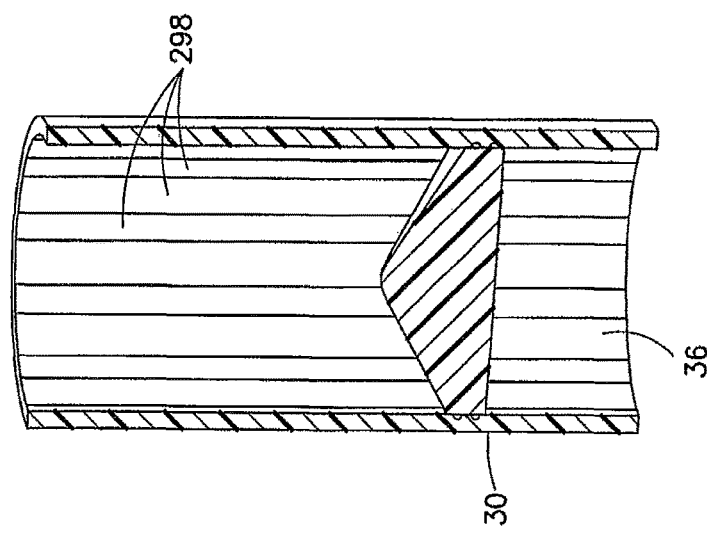
FIG.62B
FIG.62A

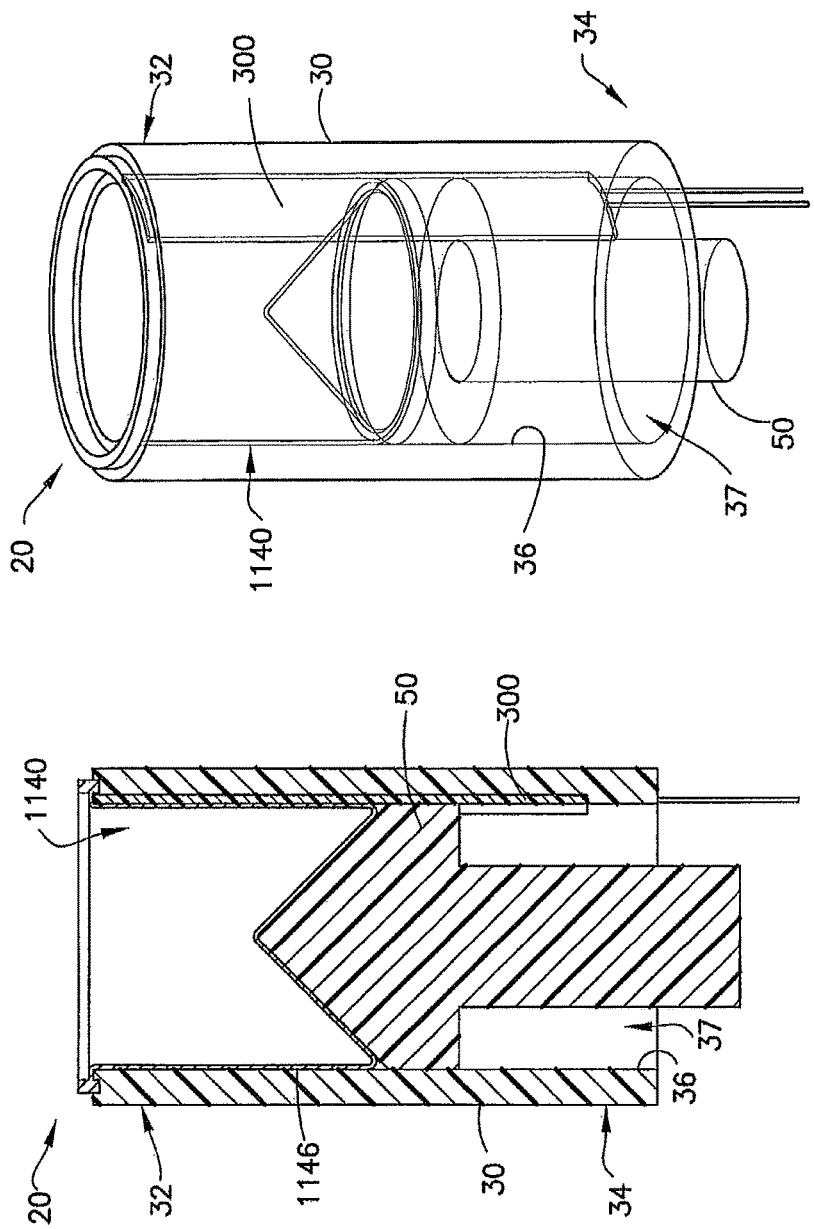

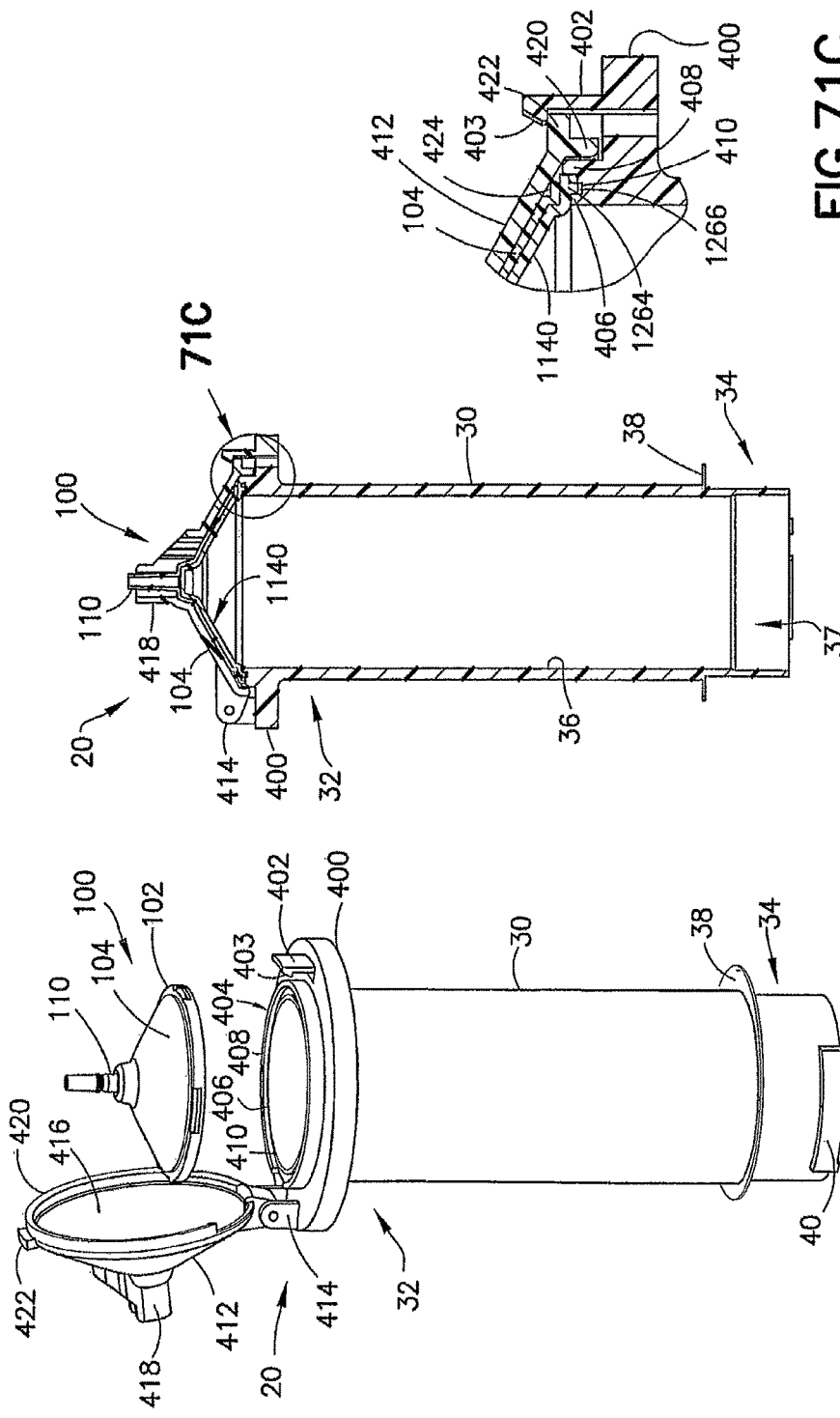

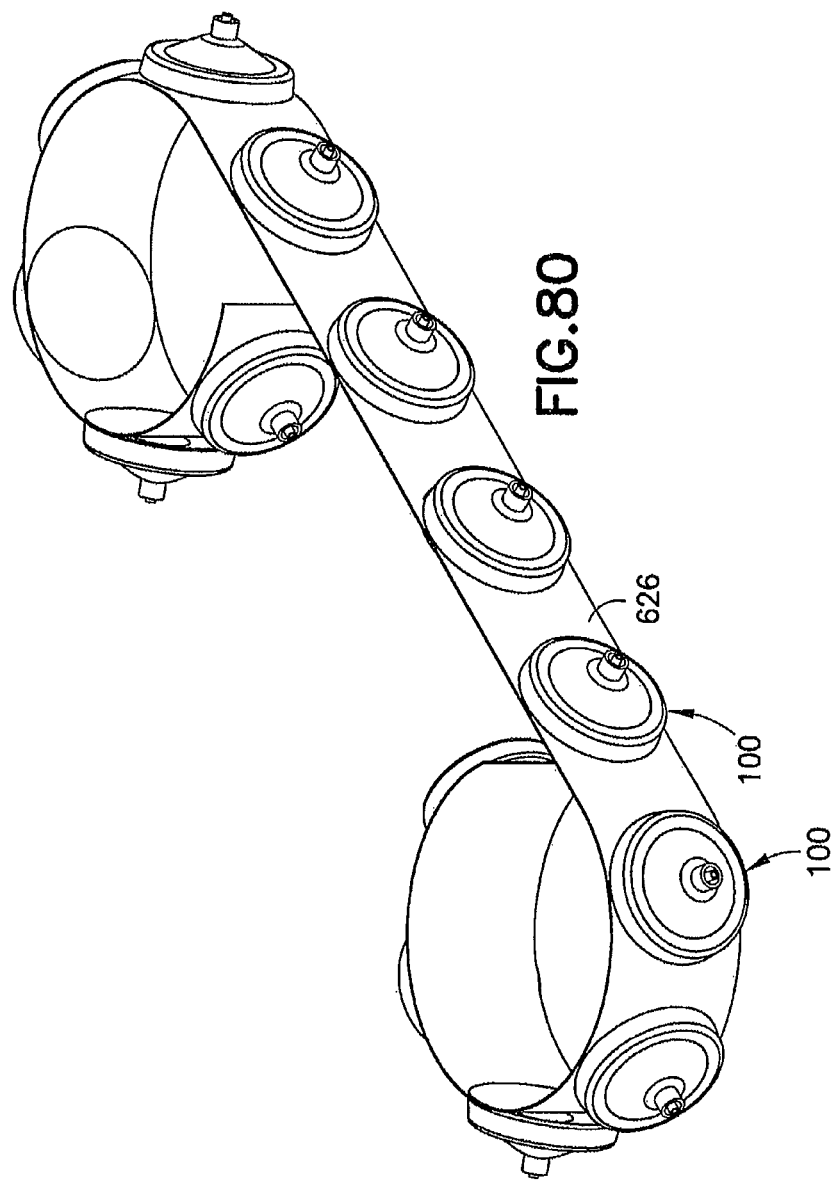

BLADDER SYRINGE FLUID DELIVERY SYSTEM

BACKGROUND OF THE INVENTION

Field of the Invention

The present invention is related to the medical field and, more particularly, disposable syringes used in the medical field in which all or part of the syringe may be disposed of after a single use.

Description of Related Art

It is well known that syringes used in the medical field are typically disposable and are discarded after one use. These syringes usually comprise a barrel and a plunger mounted for reciprocal movement in the barrel, both parts usually being made of plastic material. Although disposable syringes are typically made by mass production methods such as injection molding, such disposable syringes are relatively expensive due to the materials and precision involved in their manufacture.

In order to reduce manufacturing costs, it has been proposed to combine a reusable syringe barrel and plunger with a replaceable container positioned either at the discharge end of the syringe barrel or within the syringe barrel. The container is typically flexible and acted upon by the action of the plunger to fill and dispense fluid from the container. For example, the container may be introverted or collapsed upon itself by action of the plunger to eject or administer a medicinal fluid contained in the container. An example of a syringe of this type is disclosed in U.S. Pat. Nos. 4,236,516 and 4,325,369 to Nilson. In the syringe disclosed in the foregoing patents, the container forms the end wall of the syringe barrel and comprises a substantially rigid first wall portion at the exterior side of the end wall and a flexible second wall portion at the interior side of the end wall. The container is introvertible upon the inside surface of the first wall portion. A nozzle is provided on the first wall portion for attachment of a hypodermic needle. In the Nilson syringe, as described in the foregoing patents, the container is formed as a spherical bulb having substantially the same diameter as the cylinder space formed by the syringe barrel. When an empty container is attached to the syringe barrel, the flexible second wall portion is introverted upon the inside surface of the first wall portion. To fill the container, the piston is withdrawn and the flexible wall portion is carried along by the piston due to sub-atmospheric pressure created between the piston and the flexible wall portion, while liquid such as blood or a medicinal fluid is pulled into the container. However, a substantial sub-atmospheric pressure (vacuum) is created by the piston during the latter part of the withdrawal stroke thereof, which requires considerable force to be applied to the piston at the end of the withdrawal stroke necessary for filling the container. Under certain circumstances, the container may not be completely filled.

U.S. Pat. No. 4,312,344 to Nilson seeks to overcome the foregoing deficiencies of the earlier Nilson syringes by providing a rigid spherical container that attaches to the end of the syringe barrel and has a collapsible spherical bulb attached thereto. This improved Nilson syringe further includes a plunger guided for axial movement in the syringe barrel, and a resilient plunger head connected to the plunger. The plunger has a diameter less than the diameter of the container but can be deformed to engage the spherical bulb when introverted upon the inside surface of the spherical container over substantially the entire surface thereof. The rigid spherical container attached to the end of the syringe barrel and the resilient plunger head on the plunger address some of the operational difficulties with the earlier Nilson syringes.

Other container-type syringes are known in the medical field which incorporate a bulb portion or bladder element such as may be found in U.S. Pat. No. 798,093 to Dean; U.S. Pat. No. 3,527,215 to De Witt; and U.S. Pat. No. 6,450,993 to Lin. The Dean patent discloses a syringe having a collapsible bulb portion secured to a glass container via a clamp. The bulb portion is in the form of a diaphragm/bladder that is secured to a cap portion. The De Witt patent discloses a bladder held within a cavity in a needle hub by a retaining ring. The Lin patent discloses a half-disposable syringe barrel including a reusable barrel syringe and a disposable cap member.

Moreover, syringes are known in the medical field that incorporate a collapsible container or bag that is breach-loaded into a syringe barrel and then acted upon by a syringe plunger inserted into the syringe barrel to expel the contents of the container. U.S. Pat. No. 2,690,179 to Fox and U.S. Pat. No. 3,166,070 to Everett disclose such container/bag-type syringes. The Everett patent discloses a dispensing syringe that includes a syringe casing, collapsible bag, and a plunger with a venting check valve in a passage in the plunger. The Fox patent discloses a collapsible container housed within a syringe housing and actuated by a plunger. The plunger includes an air passage in which a check valve is present to vent air from a forward side of the plunger head. The container is a sealed bag situated within a head portion of the housing and carries a needle assembly. Such container/bag syringes are also used in the blood collection area such as disclosed by U.S. Pat. No. 3,785,367 to Fortin et al. The Fortin patent discloses a rubber cup-shaped member that fits inside a rigid housing attached to a syringe barrel. The rigid housing includes a hollow tapered adapter supporting an arterial needle for collecting an arterial blood sample from a patient which enters a container provided within the syringe barrel under arterial blood pressure. The syringe barrel includes a reciprocal syringe plunger therein.

SUMMARY OF THE INVENTION

As described in detail herein, one embodiment of a bladder syringe for a fluid delivery system comprises a cylindrical body, cap-bladder assembly, and a plunger element disposed in the cylindrical body. The cylindrical body has a distal end and a proximal end and defines a throughbore. The cylindrical body has an exterior mounting collar at the distal end of the cylindrical body. The cap-bladder assembly is adapted for connection to the distal end of the cylindrical body. The cap-bladder assembly comprises a cap, a bladder, and a retainer ring to secure the bladder in the cap. The cap body defines an interior cavity, a distal discharge conduit, and a proximal portion to receive the distal end of the cylindrical body. The proximal portion may have an end adapted to engage the mounting collar on the cylindrical body. The bladder is typically disc-shaped and disposed within the interior cavity and comprises an outer circumferential rib and a central membrane portion. The plunger element is disposed in the throughbore of the cylindrical body.

The central membrane portion of the bladder may have a non-uniform cross-section. In one variation, the central membrane portion may have a convoluted central well portion, a plurality of annular ribs, and/or a plurality of radial ribs, or any combination of the foregoing.

The plunger element may comprise a distal portion facing the cap-bladder assembly and a proximal portion adapted for connection with a piston element of a power fluid injector. The plunger element may further comprise a fluid path allowing gas to pass through the plunger element, and the plunger element may have a one-way check valve in the fluid path to allow gas to pass through the plunger element and exit at the proximal portion of the plunger element. The plunger element may further comprise a seal ring about the proximal portion providing a substantially fluid tight seal between the plunger element and cylindrical body and an optional guide ring about the distal portion. An inlet to the fluid path may be disposed between the guide ring and the seal ring.

In another embodiment, the bladder syringe for a fluid delivery system includes a cylindrical body, cap-bladder assembly, a plunger element disposed in the cylindrical body, and a mounting ring to secure the cap-bladder assembly to the cylindrical body. The cylindrical body has a distal end and a proximal end and defines a throughbore. The cap-bladder assembly is adapted for connection to the distal end of the cylindrical body and includes a cap body, a bladder, and a retainer ring. The cap body defines an interior cavity, a distal discharge conduit, and a proximal portion to receive the distal end of the cylindrical body. A bladder is disposed within the interior cavity and is typically disc-shaped and includes an outer circumferential rib and a central membrane portion. The retainer ring is used to secure the bladder in the interior cavity of the cap body. The plunger element is disposed in the throughbore of the cylindrical body, and the mounting ring secures the cap-bladder assembly to the distal end of the cylindrical body.

In another embodiment, the central membrane portion of the bladder may have a non-uniform cross-section. In one variation, the central membrane portion may have a convoluted central well portion, a plurality of annular ribs, and/or a plurality of radial ribs, or any combination of the foregoing.

In another embodiment, the plunger element may comprise a distal portion facing the cap-bladder assembly and a proximal portion adapted for connection with a piston element of a power fluid injector. The plunger element may further comprise a fluid path allowing gas to pass through the plunger element, and the plunger element may have a one-way check valve in the fluid path to allow gas to pass through the plunger element and exit at the proximal portion of the plunger element. The plunger element may further comprise a seal ring about the proximal portion providing a substantially fluid tight seal between the plunger element and cylindrical body and an optional guide ring about the distal portion. An inlet to the fluid path may be disposed between the guide ring and the seal ring.

Further, in another embodiment, the proximal portion of the cap body may comprise an exterior structure for engaging a corresponding engaging structure formed interiorly within the mounting ring to secure the cap-bladder assembly to the distal end of the cylindrical body. The exterior structure on the proximal portion of the cap body and the corresponding interior engaging structure within the mounting ring may comprise interengaging threads.

In another embodiment, a cap-bladder assembly is provided for connection to a cylindrical body. The cap-bladder assembly comprises a cap, a bladder, and a retainer ring. The cap includes a cap body defining an interior cavity, a distal discharge conduit, and a proximal portion to receive an end of the cylindrical body. The bladder is typically disc-shaped and disposed within the interior cavity and comprises an outer circumferential rib and a central membrane portion. The retainer ring is used to secure the bladder in the interior cavity of the cap body. The proximal portion is generally cylindrical-shaped and a conical portion connects the proximal portion to the discharge conduit. The proximal portion may have an exterior mounting. The central membrane portion of the bladder may have a non-uniform cross-section. In one variation, the central membrane portion may have a convoluted central well portion, a plurality of annular ribs, and/or a plurality of radial ribs, or any combination of the foregoing.

In another embodiment, a bladder syringe and a fluid delivery system incorporating the bladder syringe are provided. The power fluid injector comprises an injector housing and a reciprocally operable piston element. The bladder syringe comprises a cylindrical body having a distal end and a proximal end and defines a throughbore. A cap-bladder assembly is adapted for connection to the distal end of the cylindrical body and comprises a cap comprising a cap body defining an interior cavity and having a distal discharge conduit. The cap body is seated on the distal end of the cylindrical body. A disc-shaped bladder is disposed within the interior cavity and comprises a membrane portion. A plunger element is disposed in the throughbore of the cylindrical body and comprises a distal portion facing the cap-bladder assembly and a proximal portion adapted for connection with the piston element of the power fluid injector.

A retainer ring may be used to secure the bladder in the interior cavity of the cap body. The membrane portion may have extra material in a central area of the membrane portion. The membrane portion may define a convoluted central well portion. The membrane portion may be substantially planar. The membrane portion may comprise a plurality of annular ribs or rings. The membrane portion may comprise a plurality of radial ribs. The membrane portion may have extra material in a central area of the membrane portion and define a convoluted central well portion. The membrane portion may comprise a series of concentric angular-shaped convolutes. The membrane portion may have a thinner center section and a thicker outer section tapering from the thinner center section. The membrane portion may comprise a series of thicker wall sections near the center of the bladder. The thicker wall sections may be stepped. The membrane portion may have a non-uniform cross-section. The membrane portion may define a central well portion connected to an outer rim by a series of frangible webs. The membrane portion may be comprised of two or more materials. The membrane portion may have over-molded ribs on the bottom side thereof. The plunger element may comprise a distal portion facing the cap-bladder assembly and a proximal portion adapted for connection with a piston element of a power fluid injector. The plunger element may comprise a vent path allowing gas to pass through the plunger element to vent the space in the cylindrical body between the cap-bladder assembly and the plunger element, and the plunger element may have a one-way check valve in the vent path to allow gas to pass through the plunger element. An inlet to the vent path is desirably located at a circumferential outer surface of the plunger element.

The plunger element may comprise a seal ring providing a substantially fluid tight seal between the plunger element and the cylindrical body.

The plunger element may comprise one of an optical, ultrasonic, or mechanical sensor to detect the presence of the cap-bladder assembly on the distal end of the cylindrical body.

The distal portion of the plunger element and the membrane portion of the bladder may be shaped to interact to maintain the bladder material aligned in the cylindrical body during expansion of the bladder. The membrane portion may define a convoluted central well portion, and the distal portion of the plunger element may define a distal circular recess to interact with the convoluted central well portion. The membrane portion may define a series or plurality of concentric stepped or ridged portions adapted to cooperate with corresponding concentric stepped or ridged portions on the surface of the distal portion of the plunger element. An optical, ultrasonic, or mechanical sensor may be used to detect the presence of the cap-bladder assembly on the distal end of the cylindrical body.

In another embodiment, a bladder syringe is provided for a fluid delivery system and comprises a cylindrical body having a distal end and a proximal end and defining a throughbore, and a cap-bladder assembly adapted for connection to the distal end of the cylindrical body. The cap-bladder assembly comprises a cap comprising a cap body defining an interior cavity and a distal discharge conduit. The cap body is seated on the distal end of the cylindrical body. A disc-shaped bladder is disposed within the interior cavity and comprises a membrane portion. A plunger element is disposed in the throughbore of the cylindrical body. A connecting assembly is used to secure the cap-bladder assembly to the cylindrical body. The connecting assembly may comprise an inner sleeve fixed to the distal end of the cylindrical body and comprises a plurality of flex legs. The connecting assembly may further comprise an outer sleeve coaxially disposed about the inner sleeve and rotationally engaged with the inner sleeve such that rotation of the outer sleeve in one direction causes the flex legs to engage the cap body and secure the cap-bladder assembly on the distal end of the cylindrical body and rotation in an opposite direction releases the engagement. A distal end of the outer sleeve may be internally curved to engage the flex legs. The flex legs may terminate in a curved distal end to engage the internally curved distal end of the outer sleeve. The outer sleeve may be in threaded engagement with the inner sleeve. The flex legs may terminate in a curved distal end that engages a circumferential rim on the cap body when the flex legs engage the cap body.

Further details and advantages will be understood upon reading the following detailed description in conjunction with the accompanying drawings, wherein like parts are designated with like reference numerals throughout the several views.

BRIEF DESCRIPTION OF THE DRAWINGS

FIGS. 22A-22B are respective perspective and cross-sectional views of a tenth embodiment of the bladder for the cap-bladder assembly for the bladder syringe of FIGS. 1A-1B.

FIGS. 23A-23B are respective perspective and cross-sectional views of an eleventh embodiment of the bladder for the cap-bladder assembly for the bladder syringe of FIGS. 1A-1B.

FIGS. 24A-24B are respective perspective and cross-sectional views of a twelfth embodiment of the bladder for the cap-bladder assembly for the bladder syringe of FIGS. 1A-1B.

FIGS. 28A-28B are respective perspective and cross-sectional views of a sixteenth embodiment of the bladder for the cap-bladder assembly for the bladder syringe of FIGS. 1A-1B.

FIGS. 29A-29B are respective perspective and cross-sectional views of a seventeenth embodiment of the bladder for the cap-bladder assembly for the bladder syringe of FIGS. 1A-1B.

FIGS. 30A-30B are respective perspective and cross-sectional views of an eighteenth embodiment of the bladder for the cap-bladder assembly for the bladder syringe of FIGS. 1A-1B.

FIGS. 31A-31B are respective perspective and cross-sectional views of a nineteenth embodiment of the bladder for the cap-bladder assembly for the bladder syringe of FIGS. 1A-1B.

FIGS. 32A-32B are respective perspective and cross-sectional views of a twentieth embodiment of the bladder for the cap-bladder assembly for the bladder syringe of FIGS. 1A-1B.

FIGS. 33A-33B are respective perspective and cross-sectional views of a twenty-first embodiment of the bladder for the cap-bladder assembly for the bladder syringe of FIGS. 1A-1B.

FIG. 40 is a schematic cross-sectional view of the bladder syringe of FIGS. 1A-1B in which the bladder is mechanically operated by the plunger element.

FIG. 41 is a schematic cross-sectional view of the bladder syringe of FIGS. 1A-1B in which the bladder has a tapered profile to match the interior of a cap of the cap-bladder assembly.

FIGS. 42A-42B are respective perspective and schematic cross-sectional views of another embodiment of the bladder syringe in which the bladder is in the form of a flexible body that fits within the inner diameter of the cylindrical body of the bladder syringe, and the cap of the cap-bladder assembly is a solid planar end cap.

FIGS. 62A-62B are respective schematic cross-sectional views of another embodiment of the bladder syringe in which the interior wall of the cylindrical body of the bladder syringe and/or the interior of the cap in the cap-bladder assembly has surface texturing that becomes visually clear when exposed to liquid.

FIGS. 63A-63B are respective schematic cross-sectional views of another embodiment of the bladder syringe in which a sensor array is provided in the interior wall of the cylindrical body of the bladder syringe.

FIGS. 71A-71C are, respectively, a perspective view, a schematic cross-sectional view, and a detail view of detail 71C in FIG. 71B of another embodiment of the bladder syringe that incorporates an alternative arrangement for securing the cap-bladder assembly to the cylindrical body.

FIG. 80 is a perspective view of a plurality of cap-bladder assemblies packaged on a long bandolier protective strip.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, and features illustrated in the accompanying drawing figures and described herein are simply exemplary and should not be considered as limiting.

Figure 6:
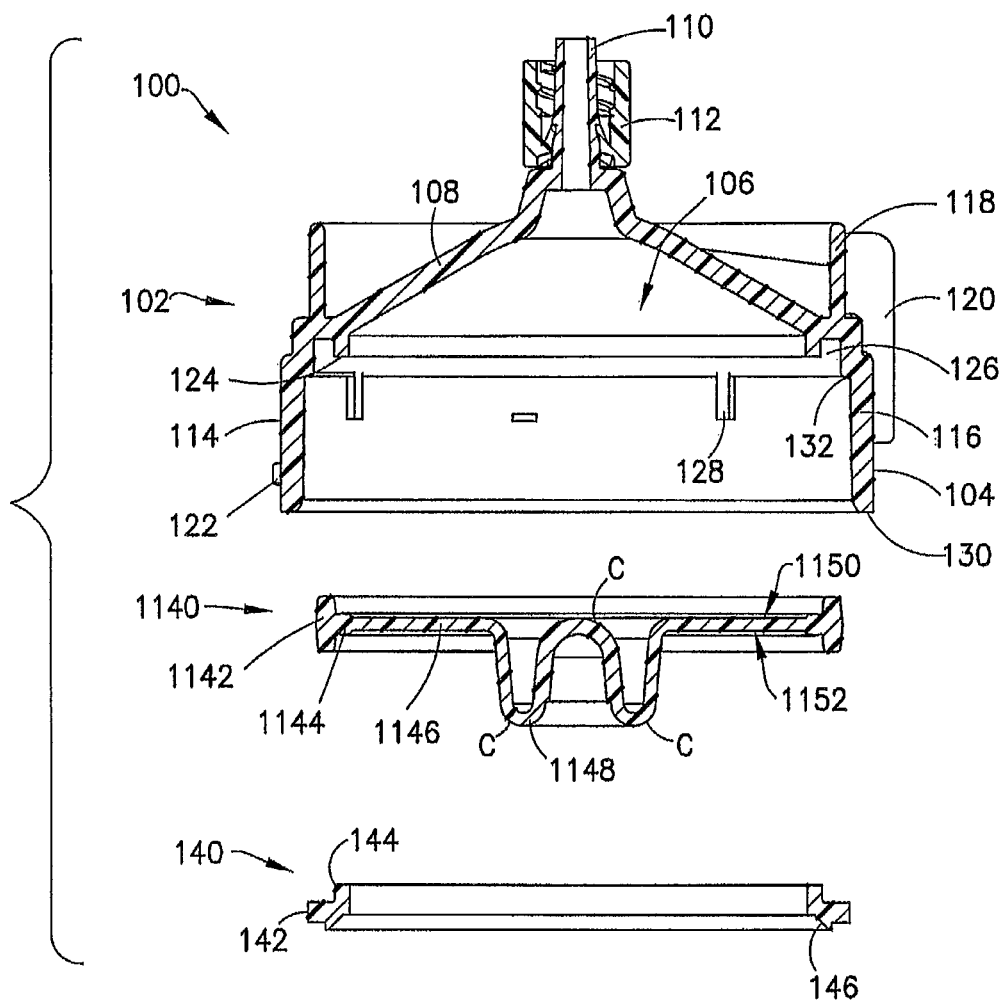
FIG. 6 is an exploded and cross-sectional view of the cap-bladder assembly shown in FIG. 5.
Figure 7:
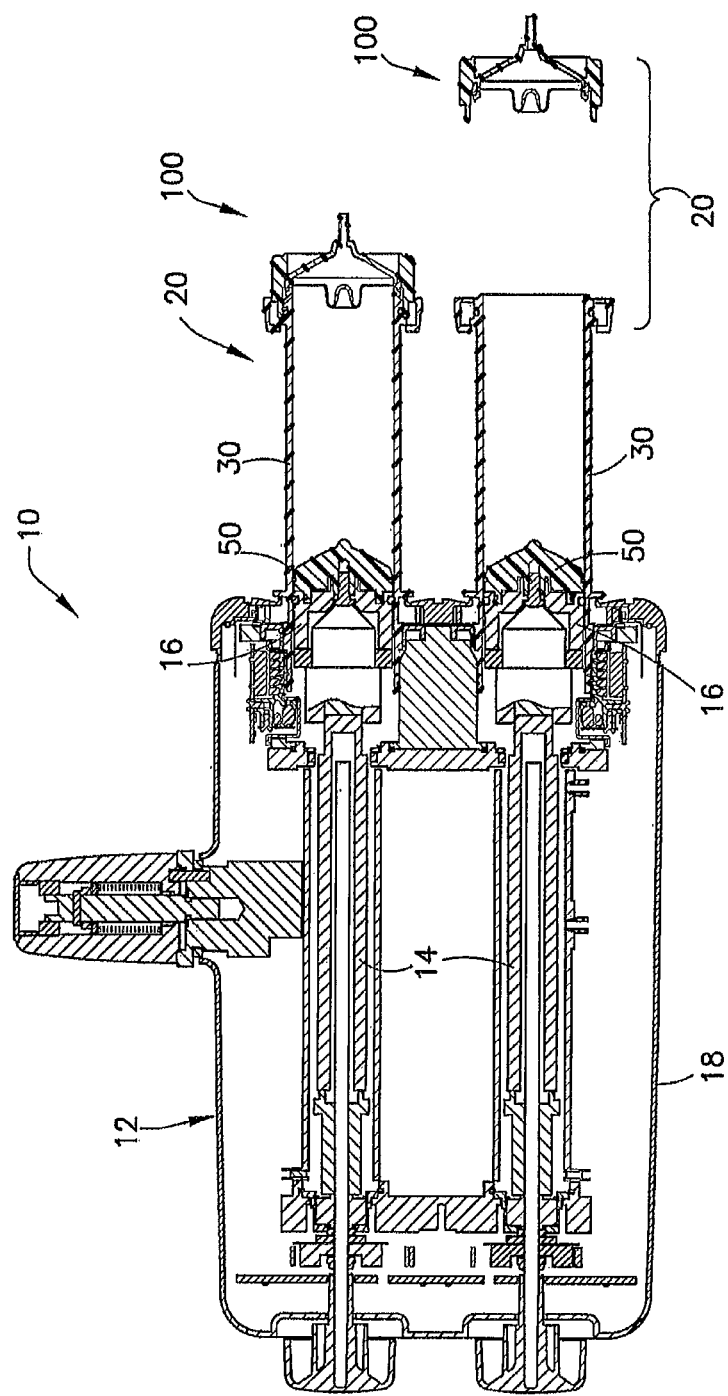
FIG. 7 is a cross-sectional view showing a fluid delivery system utilizing the bladder syringe shown in FIGS. 1A-1B.

Referring initially to FIGS. 1-7 and particularly FIG. 7, a fluid delivery system 10 generally comprises a power fluid injector head 12, such as a Stellant® power injector platform manufactured by Medrad, Inc., and a bladder syringe 20 as described in detail herein. As is known in the medical field, injecting contrast media into the bloodstream of patients enables visualization of various pathologies through X-Ray, Computed Tomography (CT), Magnetic Resonance (MR), or other medical imaging modalities. Contrast delivery is most effective and efficient using a power injector, such as the Stellant® power injector, that can be programmed to deliver specific amounts of contrast agent and/or saline at specific flow rates. A power injector may be used in diagnosing stroke, heart disease, cancer, vascular disease, physical injury, digestive disorder, etc. The fluid injector 12 comprises two (2) linearly reciprocal piston elements 14 which each have a distal piston interface 16 adapted to engage a syringe plunger disposed within a syringe body. The piston elements 14 are enclosed within a housing 18 and specific details of a power injector platform and syringe elements used therewith may be found in U.S. Pat. No. 5,383,858 to Reilly et al.; U.S. Pat. No. 5,873,861 to Hitchins et al.; and U.S. Pat. No. 6,652,489 to Trocki et al., all assigned to Medrad, Inc. and each incorporated herein by reference for disclosure related to the foregoing elements. This disclosure is explicitly not limited to utilizing the bladder syringe 20 with contrast media but may be used for any medicinal fluid to be delivered to a patient.

The bladder syringe 20 is a multi-component or composite device generally comprising a mounting ring 22, a cylindrical body 30, a plunger element 50 disposed in the cylindrical body 30, and a cap-bladder assembly 100 comprising a cap 102, retainer ring 140, and a bladder 1140. The bladder syringe 20 is adapted for use in CT, MR and like procedures and operable at typical operating pressures of about 300-400 psi, and the bladder 1140 may be expanded to hold fluid volumes on the order of 200 ml. The cap-bladder assembly 100 is adapted to be secured to the cylindrical body 30 by the mounting ring 22. Each of the foregoing components is discussed hereinafter in detail. The cylindrical body 30 is a unitary, typically, cylindrical body having a distal end 32 and a proximal end 34 and is typically a reusable component, while the cap-bladder assembly 100 is typically a single-use component. The cylindrical body 30 has an interior wall 36 that defines a throughbore 37 between the distal and proximal ends 32, 34. The proximal end 34 is adapted to interface with the fluid injector 12 and includes a circumferential flange 38 positioned to engage the front end of the housing 18 of the fluid injector 12 to properly seat the cylindrical body 30 relative to the fluid injector 12. Additionally, in the illustrated embodiment, two opposed bayonet attachment flanges 40 are provided at the proximal end 34 for interfacing with the fluid injector 12 to secure the cylindrical body 30 to the fluid injector 12. Further details relating to the circumferential flange 38 and attachment flanges 40 used to properly interface the cylindrical body 30 with the fluid injector 12 may be found in the foregoing Medrad, Inc. patents which discuss similar interfacing features for securing a Stellant® CT syringe to a Stellant® fluid injector. While the foregoing interfacing features 38, 40 provided on the cylindrical body 30 are described for interfacing the cylindrical body 30 to a Stellant® fluid injector, this description is provided for exemplary purposes and the proximal end 34 of the cylindrical body 30 may have any suitable configuration for interfacing with any suitable power fluid injector known in the medical field for power fluid delivery applications. The Stellant® fluid injector and the proximal end features of a Stellant® syringe, as described in the foregoing Medrad, Inc. patents, are provided for exemplary purposes only and should not be considered limiting. For example, the interface between the proximal end 34 of the cylindrical body 30 and fluid injector 12 may take other front-loading arrangements as disclosed in the foregoing Trocki et al. patent, or in U.S. Pat. No. 7,419,478 to Reilly et al. and assigned to Medrad, Inc. (additionally incorporated herein by reference). An adapter may also be used to connect the cylindrical body 30 to the fluid injector 12 as disclosed in U.S. Pat. No. 5,520,653 to Reilly et al., or in U.S. Pat. No. 7,497,843 to Castillo et al. and U.S. Pat. No. 6,726,657 to Dedig et al., all assigned to Medrad, Inc. and incorporated herein by reference for these teachings. All of the foregoing Medrad, Inc. patents disclose various apparatus and methods for mounting a syringe body to a fluid injector, whether a single-syringe fluid injector or multi-syringe fluid injector, and, further, disclose various apparatus and methods for interfacing a syringe plunger with a piston element of the fluid injector. Thus, these patents are incorporated by reference into this disclosure at least for teaching apparatuses and methods for interfacing the cylindrical body 30 to the fluid injector 12 and, further, for interfacing the piston element or elements 14 of the fluid injector 12 with a plunger element 50 disposed within the cylindrical body 30. Suitable embodiments of a syringe plunger may also be found in the foregoing Medrad, Inc. patents which may be utilized for the plunger element 50, augmented with the internal passageways and flow path elements described herein in connection with the plunger element 50 that are specific for use with the cap-bladder assembly 100. Further, the housing 18 of the fluid injector 12 may comprise a light ring (not shown) that can encompass all or part of the axial length of the cylindrical body 30 and all or part of the cap-bladder assembly 100 to sterilize the cylindrical body 30 and all or part of the cap-bladder assembly 100 with ultraviolet light (UV). Additionally, cylindrical body 30 may comprise a barrier or membrane (not shown) within the bore 37 near the proximal end 34 of the cylindrical body 30 that acts as a barrier to keep fluid from entering the injector housing 18 in the event of failure of the bladder 1140. The barrier forms a reservoir chamber that catches spilled fluid.

The distal end 32 of the cylindrical body 30 is formed with an exterior mounting collar 42. Additionally, the distal end 32 of the cylindrical body 30 is formed with an end flange or collar 44 having a tapered rim 45 for interfacing with the cap-bladder assembly 100. The mounting collar 42 is axially spaced from the end flange 44 and a recess or groove 46 is defined between the mounting collar 42 and the end flange or collar 44. This recess or groove 46 is provided with a sealing O-ring 48 for forming a substantially fluid-tight or leak proof seal with the cap-bladder assembly 100 as described hereinafter. The cylindrical body 30 may be made of any suitable plastic material, desirably a clear plastic material, such as, but not limited to, polycarbonate, acrylic, or polyester.

In brief, during the operation of the bladder syringe 20, as the piston element 14 of the fluid injector 12, which is connected to the plunger element 50 in the cylindrical body 30, retracts in the throughbore 37 of the cylindrical body 30, a vacuum is generated in the space between the plunger element 50 and the bladder 1140 of the cap-bladder assembly 100 which expands the bladder 1140 to draw in fluid. To generate and maintain a vacuum in the cylindrical body 30, the sealing O-ring 48 is used to maintain a generally fluid-tight seal between the cap-bladder assembly 100 and the cylindrical body 30, and an additional sealing ring 88 (discussed in detail herein) is provided about the plunger element 50 to establish and maintain a generally fluid-tight seal between the plunger element 50 and the interior wall 36 of the cylindrical body 30. A spliced hollow O-ring may be used in place of the sealing O-ring 48 to lower the insertion force of the cap-bladder assembly 100 over the O-ring 48. A lubrication coating may also be added to the sealing O-ring 48.

The mounting ring 22 is used to secure the cap-bladder assembly 100 to the cylindrical body 30 as described in detail herein. The mounting ring 22, in the embodiment illustrated, is of split-ring construction formed by two half-ring portions 24. Each half-ring portion 24 has an L-shaped wall in transverse cross-section which is defined by a longer axial wall 25 and a shorter, inward-extending radial wall 26. When the respective half-ring portions 24 are joined together to form the mounting ring 22, the radial walls 26 define an inner diameter of the mounting ring 22 that is approximately equal to or slightly larger than the outer diameter of the cylindrical body 30. In this manner, the radial walls 26 of each half-ring portion 24 may engage the mounting collar 42 on the cylindrical body 30 in interference engagement in an axial direction of the cylindrical body 30. Additionally, the mounting collar 42 desirably extends radially outward sufficiently to seat against the interior side of the axial wall 25 of each half-ring portion 24. The axial wall 25 of each of the half-ring portions 24 further includes one or more inward-extending radial tabs or threads 28 to engage with corresponding structures, such as tabs or threads, on the cap-bladder assembly 100 as described herein. While not shown in detail in the accompanying figures, inter-engaging structures may be provided to join together the terminal ends of the respective half-ring portions 24 to form the mounting ring 22. Such inter-engaging structures may be of a nature to provide a releasable snap-fit connection between the terminal ends of the respective half-ring portions 24. Other suitable releasable connections between the terminal ends of the respective half-ring portions 24 may be used, such as by use of a mechanical connection using mechanical fasteners, adhesives, ultrasonic welding, or interference fits. If desired, the two half-ring portions 24 may be joined together at one terminal end with a hinge structure, such as a living hinge, so that only one securing arrangement is needed to secure the remaining free terminal ends of the two half-ring portions 24 together to assemble the mounting ring 22 and secure the same in association with the cylindrical body 30 and the cap-bladder assembly 100. This hinged configuration is akin to a clamshell arrangement.

Figure 1A:
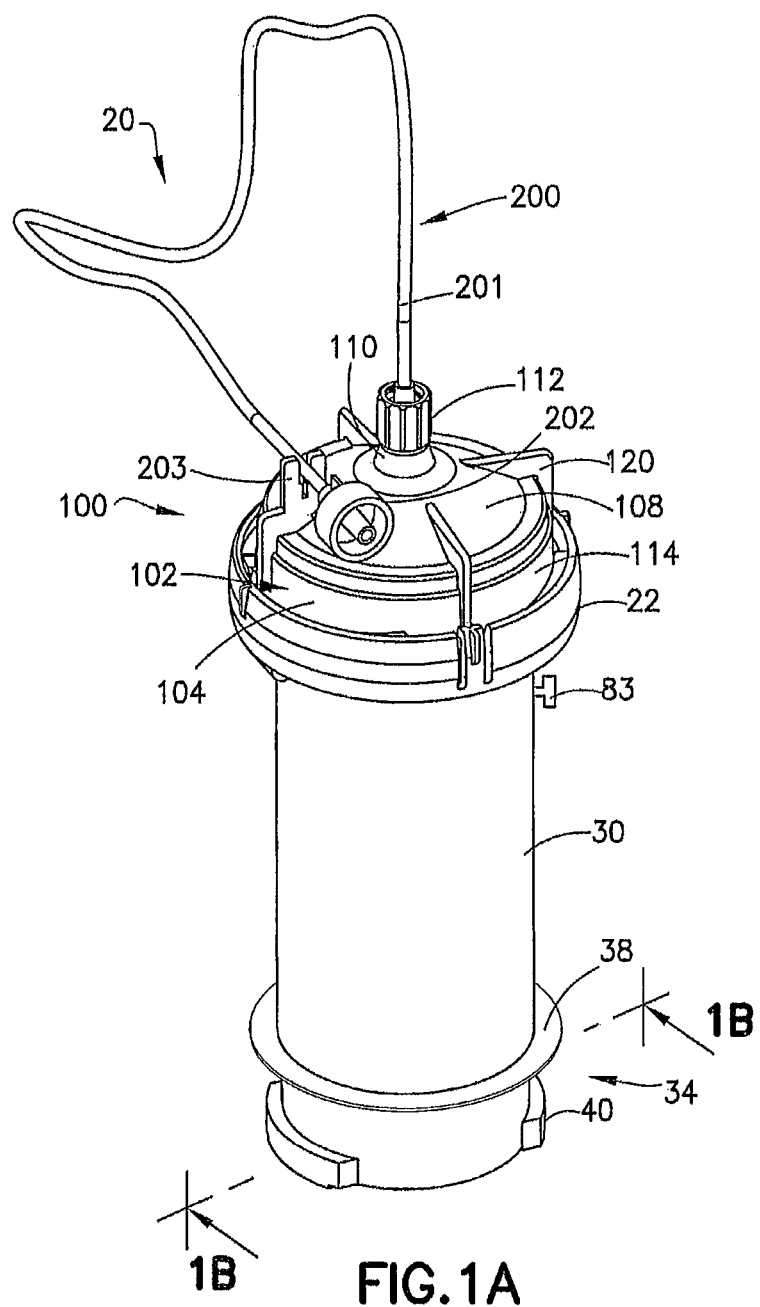
FIG. 1A is a perspective view of a bladder syringe for a fluid delivery system according to one embodiment.
Figure 1B:
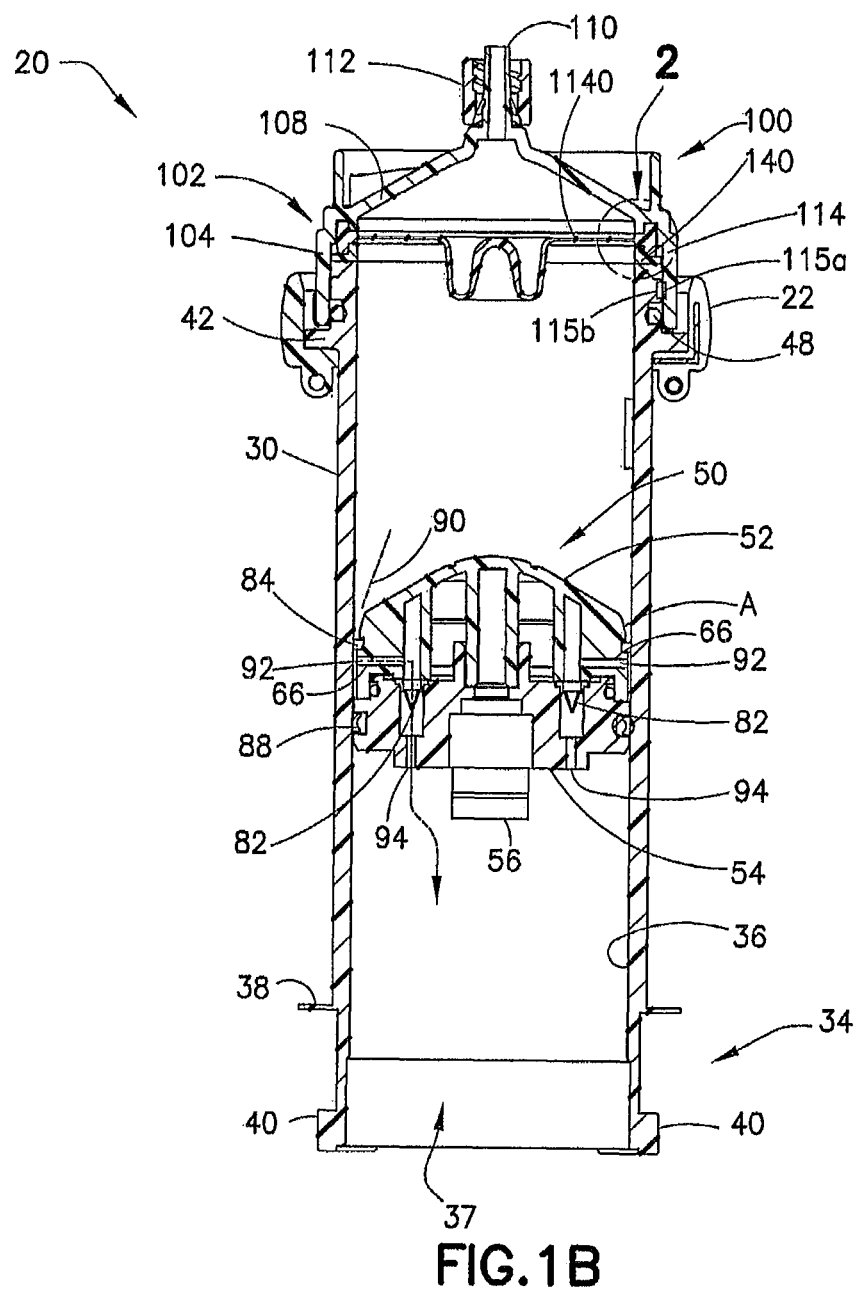
FIG. 1B is a cross-sectional view of the bladder syringe shown in FIG. 1A.
Figure 2:
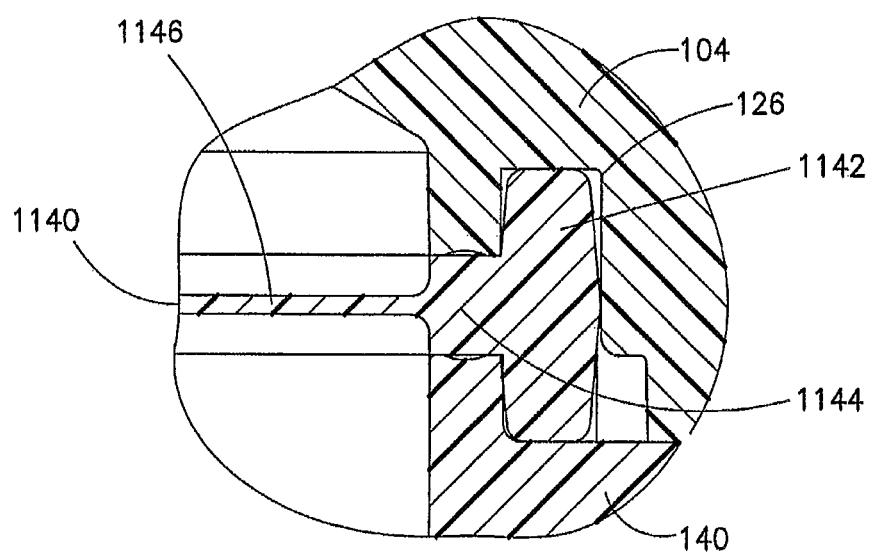
FIG. 2 is a detail view of Detail 2 in FIG. 1B
Figure 3:
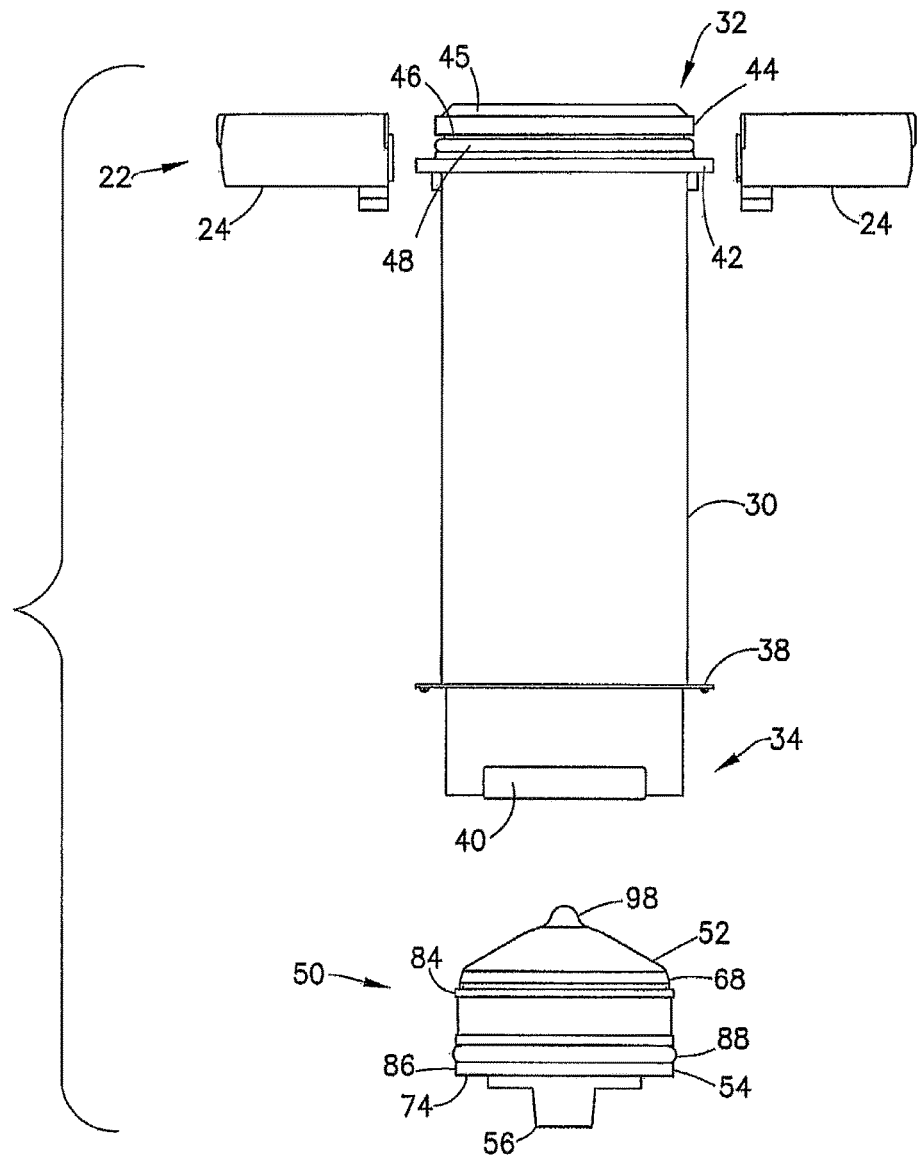
FIG. 3 is an exploded view showing a cylindrical body, a plunger element, and a mounting ring of the bladder syringe shown in FIGS. 1A-1B.
Figure 4:
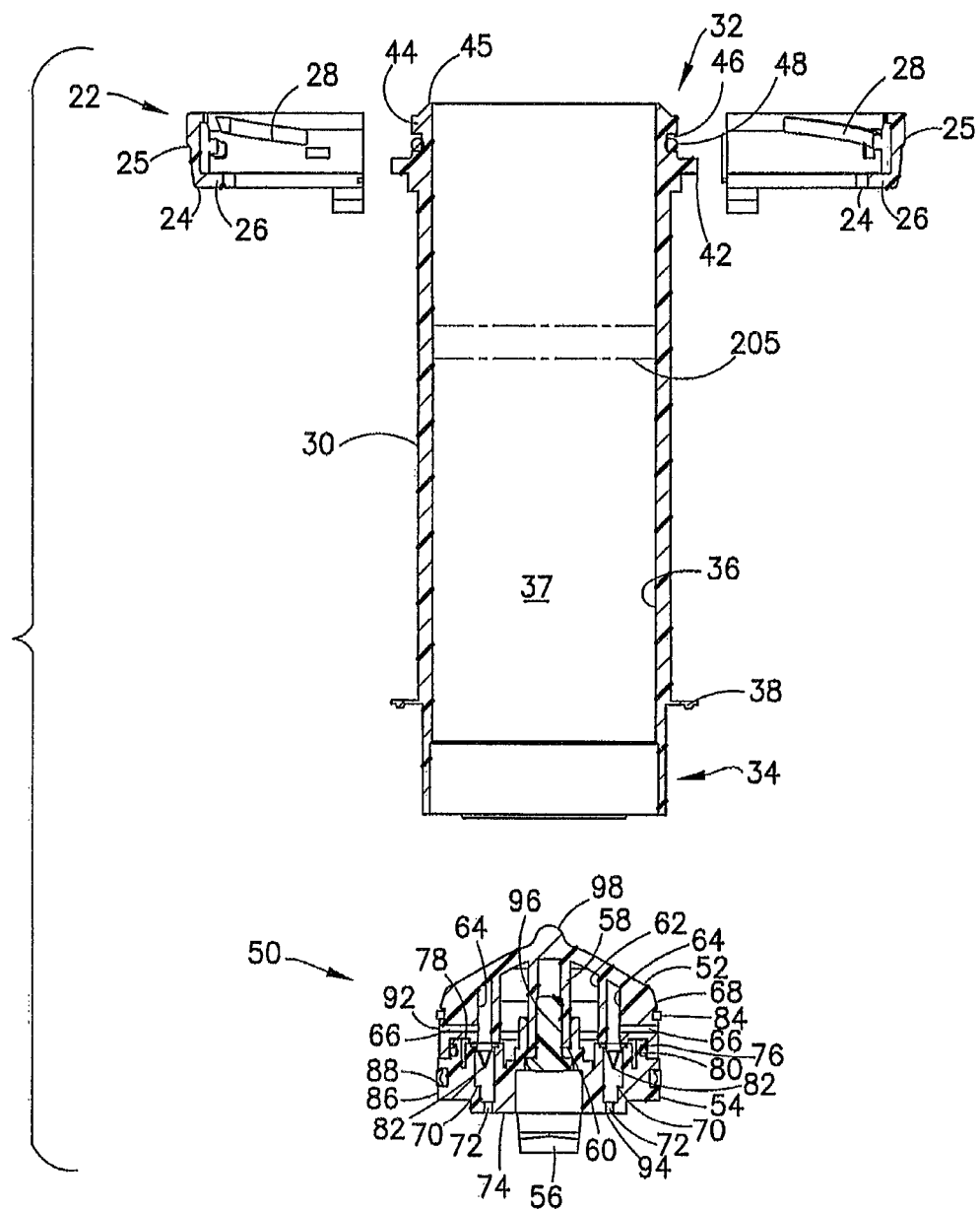
FIG. 4 is an exploded and cross-sectional view of the various components shown in FIG. 3.
Figure 5:
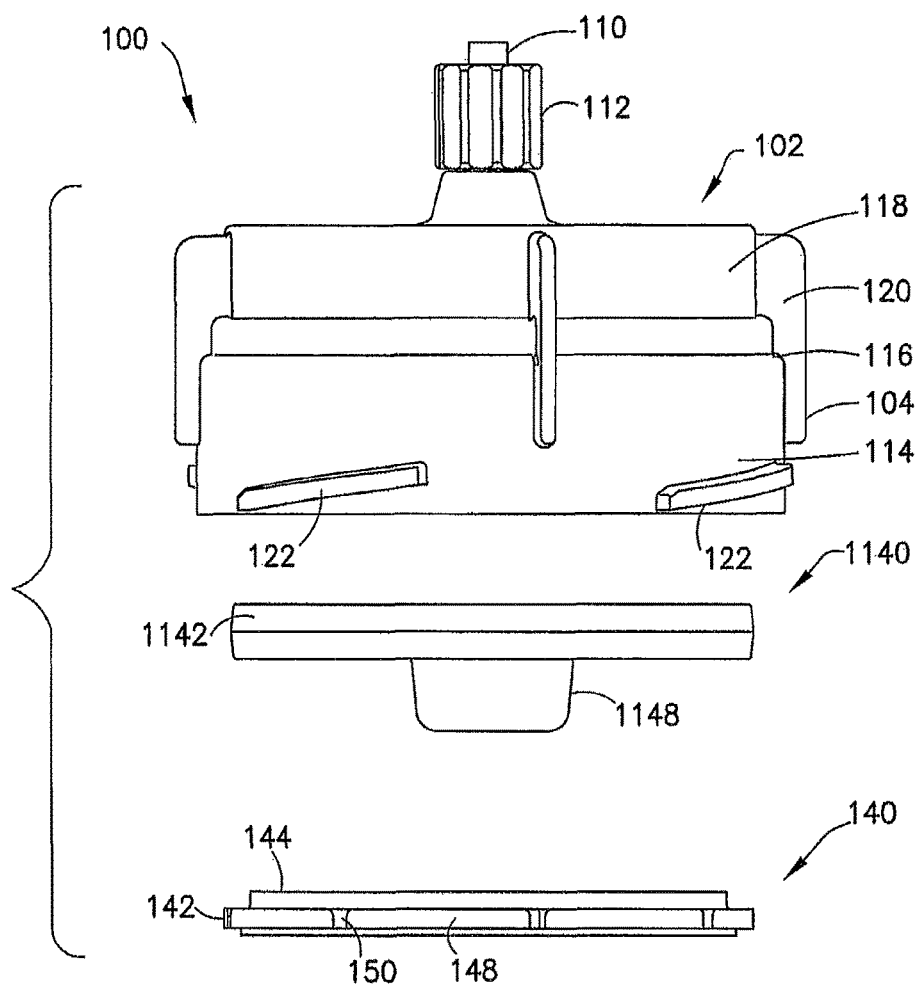
FIG. 5 is an exploded view of a cap-bladder assembly of the bladder syringe shown in FIGS. 1A-1B.

The plunger element 50 is disposed within the cylindrical body 30 and comprises, in the embodiment shown in FIGS. 1B and 4, a two-piece body formed by a distal or top portion 52 and a proximal or rear portion 54. The proximal portion 54 includes a pair of legs 56 for interfacing with the piston interface 16 on the piston elements 14 of the fluid injector 12. If desired, this interface may be a fusible link in that should this interface become wet with liquid, such as may occur when the bladder 1140 leaks or ruptures, the link breaks preventing further reciprocal movement of the piston element 50 (e.g., the plunger element 50 mechanically disconnects from the piston element 14). The legs 56 on the proximal portion 54 of the plunger element 50 are adapted so that the piston interface 16 may engage the plunger element 50 to capture the plunger element 50 whereby the piston element 14 may reciprocally move the plunger element 50 within the cylindrical body 30. As an example, the legs 56 may flex apart when contacted by the piston interface 16 so that the interface 16 enters the space between the flex legs 56. The flexibility of the flex legs 56 is such that the flex legs 56 may snap onto a flange or like structure on the piston interface 16 whereby the capture of the plunger element 50 by the piston interface 16 of the piston element 14 may be completed. A suitable embodiment of the flex legs 56 may be found in the foregoing Reilly et al. (U.S. Pat. No. 5,383,858) or Hitchins et al. patents, which were incorporated herein by reference. The distal portion 52 of the plunger element 50 may comprise a central post 58 that engages a corresponding pocket 60 defined by the proximal portion 54, and the engagement of the distal portion 52 to the proximal portion 54 may be accomplished by a frictional engagement between the central post 58 and the pocket 60. A suitable medical grade adhesive may further be provided at the interface between the central post 58 and the pocket 60 to secure the connection between the distal portion 52 and the proximal portion 54. A mechanical fastener may also be used in addition or apart from the foregoing adhesive connection between the distal portion 52 and the proximal portion 54, or these components may be ultrasonically welded together as another alternative.

The distal portion 52 of the plunger element 50 may be formed with an annular chamber 62 about the central post 58 and a pair of axially-directed passageways 64 is located radially outward on either side of the annular chamber 62. The respective axial passageways 64 are in fluid communication with the bore 37 of the cylindrical body 30 via an intersecting radial passageway 66 that extends outward to a circumferential outer surface 68 of the distal portion 52 of the plunger element 50. A porous plug or filter similar to the porous plug 134 described herein in connection with FIGS. 10A-10B may be provided in the radial passageway 66 to prevent bladder 1140 from "extruding" into the radial passageway 66 during operation. The annular chamber 62 may also be formed as two separate passageways on either side of the central post 58 if desired. The proximal portion 54 of the plunger element 50 is likewise formed with a pair of axially-directed passageways 70 that generally correspond to/align with the axial passageways 64 in the distal portion 52 of the plunger element 50. The respective axial passageways 70 in the proximal portion 54 of the plunger element 50 generally have a larger diameter than the corresponding axial passageways 64 in the distal portion 52 of the plunger element 50 and, further, each define an optional reduced diameter portion 72 extending to a proximal or rear surface 74 of the proximal portion 54 of the plunger element 50. Moreover, the proximal portion 54 of the plunger element 50 comprises a distal-facing rim 76 formed radially outward from the respective axial passageways 70 and which is shaped and positioned to engage a corresponding receiving annular groove or recess 78 defined in a proximal-facing side of the distal portion 52 of the plunger element 50. The engagement between the distal-facing rim 76 on the proximal portion 54 of the plunger element 50 and the proximal annular groove 78 in the distal portion 52 of the plunger element 50 may be a frictional engagement augmented with a suitable medical grade adhesive if desired. Additionally, an internal O-ring 80 may be disposed at the interface between the distal-facing rim 76 on the proximal portion 54 of the plunger element 50 and the proximal annular groove 78 in the distal portion 52 of the plunger element 50, if desired, to provide a fluid tight seal between the distal portion 52 and the proximal portion 54. As noted previously, a mechanical fastener may also be used in addition or apart from an adhesive connection between the distal portion 52 and the proximal portion 54, or these components may be ultrasonically welded together as another alternative which eliminates the need for the mechanical fastener, an additional securing adhesive, and, further, the internal O-ring 80.

Further, a one-way check valve 82 may be seated or disposed in each of the axial passageways 70 in the proximal portion 54 of the plunger element 50. The check valves 82 may be duckbill-type check valves having a preset opening pressure. Other suitable valve designs may also be used and the check valves 82 are not limited to duckbill-type check valves. Moreover, while the check valves 82 are presented in this disclosure in connection with the plunger element 50, a single sidewall check valve 83, as shown in FIG. 1A, may alternatively be provided in the sidewall of the cylindrical body 30 just below the cap-bladder assembly 100 and the axial location of the bladder 1140 in the bore 37 of the cylindrical body 30 to vent air from the cylindrical body 30. In this alternative configuration, as the plunger element 50 moves forward in the cylindrical body 30 toward the cap-bladder assembly 100, air is forced out of the cylindrical body 30 via the sidewall check valve 83, and as the plunger element 50 retracts rearward or proximally in the cylindrical body 30, the sidewall check valve 83 closes to establish a vacuum in the cylindrical body 30. The inlets to the respective axial passageways 70 in the proximal portion 54 of the plunger element 50 may be shaped to seat or support the respective check valves 82. Thus, the check valves 82 provide the interface between the axial passageways 64 in the distal portion 52 of the plunger element 50 and the axial passageways 70 in the proximal portion 54 of the plunger element 50. The circumferential or radial outer surface 68 of the distal portion 52 of the plunger element 50 is shaped to define a tapered annular space A with the interior wall 36 of the cylindrical body 30. Additionally, the radial outer surface 68 of the distal portion 52 of the plunger element 50 supports a guide ring 84 disposed in a circumferential groove or recess provided in the radial outer surface 68. Similarly, a circumferential or radial outer surface 86 of the proximal portion 54 of the plunger element 50 defines a circumferential groove or recess for supporting a sealing O-ring 88 or "seal ring" 88 that provides a generally fluid-tight or leak proof seal with the interior wall 36 of the cylindrical body 30.

Figure 8:
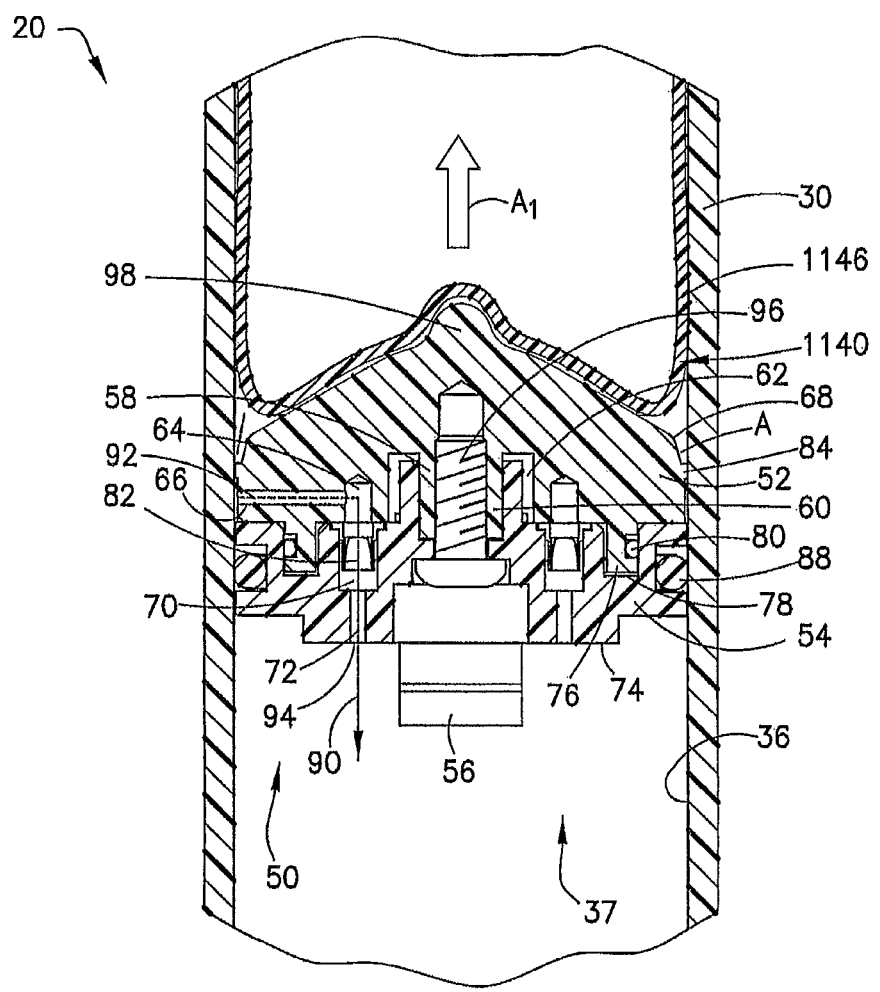
FIG. 8 is a partial cross-sectional view of the bladder syringe of FIGS. 1A-1B showing the interaction between the bladder and the plunger element of the bladder syringe during forward movement of the plunger element.
Figure 9:
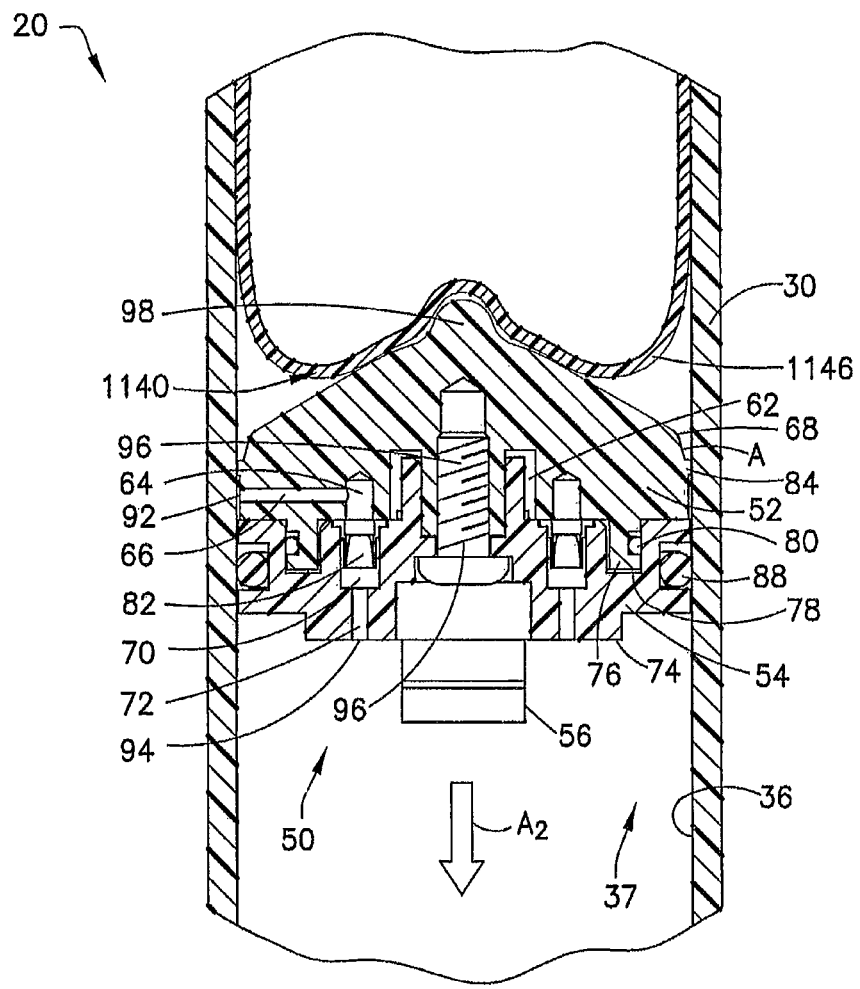
FIG. 9 is a partial cross-sectional view of the bladder syringe of FIGS. 1A-1B showing the interaction between the bladder and the plunger element of the bladder syringe during rearward movement of the plunger element.

Referring additionally to FIGS. 8-9, also discussed further herein, a fluid, namely air, vent path 90 is established through the plunger element 50 due to the foregoing internal configuration of the plunger element 50 to allow venting of the airspace in the bore 37 distal or forward of the plunger element 50 when the cap-bladder assembly 100 is disposed on the distal end 32 of the cylindrical body 30. This vent path 90 is generally defined as having an inlet at an inlet port 92 to the radial passageway 66 in the distal portion 52 of the plunger element 50 which is located at the radial outer surface 68 of the distal portion 52 of the plunger element 50 and desirably in close proximity to the seal ring 88. The vent path 90 extends through the radial passageway 66 to the axial passageway 64 in the distal portion 52 of the plunger element 50 and, further, through the check valve 82 and the axial passageway 70 in the proximal portion 54 of the plunger element 50. The vent path 90 has an outlet or exit at an outlet or exit port 94 at the reduced diameter portion 72 of the axial passageway 70 in the proximal portion 54 of the plunger element 50. The outlet or exit port 94 of the axial passageway 70 in the proximal portion 54 of the plunger element 50 is shown located at the proximal or rear surface 74 of the proximal portion 54 of the plunger element 50 but may be at any location proximal or rearward of the seal ring 88.

The annular space A about the radial outer surface 68 of the distal portion 52 of the plunger element 50 is defined generally between the radial outer surface 68 and the interior wall 36 of the cylindrical body 30 to allow airflow to reach the inlet port 92 to the radial passageway 66 in the distal portion 52 of the plunger element 50. The annular space A is provided for limiting the potential for the bladder 1140 to be pinched against the interior wall 36 of the cylindrical body 30 by operation of the plunger element 50. Additionally, the guide ring 84 disposed about the radial outer surface 68 of the distal portion 52 of the plunger element 50 is shaped and sized to permit airflow to reach the inlet port 92 to the radial passageway 66 in the distal portion 52 of the plunger element 50.

In particular, the guide ring 84 is located distal of the inlet port 92 to the vent path 90 and is designed to have minimal clearance with the interior wall 36 of the cylindrical body 30 to allow air to reach the inlet port 92. However, this clearance is small enough to keep the material of the bladder 1140 in the cap-bladder assembly 100 from being pulled over or into the inlet port 92 to the vent path 90, thereby obstructing air flow into the vent path 90 through the plunger element 50. In other words, the guide ring 84 generally keeps the material of the bladder 1140 from being "pinched" between the radial outer surface 68 of the distal portion 52 of the plunger element 50 and the interior wall 36 of the cylindrical body 30 which could obstruct air flow into the inlet port 92 to the vent path 90 through the plunger element 50. The guide ring 84 may alternatively be designed to contact the interior wall 36 of the cylindrical body 30, but may include a slot or slots (not shown) in the outer circumference of the guide ring 84 to allow air to pass to the inlet port 92 of the vent path 90. The inlet port 92 of the vent path 90, which is the inlet to the radial passageway 66 in the distal portion 52 of the plunger element 50, could also incorporate a flap or a porous plastic cover, as discussed herein in connection with FIG. 10B, to protect the inlet port 92 during operation of the plunger element 50 to fill or dispense fluid from the bladder 1140. In particular, such a flap or porous plastic cover is used to protect the bladder 1140 from "extruding" into the inlet port 92 and may eliminate the need for a separate guide ring 84. As a result, the seal ring 88 may be used to prevent the bladder 1140 from being "pinched" between the distal portion 52 of the plunger element 50 and the interior wall 36 of the cylindrical body 30.

As shown in FIGS. 1B and 4, the inlet port 92 is located axially between the guide ring 84 disposed about the radial outer surface 68 of the distal portion 52 of the plunger element 50 and the seal ring 88 is disposed about the radial outer surface 86 of the proximal portion 54 of the plunger element 50. FIGS. 8-9 alternatively illustrate that, if desired, the guide ring 84 may be formed integrally with the distal portion 52 of the plunger element 50 rather than being a separate ring structure disposed about the distal portion 52. A further comparison between FIGS. 1B, 4 and 8-9 shows that a mounting mechanical fastener 96 may additionally be used to secure the connection between the central post 58 on the distal portion 52 and the corresponding pocket 60 defined by the proximal portion 54 of the plunger element 50.

Moreover, from FIGS. 1B, 4, and 8-9, it will be clear that two distinct vent paths 90 are present through the plunger element 50 due to the internal passage configuration of the plunger element 50. Such dual vent paths 90 are ideally provided on opposing lateral sides of the plunger element 50 as will be clear from FIGS. 1B and 4. However, FIGS. 8-9 alternatively show that only one such vent path 90 may be needed in accordance with this disclosure to allow venting of the airspace in the bore 37 of the cylindrical body 30, distal or forward of the plunger element 50 when the cap-bladder assembly 100 is disposed on the distal end 32 of the cylindrical body 30. Additionally, FIGS. 8-9 alternatively show that the locations for the distal-facing rim 76 and the annular groove or recess 78 may be reversed, with the rim 76 being formed on the proximal-facing side of the distal portion 52 of the plunger element 50 and the annular groove or recess 78 being formed in the distal-facing side of the proximal portion 54 of the plunger element 50. Furthermore, FIGS. 8-9 illustrate that the distal portion 52 of the plunger element 50 may optionally define a rounded point or nub 98 for interfacing with (for supporting, holding, and centering) the bladder 1140 of the cap-bladder assembly 100 such as a central well portion 1148 of the bladder 1140 shown in FIGS. 12-13 discussed herein. The respective O-rings comprising the internal ring 80, guide ring 84, and seal ring 88 may be made of any suitable sealing elastomeric material such as silicone, EPDM, nitrile, and urethane and may have a lubrication coating applied thereto. Suitable materials for forming the distal and proximal portions 52, 54 of the plunger element 50 include plastic materials such as, but not limited to, ABS or polycarbonate.

Figure 35A:
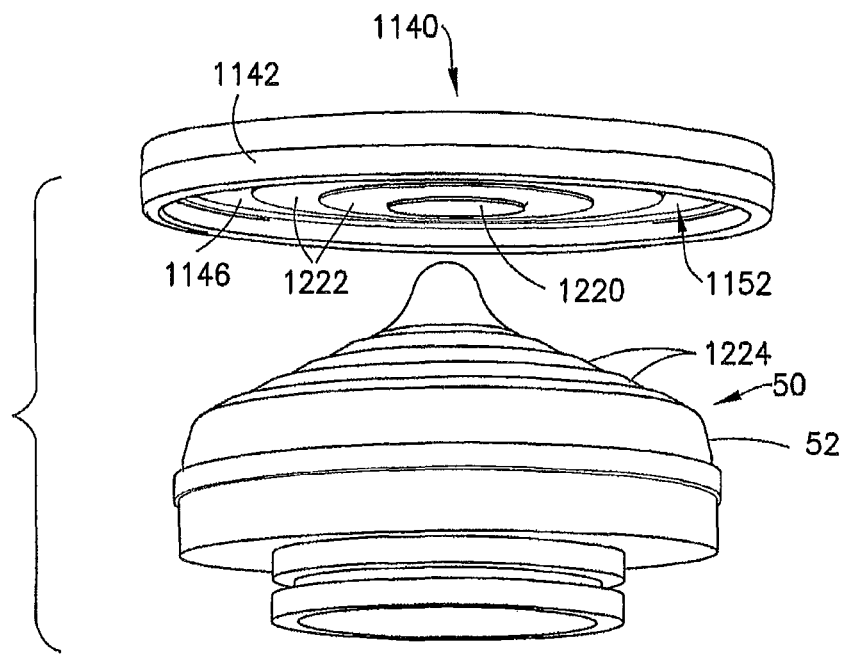
FIGS. 35A-35B are respective perspective and cross-sectional views of a bladder and plunger element having cooperating surface texturing for use in the bladder syringe of FIGS. 1A-1B.
Figure 35B:
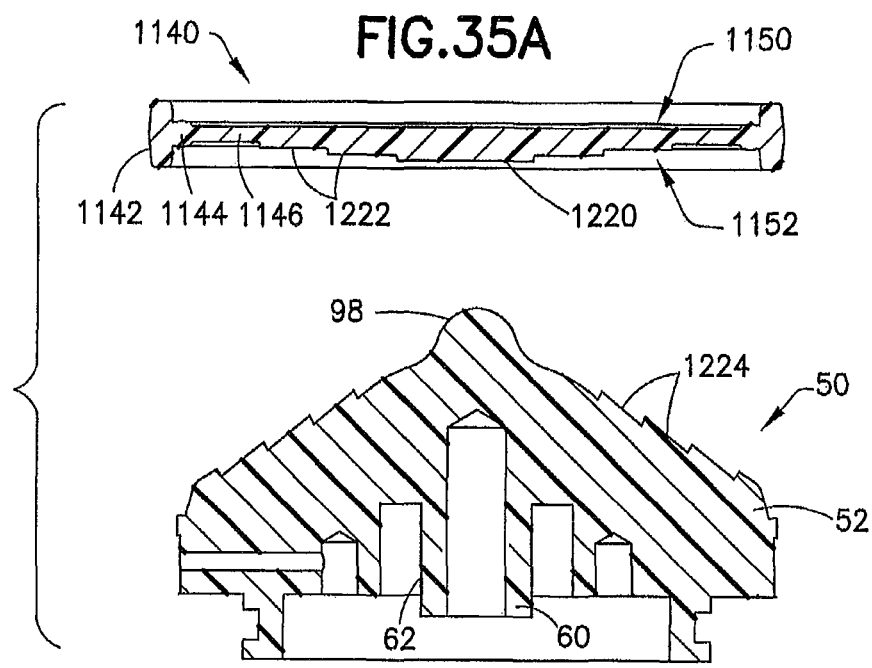

As will be understood from comparing FIG. 1B and FIGS. 8-9, the distal portion 52 of the plunger element 50 may comprise different shapes, with the embodiment shown in FIGS. 8-9 comprising a distal point or nub 98. Differing shapes for the distal portion 52 can lead to different efficiencies for purging air from the cylindrical body 30 in the airspace forward of the plunger element 50. The distal portion 52 may exhibit the shape shown in FIG. 1B or FIGS. 8-9 and, further, may exhibit an elongated conical shape with a rounded tip or end much like FIG. 1B or an elongated conical shape with a distal point or nub 98. Such an extended or elongated conical shape may have different taper angles such as 10°, 30°, or 45° from horizontal, as examples. In the embodiment shown in FIGS. 8-9, the distal portion 52 with the extended point or nub 98 provides more surface area to resist the distribution of the bladder 1140 toward the interior wall 36 of the cylindrical body 30 during withdrawal operation of the plunger element 50 in the bladder syringe 20. Additionally, surface texturing, as shown in FIGS. 35A-35B discussed herein, such as external ribs on the distal portion 52 of the plunger element 50 may increase the resistance to the distribution of the bladder 1140 to the interior wall 36 of the cylindrical body 30 during withdrawal operation of the plunger element 50 in the bladder syringe 20. Corresponding surface features such as texturing may also be provided on the membrane portion 1146 of the bladder 1140 facing the plunger element 50 as well (FIGS. 35A-35B).

The cap-bladder assembly 100 is generally adapted for connection with the distal end 32 of the cylindrical body 30 and this connection is secured with the mounting ring 22, as mentioned previously. The cap-bladder assembly 100 is typically intended to be a single-use component which may be adapted for use with the cylindrical body 30, while the cylindrical body 30 may be reused multiple times for fluid delivery applications and potentially for multiple patients. The cylindrical body 30, or base, serves as a pressure jacket for the bladder 1140 in the cap-bladder assembly 100. Thus, the cap-bladder assembly 100 is the portion of the bladder syringe 20 that is used to contain contrast media and/or flushing media or other medicinal fluid that is injected into a patient for diagnostic or treatment purposes. The piston elements 14 of the fluid injector 12 provide the forces needed to move the plunger element 50 within the bore 37 of the cylindrical body 30, and the vent path 90 through the plunger element 50 enables the airspace within the bore 37 between the plunger element 50 and the bladder 1140 to be vented to the atmosphere as a result of the movement of the plunger element 50. In particular, forward or distal movement of the plunger element 50 in the bore 37 of the cylindrical body 30 in the direction of arrow $A_1$ in FIG. 8 permits the airspace distal of the plunger element 50 and enclosed by the cap-bladder assembly 100 to be vented to the atmosphere via the vent path 90 described previously, and reverse or proximal movement of the plunger element 50 in the direction of arrow $A_2$ in FIG. 9 creates a vacuum in this space. This vacuum pressure acts upon the cap-bladder assembly 100 to fill the bladder 1140 of this assembly 100 with a desired injection fluid. Once filled with a desired amount of injection fluid, subsequent forward or distal operation of the piston element 14 of the fluid injector 12 in the direction of arrow $A_1$ in FIG. 8 causes the injection fluid to be dispensed from the cap-bladder assembly 100. While the discussion in this disclosure provides for drawing a vacuum in the bore 37 of the cylindrical body 30 to operate the bladder therein, it may also be possible to fill the bladder 1140 with pressurized fluid via the discharge conduit 110 on the cap body 104 of the cap 102 and use a regulator (not shown) in the discharge conduit 110 to limit output pressure of the fluid.

The cap-bladder assembly 100 generally comprises a cap 102 adapted for connection to the distal end 32 of the cylindrical body 30, a disc-shaped bladder 1140 which is disposed within the interior of the cap 102, and a retainer ring 140 used to secure the disc-shaped bladder 1140 within the cap 102. The cap 102 comprises a unitary cap body 104 defining an interior cavity 106. The cap body 104 includes a tapered or conical portion 108 that terminates in a distal discharge luer-type conduit 110 optionally having a threaded end connector 112. The distal tapered or conical portion 108 is connected radially to a cylindrical portion 114 in the form of an annular skirt or sidewall that is sized to receive the distal end 32 of the cylindrical body 30 therein. In certain embodiments of the cap 102, the cylindrical distal portion 114 of the cap body 104 may be omitted, as in FIG. 47C described herein as one example. The conical portion 108 provides structural rigidity for the cap-bladder assembly 100. Desirably, an electrical contact 115a may be provided on the end flange 44 at the distal end 32 of the cylindrical body 30 that is adapted to engage an opposing electrical contact 115b on the interior side of the cylindrical portion 114 of the cap body of the cap 102, and an electrical connection may be established between the opposing electrical contact 115a, 115b when the cap-bladder assembly 100 is mounted to the distal end 32 of the cylindrical body 30. This presence sensing arrangement may be communicated to the controller for the fluid injector 12 so that the presence of the cap-bladder assembly 100 on the cylindrical body 30 can be confirmed. The cylindrical portion 114 comprises a sidewall 116. The interior cavity 106 is generally defined by the distal conical portion 108 and the cylindrical portion 114 of the cap body 104. The opposing electrical contacts 115a, 115b may be provided between the cap body 104 and the distal end 32 of the cylindrical body 30 in the embodiment shown in FIG. 1A.

The cap body 104 optionally includes a cylindrical distal portion 118 in the form of an annular skirt that extends forward or distally from the radial wall connecting the distal conical portion 108 to the cylindrical portion 114 to partially enclose or shield the distal conical portion 108 and can further serve as a drip catcher. The cylindrical distal portion 118 is shown omitted from FIG. 1A. The cylindrical distal portion 118 is of a height that permits the distal discharge conduit 110 to extend outward from the distal conical portion 108. The exterior of the cap body 104 may have one or more finger flanges 120 bridging the cylindrical portion 114 and the cylindrical distal portion 118 to allow for easy handling of the cap 102 and the assembly of the cap 102 with the cylindrical body 30 and the mounting ring 22. However, the cylindrical distal portion 118 may be omitted, as shown in FIG. 1A, wherein the finger flanges are provided on the cap body 104 to bridge the conical portion 108 and the cylindrical portion 114. Additionally, the cylindrical portion 114 of the cap body 104 includes exterior tabs or threads 122 to engage with the inward-extending radial tabs or threads 28 on the half-ring portions 24 forming the mounting ring 22 to secure the cap 102 to the distal end 32 of the cylindrical body 30. The distal conical portion 108 of the cap body 104 includes a depending interior annular rib or rim 124 to interface with the bladder 1140 and with the retainer ring 140 used to maintain the bladder 1140 within the interior cavity 106 of the cap body 104. The annular rib or rim 124 defines a circumferential recess or groove 126 with the cylindrical portion 114 which accepts a portion of the bladder 1140 therein. The engagement of the bladder 1140 with this recess or groove 126 is secured by the retainer ring 140. Additionally, the cylindrical portion 114 includes one or more axially-extending tabs 128 to engage or interface with the retainer ring 140 to aid in securing the retainer ring 140 and the accompanying bladder 1140 within the interior cavity 106 of the cap body 104. Further, the axially-extending tabs 128 interface with the retainer ring 140 to prevent rotation thereof in the interior cavity 106 of the cap body 104. The cylindrical portion 114 defines a proximal rim or end 130 of the cap body 104 which is adapted to engage or seat against the mounting collar 42 on the cylindrical body 30. Additionally, the sidewall 116 of the cylindrical portion 114 defines an internal ledge 132 in the interior cavity 106 of the cap body 104 which provides a shoulder for engagement with the radial flange 142 of the retainer ring 140.

As described in the foregoing, the disc-shaped bladder 1140 is intended to be disposed within the interior cavity 106 of the cap body 104. In the embodiment shown in FIGS. 1-6, the bladder 1140 is a unitary element formed with an outer circumferential rib 1142 having a radially-inward extending portion 1144 and a thinner central membrane portion 1146. The outer circumferential rib 1142 extends outward from both sides of the membrane portion 1146 and forms the portion of the bladder 1140 that is used to mount the bladder 1140 to the retainer ring 140. In the embodiment illustrated in FIGS. 1-9, the central membrane portion 1146 includes a generally W-shaped central well portion 1148, as shown in FIG. 6. The bladder 1140 generally has a top or distal side 1150 which faces the distal conical portion 108 of the cap body 104 and a bottom or proximal side 1152 which faces the plunger element 50 when the cap-bladder assembly 100 is connected to the distal end 32 of the cylindrical body 30. One or both sides 1150, 1152 may be coated with a lubricious coating to limit frictional interaction with the interior wall 36 of the cylindrical body 30. The outer rib 1142 is adapted to engage or be received in the groove or recess 126 between the annular rib or rim 124 extending proximally from the distal conical portion 108 of the cap body 104 and the sidewall 116 of the cylindrical portion 114 of the cap body 104, with the distal-facing side of the radial portion 1144 of the outer rib 1142 seated against the annular rib or rim 124. The outer rib 1142 and radial portion 1144 also mount the bladder 1140 to the retainer ring 140 as described herein.

The retainer ring 140 generally has an L-shaped transverse cross-section formed by a radial flange 142 and an axial flange 144. The retainer ring 140 further defines a tapered inner rim 146 that is shaped to engage the tapered rim 45 on the end flange 44 at the distal end 32 of the cylindrical body 30 when the cap-bladder assembly 100 is mounted to the distal end 32 of the cylindrical body 30. The axial flange 144 has an outer diameter generally corresponding to the inner diameter of the outer rib 1142 of the bladder 1140 so that the axial flange 144 may seat against the proximal-facing side of the radial portion 1144 of the outer rib 1142 of the bladder 1140, while the radial flange 142 seats in engagement with the proximal side or end of the outer rib 1142. The radial flange 142 of the retainer ring 140 further has an outer diameter generally corresponding to the inner diameter of the sidewall 116 so that the radial flange 142 may seat against the interior of the sidewall 116 of the cap body 104. The frictional engagement between the outer diameter of the radial flange 142 and the inner diameter of the sidewall 116 of the cylindrical portion 114 of the cap body 104 is generally sufficient to maintain the retainer ring 140 and the bladder 1140 supported by the retainer ring 140 in place within the interior cavity 106 of the cap body 104 prior to and during assembly of the cap-bladder assembly 100 on the distal end 32 of the cylindrical body 30. In particular, the illustrated radial flange 142 is segmented and includes a series of elongated tabs 148 that define the outer diameter of the radial flange 142 which frictionally engages the interior of the sidewall 116 to maintain the retainer ring 140 and the bladder 1140 supported by the retainer ring 140 in place within the interior cavity 106 of the cap body 104 prior to and during assembly of the cap-bladder assembly 100 on the distal end 32 of the cylindrical body 30. Between the tabs 148, a series of recesses 150 is provided to interengage with the one or more axially-extending tabs 128 on the cylindrical portion 114 of the cap body 104 to prevent rotation of the retainer ring 140 in the interior cavity 106. The foregoing interengaging feature between the retainer ring 140 and the cap body 104 serves to at least partially isolate the bladder 1140 from torque applied to the cap 102 when the cap-bladder assembly 100 is secured to the cylindrical body 30. The engagement of axially-extending tabs 128 with the recesses 150 also helps to frictionally hold the retainer ring 140 in place within the cap 102. Additionally, it may be desirable to stake-over the edges, for example by ultrasonic or via cold or hot-staking processes, of the axially extending tabs 128 once the retainer ring 140 is installed in the cap 102 to retain the retainer ring 140 therein. The retainer ring 140 may be formed of rigid or semi-rigid material, such as polypropylene, which is also naturally lubricious which reduces friction between the retainer ring 140 and the cap body 104 during assembly.

The foregoing seal arrangement between the bladder 1140 and cap 102 is external and radially outward from the operating bore 37 of the cylindrical body 30 wherein the plunger element 50 is operable. As such, a nearly seamless joint is present between the taper rim 45 of the cylindrical body 30 and the inner diameter of the retainer ring 140 which the plunger element 50 can ride over with little resistance as the outer rib 1142 sandwiched between the cap body 104 and the cylindrical body 30 to help form the seamless joint.

In addition to the foregoing configuration of the retainer ring 140 which is simply press-fit into the cap 102, the retainer ring 140 may be configured to be threaded into the interior cavity 106 of the cap body 104. Alternatively, the retainer ring 140 may be designed to "float" once assembled into the cap body 104 for tolerance control. Additionally, the bladder 1140 may also be over-molded to retainer ring 140 and assembled to the cap body 104 as described above, or the bladder 1140 could be over-molded directly to the cap body 104 and the retainer ring 140 would no longer be necessary. Several molding techniques for forming the cap body 104, retainer ring 140, and bladder 1140 are described further herein. The interior cavity 106 of the cap body 104 can include undercut tabs (not shown) to help retain the retainer ring 140 therein.

Figure 10A:
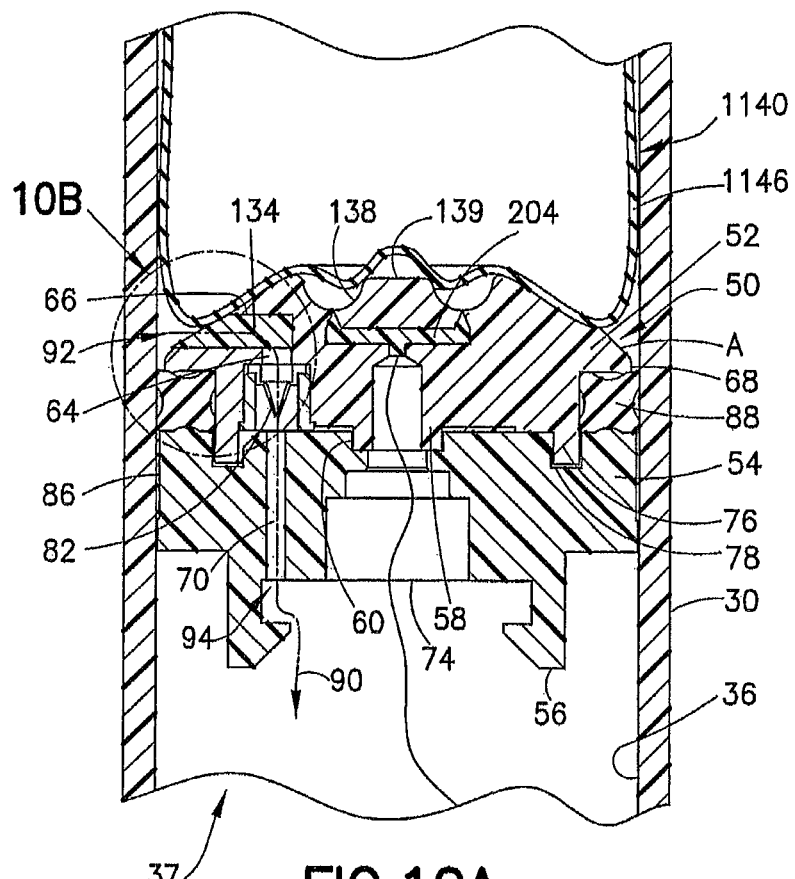
FIG. 10A is a partial cross-sectional view of the bladder syringe of FIGS. 1A-1B showing another embodiment of the plunger element and the interaction between the bladder and the plunger element during movement of the plunger element.
Figure 10B:
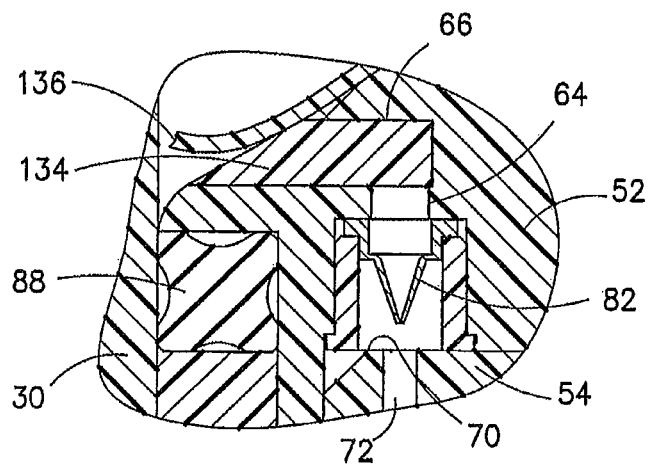
FIG. 10B is a detail view of Detail 10B in FIG. 10A.

Referring next to FIGS. 10A-10B and 11A-11D, another and presently preferred embodiment of the plunger element 50 is shown disposed in the bore 37 of the cylindrical body 30. The plunger element 50 shares most of the features of the embodiments of the plunger element 50 described previously, and generally comprises one vent path 90 through the plunger element 50 in a similar manner to that shown in FIGS. 8-9. Only relevant differences over the previous embodiments of the plunger element 50 will now be described herein. In the presently preferred embodiment of the plunger element 50, the plunger element 50 comprises a distal portion 52 and a proximal portion 54, with the seal ring 88 disposed in a recess defined at the interface between the distal portion 52 and the proximal portion 54. The radial passageway 66 in the distal portion 52 supports a porous plug 134 that is typically made of porous plastic like Porex®. As depicted, the radial passageway 66 is provided in the distal portion 52 of the plunger element 50 on the same side as the bladder 1140. Typically, the radial passageway 66 is provided so that the inlet port 92 of the vent path 90 and, hence, to the porous plug 134, is located near the outer edge of the distal portion 52 of the plunger element 50. In the depicted embodiment, this entrance location is on the tapering portion of the distal portion 52 of the plunger element 50. This embodiment may optionally include a protective flap or cover 136, as shown in FIG. 10B, to prevent the bladder 1140 from extruding into the inlet port 92. The protective flap or cover 136 opens and closes depending fluid pressure within the cylindrical body 30. The location of the porous plug 134 is important for proper air purge during filling of the bladder 1140 because the bladder 1140 eventually seals the inlet port 92 of the porous plug 134 during fluid filling preventing air from passing through the vent path 90. Thus, it is desirable to locate the inlet port 92 leading to the porous plug 134 near the outer edge or circumference of the distal portion 52 of the plunger element 50 on the same side as the bladder 1140 for proper venting of the airspace above the plunger element 50. The present embodiment of the plunger element 50 also has a distal portion 52 comprising a distal circular recess 138 that surrounds a flat nub or ledge 139. This particular configuration has been found to work well with the bladder 1140 shown, for example, in FIG. 6 having a membrane portion 1146 with a W-shaped convoluted central well portion 1148 because the interaction between the distal circular recess 138 and ledge 139 and the extra material present in the W-shaped convoluted central well portion 1148 maintains the bladder material aligned in the cylindrical body 30 during expansion/elongation of the bladder 1140 and thereby enables greater stretching or filling of the bladder 1140. In any of the embodiments of the plunger element 50 and cylindrical body 30, it is desirable to form the cylindrical body 30 of a material with a low coefficient of friction to allow for easier release of bladder 1140 and reduce the possibility of having the bladder 1140 pinch under the seal ring 88. Furthermore, while a passive porous plug 134 with optional flap or cover 136 is described in the foregoing, this arrangement may be replaced by a controlled vent such as an electromechanical device that is actively controlled by a controller associated with the fluid injector 12 to open and close the vent path 90 as desired and at appropriate times to fill and dispense fluid from the bladder syringe 20. The two halves 52, 54 of the plunger element 50 may be designed and assembled to compress the seal ring 88 and limit potential pinching of the bladder 1140. For example, features may be provided to either half 52, 54 to control the amount and location of seal compression.

Figure 11A:
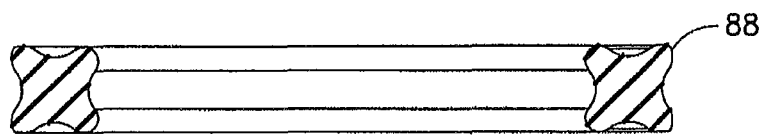
FIGS. 11A-11E are cross-sectional views of various sealing elements for the various embodiments of the plunger element for the bladder syringe of FIGS. 1A-1B.
Figure 11B:
Figure 11C:
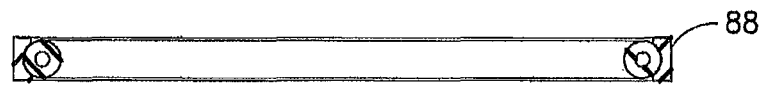
Figure 11D:
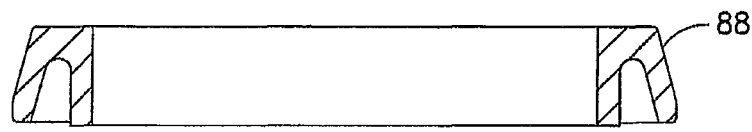
Figure 11E:
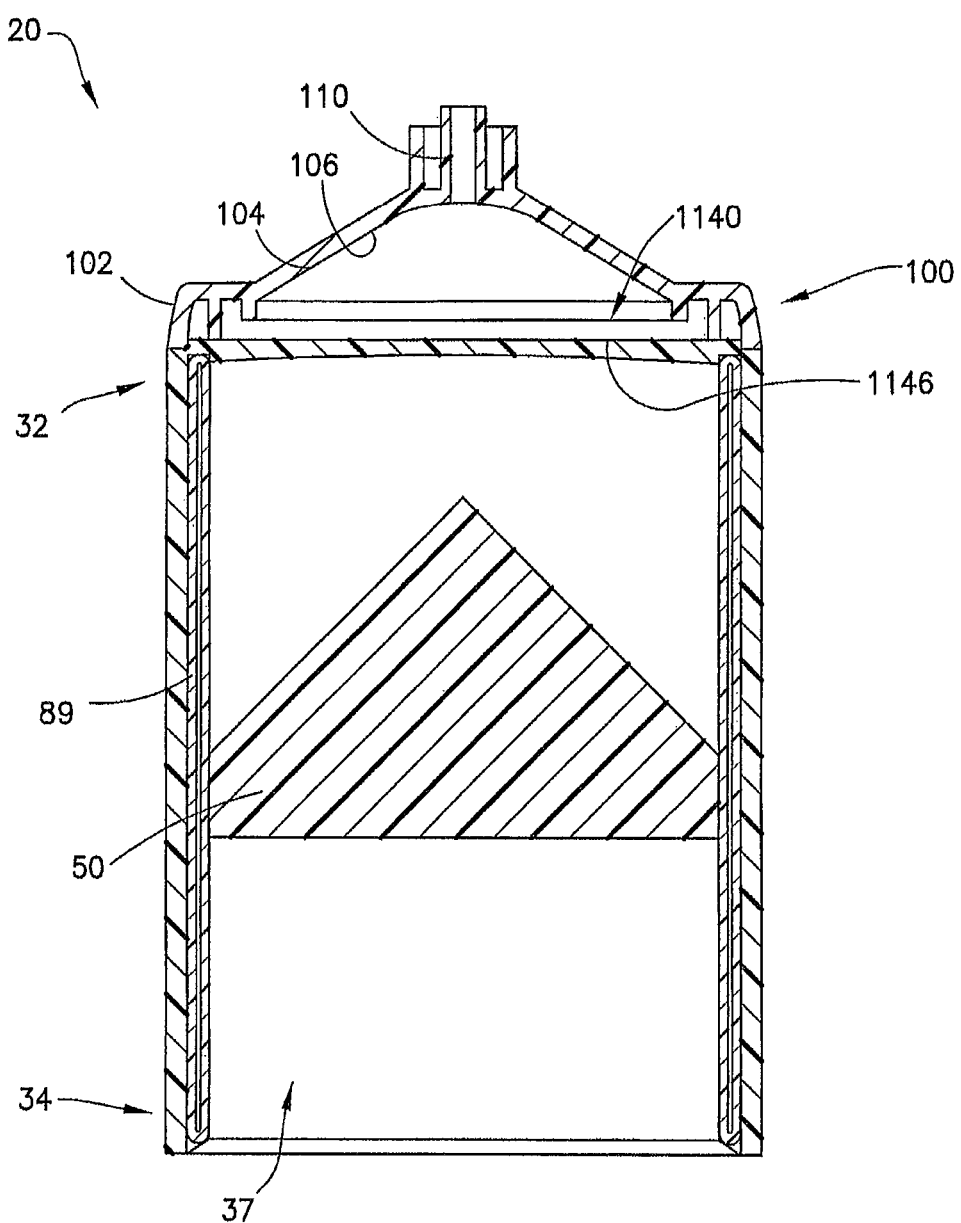

Additionally, FIGS. 11A-11D illustrate various different embodiments of the seal ring 88 that may be used with the plunger element 50 in any of the embodiments of this disclosure. As is well-known, dynamic seals increase the force applied to a syringe wall as pressure increases. FIG. 11A shows a suitable quad seal as the seal ring 88 and FIG. 11D shows a dynamic U-cup seal as the seal ring 88. Dynamic type seals may help keep the bladder 1140 from extruding past the seal ring 88 at higher pressure and speeds of the piston element 14 of the fluid injector 12. As the seal ring 88 is used to seal the vacuum in the cylindrical body 30, the dynamic seal ring 88 as shown in FIG. 11D is designed to increase the sealing pressure against the interior wall 36 of the cylindrical body 30. FIG. 11C illustrates another embodiment of a seal ring 88 in the form of an O-ring energized cap seal and FIG. 11B illustrates an O-ring seal ring 88 as described previously. The seal ring 88 and guide ring 84 may be made of internally lubricated seal materials, Teflon® and the like, or low friction coatings may be provided on these seals or on the interior wall 36 of the cylindrical body 30 to reduce friction and increase the life of the seals. Proper lubrication of the seals 84, 88 is desirable to prevent the bladder 1140 from "extruding" past the seal. Additionally, silicone may be applied to the distal portion 52 of the plunger element 50 and/or provided on the proximal side 1152 of the membrane portion 1146 of each bladder 1140 during manufacturing to maintain lubrication on the interior wall 36 of the cylindrical body 30 for maintenance of the seals 84, 88 as well as lower the friction between the bladder 1140 and the interior wall 36. Further, the seals 84, 88 may be anti-extrusion seals made from hydrophobic material wherein air can pass through to vent air from behind bladder 1140, but if fluid contacts these seals the pathway becomes obstructed preventing fluid from reaching the interior of the plunger element 50 and the check valves 82 therein. Furthermore, one or both of the seals 84, 88 may be moisture sensitive so that in case of a leak or rupture of the bladder 1140 during use, one or both seals 84, 88 expand and inhibit or prevent movement of the plunger element 50. As an alternative to the seal arrangements shown in FIGS. 11A-11D, as shown in FIG. 11E, cylindrical seal 89 may be seated in the bore 37 of the cylindrical body 30 that slides or rolls as the plunger element 50 moves within the bore 37. The cap-bladder assembly 100, cylindrical body 30, and the plunger element 50 are shown schematically in FIG. 11E for simplicity and details of these components and their interaction may be found in the foregoing.

Moreover, it is also desirable to coat the proximal side 1152 of the bladder 1140 with a lubricant that may be transferred to the interior wall 36 of the cylindrical body 30 during filling. This coating may alternatively be an antibiotic/antibacterial coating that may also be lubricant based and with each expansion of the bladder 1140 to the interior wall 36 of the cylindrical body 30, the lubricant coating, antibiotic or antibacterial coating, or lubricant-based antibiotic coating is transferred to the interior wall 36 and this coating is further transferred to the plunger element 50, which likewise may be independently coated with an antibiotic or antibacterial coating, or lubricant-based antibiotic coating. Furthermore, the distal and proximal portions 52, 54 of the plunger element 50, cylindrical body 30, and/or bladder 1140 may be molded from antibiotic materials for sterility enhancement.

In general, it is desirable to provide the cap-bladder assembly 100 in prepackaged form, such as sealed in a sterile state within a packaging container. Such a prepackaged form can maintain the sterility of the cap-bladder assembly 100 until the packaging is opened and the cap-bladder assembly 100 is removed therefrom. Several different packaging embodiments for the cap-bladder assembly 100 are described later in this disclosure. However, it is generally desirable that the cap-bladder assembly 100 arrive for use at a medical facility with the bladder 1140 secured in place by the retainer ring 140 within the interior cavity 106 of the cap body 104 in the manner described in the preceding paragraphs. As a result, the medical practitioner at the medical facility only needs to open the packaging, remove the cap-bladder assembly 100 therefrom, and mate the cap-bladder assembly 100 with the cylindrical body 30 as now described hereafter.

In a typical fluid injection procedure involving the fluid delivery system 10, the fluid injector 12 is usually prepositioned within a medical imaging suite of a hospital or other medical facility and may be permanently affixed somewhere within the imaging suite. The medical practitioner may perform several preparatory steps to prepare the fluid injector 12 for a fluid injection procedure, such as setting up and programming the controller of the fluid injector 12 for the specified fluid injection procedure. At least one of these preparatory steps ideally includes mounting the proximal end 34 of the cylindrical body 30 to the fluid injector 12 by whatever mounting procedure is required to mate the cylindrical body 30 to the fluid injector 12. If the fluid injector 12 is a two-syringe injector, two cylindrical bodies 30 will be connected to the fluid injector 12. As noted previously, the cylindrical body 30 may be reusable at least to a limited degree by number of fluid injections and/or patients. The cylindrical body 30 with plunger element 50 and mounting ring 22 may be prepackaged in their own container and one of the preparatory steps will include opening the prepackaged container and removing one or more cylindrical bodies 30 therefrom. If desired, the piston elements 14 of the fluid injector 12 may be moved to a fully extended position.

Thereafter, the cap-bladder assembly 100 may be secured to the distal end 32 of the cylindrical body 30. This is generally accomplished by first placing the split mounting ring 22 in engagement with mounting collar 42 on the distal end 32 of the cylindrical body 30. Then, the cap-bladder assembly 100 may be removed from its packaging and the cylindrical portion 114 of the cap body 104 may be placed over the end flange 44 on the distal end 32 of the cylindrical body 30. The tapered rim 45 on the end flange 44 facilitates the placement of the cylindrical portion 114 over the distal end 32 of the cylindrical body 30. Once the one or more exterior radial tabs or threads 122 on the cylindrical portion 114 of the cap body 104 begin to interface with the corresponding interior tabs or threads 28 in the mounting ring 22, the cap body 104 may then be rotated or otherwise manipulated to complete the engagement between the mating sets of tabs or threads 28, 122. An end feature, such as a tab or rib, on the exterior threads 122 on the cap body 104 contacts a corresponding feature, such as a tab or rib, on the engaging threads 28 within the mounting ring 22 to prevent further rotation of the cap 102 relative to the mounting ring 22. At this point, the rim or end 130 on the cap body 104 may be in an axial position where the proximal rim or end 130 seats against the mounting collar 42 on the cylindrical body 30. Additionally, the tapered inner rim 146 in the retainer ring 140 seats in engagement with tapered rim 45 on the end flange 44 at the distal end 32 of the cylindrical body 30. A generally fluid-tight or leak proof seal is provided by the O-ring 48 disposed between the cylindrical portion 114 of the cap body 104 and the distal end 32 of the cylindrical body 30, with the threaded engagement provided by mating threads 28, 122 compressing the O-ring 48 between the cylindrical portion 114 of the cap body 104 and the distal end 32 of the cylindrical body 30 for a fluid-tight engagement. The engagement of the tapered inner rim 146 in the retainer ring 140 with the tapered rim 45 on the end flange 44 at the distal end 32 of the cylindrical body 30 traps the outer rib 1142 of the bladder 1140 axially within the circumferential recess or groove 126 defined between the annular rib or rim 124 and the sidewall 116 of the proximal cylindrical portion 114 of the cap body 104. The exterior finger flanges 120 allow for easy handling of the cap body 104 during the assembly of the cap 102 with the cylindrical body 30. In the present embodiment, alignment between the mating sets of tabs or threads 28, 122 is not required before rotation of the cap body 104 begins.

A disposable fluid set 200, as shown in FIG. 1A, may be associated with the bladder syringe 20 by joining this set 200 to the threaded end connector 112 at the end of the discharge conduit 110 of the cap body 104. Alternatively, the disposable fluid set 200 may be provided as an integral part of the discharge conduit 110 of the cap body 104. The disposable fluid set 200 may include one or more tubing elements 201 terminating in a container spike or another medical connector element 202 for placing the bladder syringe 20 in fluid communication with one or more bottles or bags containing desired injection fluids. The cap body 104 may comprise a pinch valve or block 203, which is formed as part of one of the finger flanges 120 in FIG. 1A, for pinching the tubing element 201 and preventing unwanted outflow from the bladder syringe 20. The pinch valve or block 203 may simply be provided as a tube holder.

In the foregoing description, the cap-bladder assembly 100 attaches to the cylindrical body 30 by a screw thread engagement and this engagement may feature a multiple start thread to reduce rotation required for assembly of the cap-bladder assembly 100 to the cylindrical body 30. This thread geometry also reduces the rotation required for complete assembly. However, this threaded connection may be equivalently replaced by a bayonet connection similar to that provided by attachment flanges 40 on the cylindrical body 30 that mate with the injector housing 18 of the fluid injector 12. In the foregoing description, the mounting ring 22 is formed from two identical pieces to form a clamshell around the cylindrical body 30. These two half-ring portions 24 may alternatively be secured together around the cylindrical body 30 with screws, as noted previously. The two half-ring portions 24 could also be secured to the cylindrical body 30 using a press fit (as noted previously), ultrasonic welding, heat staking, or through the use of adhesives. The clamshell configuration of the two half-ring portions 24 may also contain features which provide visual, tactile, and audible feedback to the user when the cap-bladder assembly 100 is fully engaged on the cylindrical body 30.

Once the cap-bladder assembly 100 is fully engaged on the cylindrical body 30, fluid filling and air purging operations involving the bladder syringe 20 may be conducted. Such fluid filling and air purging operations involve filling the bladder 1140 with a desired injection fluid and purging of air from behind the filled bladder 1140. Once all of the desired fluid supplies are associated with the disposable fluid set 200 connected to the bladder syringe 20, a filling sequence may be initiated by an operator. The filling sequence fills the bladder 1140 and the supply lines of the disposable fluid set 200 and this sequence may be done manually or automatically based on the programming of the fluid injector 12. In the automatic mode, volume indicators on the fluid injector head 12 will indicate how much fluid needs to be loaded to support the injection protocol including the amount of fluid necessary to air-purge and prime the tubing associated with the disposable fluid set 200. When a Fill button (not shown) is pressed on the fluid injector 12, the fluid injector 12 automatically retracts the piston elements 14 to draw in a predetermined amount of injection fluid. The piston elements 14 then stop and advance to expel any air that was drawn into the bladder 1140. The piston elements 14 then automatically retract again until the volume required to perform the injection is loaded into the bladder 1140 plus an additional amount of fluid, such as 10 ml, as an example. The piston elements 14 then pause for a short period of time, for example 5 seconds, to ensure all fluid is drawn into the bladder 1140 then advance to the final volume. The fluid injection procedure may then be initiated by the attendant operator by pressing a Start button (not shown) on the fluid injector 12. Ideally, the fluid injector 12 automatically performs an air check for air in the tubing of the disposable fluid set 200 and/or the bladder syringe 20 either in preparation for the fluid injection procedure or during the fluid injection procedure or in both instances. Once the fluid injection procedure is completed, the cap-bladder assembly 100 may be removed from the cylindrical body 30 and discarded. The cylindrical body 30 may remain in place and be reused or may be replaced as desired by attendant medical personnel. The foregoing filling and air purging operations may be done manually in that an attendant operator for the fluid injector 12 may conduct the steps in sequence rather than relying on the programming provided in the controller associated with the fluid injector 12. The fluid injector 12 may have a weight sensor (not shown) in the fluid injector housing 18 that can detect an increase in weight of one or both of the bladder syringes 20 shown in FIG. 7, indicating that fluid is present in one or both of the bladders 1140 of the bladder syringes 20. The weight sensor may further include a measurement device to determine gross air present in the bladder syringe(s) 20 versus a fully liquid-filled syringe(s) 20.

Referring to FIGS. 8-9, it is desirable for the plunger element 50 to work in conjunction with the bladder 1140 to maximize fill volume. When the bladder 1140 contacts the interior wall 36 of the cylindrical body 30 during filling when the plunger element 50 moves in the direction of arrow $A_2$, the vacuum behind the bladder 1140 can restrain the bladder 1140 against the interior wall 36 of the cylindrical body 30 forcing further expansion of the bladder 1140 to come from material that is not currently in contact with the interior wall 36, (e.g., from the center of the membrane portion 1146). The plunger element 50 may interact with the bladder 1140 to restrict movement of the bladder 1140 outward towards the interior wall 36 of the cylindrical body 30, which conserves the bladder material (e.g., thickness) in the center of the membrane portion 1146 as the plunger element 50 is retracted in the cylindrical body 30 in the direction of arrow $A_2$ and the bladder 1140 expands. Accordingly, those embodiments of the bladder 1140 to be discussed herein that comprise extra material or features on the membrane portion 1146 as shown, for example, in FIGS. 12-13 and 15-21, as non-limiting examples, allow for increased or enhanced fill volumes. Several design features built into the plunger element 50 and/or bladder 1140 can increase adhesion of the bladder 1140 to the distal portion 52 of the plunger element 50. These design features include, as above, a thicker section in the center of the membrane portion 1146 of the bladder 1140 or additional material through addition of convolutes (e.g., additional curves/curvature of the membrane portion 1146), a steeper angle of taper for the distal portion 52 of the plunger element 50, or a plunger tip or point 98 with a steep angle to increase surface area in contact with the bladder 1140. An increase in the coefficient of friction between the bladder 1140 and distal portion 52 of the plunger element 50 may also increase fill volumes. This increase in the coefficient of friction may be accomplished, for example, through material selection and/or interengaging surface features such as surface texturing on the distal portion 52 of the plunger element 50 and the membrane portion 1146 of the bladder 1140 such as interlocking steps, ribs, or grooves on the membrane portion 1146 and the distal portion 52 of the plunger element 50, as discussed herein in connection with FIGS. 35A-35B. Further, as noted previously, the plunger element 50 with a distal portion 52 having a distal circular recess 138 that surrounds a flat nub or ledge 139 has been found to work particularly effectively with the bladder 1140 shown, for example, in FIG. 6 having a membrane portion 1146 with a W-shaped convoluted central well portion 1148.

As also noted previously, the vent path 90 through the plunger element 50 controls the flow of air and liquid in and out of the bladder syringe 20. In FIGS. 8-9, retraction of the plunger element 50 in the bladder syringe 20 creates a vacuum which expands the bladder 1140 to fill the bladder 1140 with fluid. Advancement of the plunger element 50 dispenses fluid from the filled bladder 1140. Proper filling of the bladder syringe 20 requires a high vacuum level behind the bladder 1140 in the space in the cylindrical body 30 between the plunger element 50 and the bladder 1140. To start the fluid fill process, it is desirable that there be as little air behind the bladder 1140 as possible in order to generate a high vacuum. The one-way check valves 82 in the plunger element 50 facilitate removal of air behind the bladder 1140. As shown in FIG. 8, as the plunger element 50 is advanced in the direction of arrow $A_1$ toward the bladder 1140 in preparation for filling, the singular check valve 82 in this embodiment allows air to escape from behind the bladder 1140. As noted previously, duckbill check valves are examples of one-way check valves that could be used in the plunger element 50. Duckbill check valves offer the advantage of a self-cleaning sealing surface as well as a built-in flange for sealing the path around the valve. Reverse or proximal movement of the plunger element 50 in the direction of arrow $A_2$ in FIG. 9 creates a vacuum in this space. This vacuum pressure acts upon the cap-bladder assembly 100 to fill the bladder 1140 of this assembly 100 with a desired injection fluid. Once filled with a desired amount of injection fluid, subsequent forward or distal operation of the piston element 14 of the fluid injector 12 in the direction of arrow $A_1$ in FIG. 8 causes the injection fluid to be dispensed from the cap-bladder assembly 100.

Referring next to FIGS. 12-46, various embodiments and variations of the bladder syringe 20 are shown, as are numerous embodiments of the bladder 1140 that are suitable for use in the cap-bladder assembly 100. While various embodiments and variations of the bladder syringe 20 along with numerous embodiments of the bladder 1140 suitable for use in the cap-bladder assembly 100 are illustrated in FIGS. 12-46, these are not to be considered exhaustive and other configurations are possible within the scope and teachings of this disclosure. FIGS. 12-13 show the embodiment of the bladder 1140 described previously wherein the membrane portion 1146 includes a generally W-shaped central well portion 1148 defined by a series of "convolutes" "C" or arcuate sections. The membrane portion 1146 has a generally consistent or uniform cross-section and the central well portion 1148 generally defines an overall "W" shape. FIG.

Figure 12A:
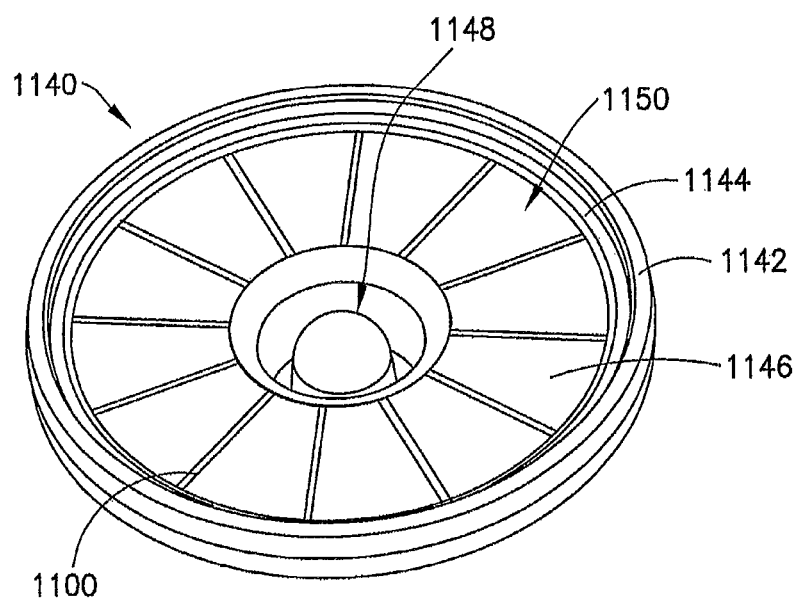
FIGS. 12A-12B are respective perspective and cross-sectional views of a first embodiment of the bladder for the cap-bladder assembly for the bladder syringe of FIGS. 1A-1B.
Figure 12B:
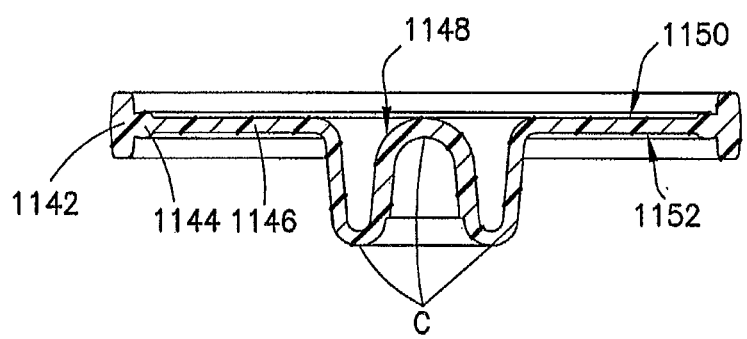
Figure 12C:
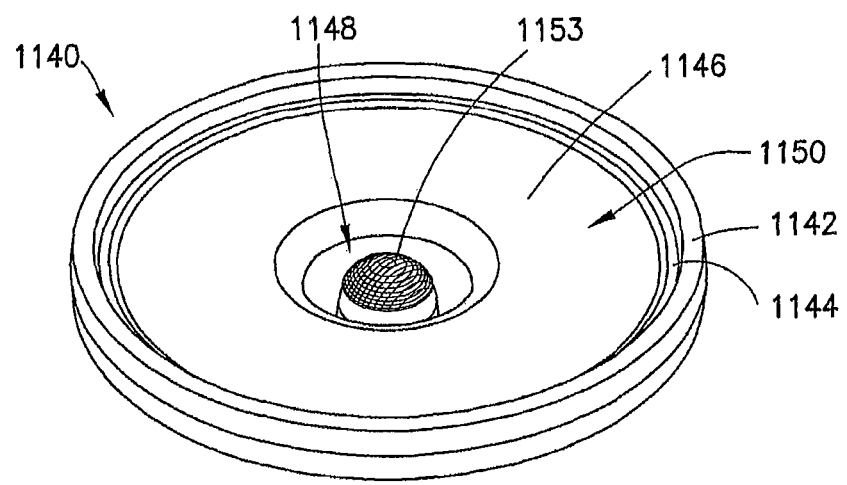
FIGS. 12C-12D are respective perspective and cross-sectional views of a modification of the first bladder embodiment of FIGS. 12A-12B.
Figure 12D:
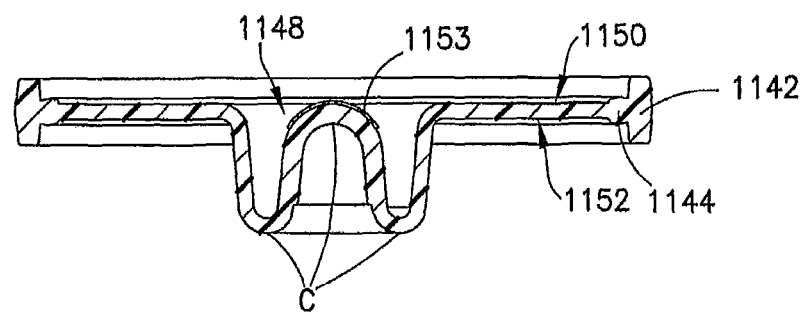
Figure 13A:
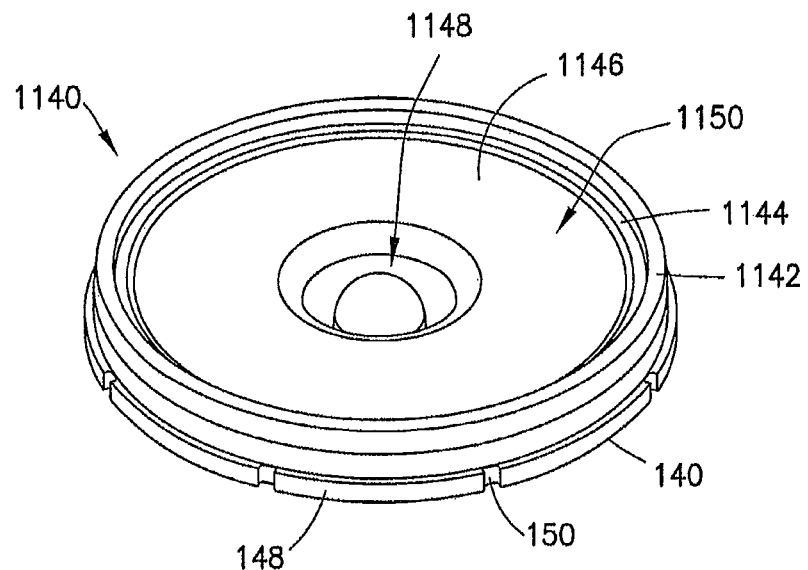
FIGS. 13A-13B are respective perspective and cross-sectional views of the first embodiment of the bladder shown in FIGS. 12A-12B and further showing a retainer ring for holding the bladder in the cap-bladder assembly for the bladder syringe of FIGS. 1A-1B.
Figure 13B:
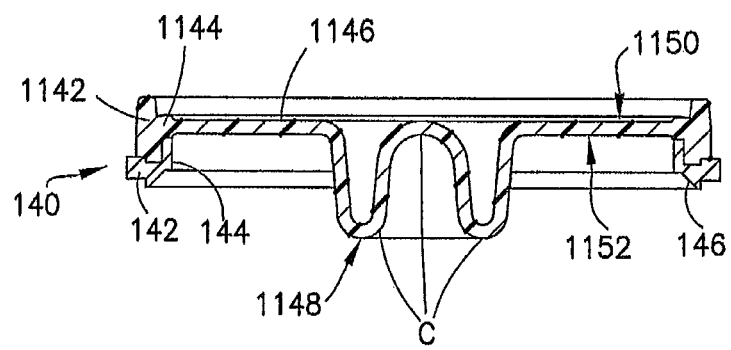

13A-13B shows the bladder 1140 supported by the retainer ring 140 according to the concepts outlined previously. With the convoluted central well portion 1148 in the center of the membrane portion 1146 more material is available in the inner portion of the membrane portion 1146 when the bladder 1140 is filled, for example, to the 200 ml fill mark. The convolutes of the central well portion 1148 are identified with reference character "C". If desired, an additional convolute (not shown) could be added to the outer edge of the bladder 1140 inward of the outer rib 1142 so that extra material is available near the interior wall 36 of the cylindrical body 30 and delay when the stretching of the bladder 1140 begins. FIG. 12A further shows that the top or distal side 1150 may have lines, grooves, or markings 1100 which provide a visual indication to attendant medical personnel of the bladder 1140 being filled with fluid and in a stretched state. The lines, grooves, or markings 1100 may be radial, circular, or have any suitable orientation to visually alert a user. Such markings 1100 may be applied to any of the embodiments of the bladder 1140 within this disclosure, and may be disposed on the bottom or proximal side 1152 as well. FIGS. 12C-12D show that a reinforcing mesh or screen 1153 may be applied to the innermost convolute C on the top side of the membrane portion 1146 to reinforce this convolute and to interact with the flat nub 139 on the distal portion 52 of the plunger element 50 discussed previously in connection with FIG. 10A. The mesh or screen 1153 reinforces the weakest portion of the bladder 1140 and may be cotton fabric, aramid fiber, polyester fiber, and other similar materials, and may also be stiffer material, like TPE, over-molded onto the innermost convolute C.

Figure 14A:
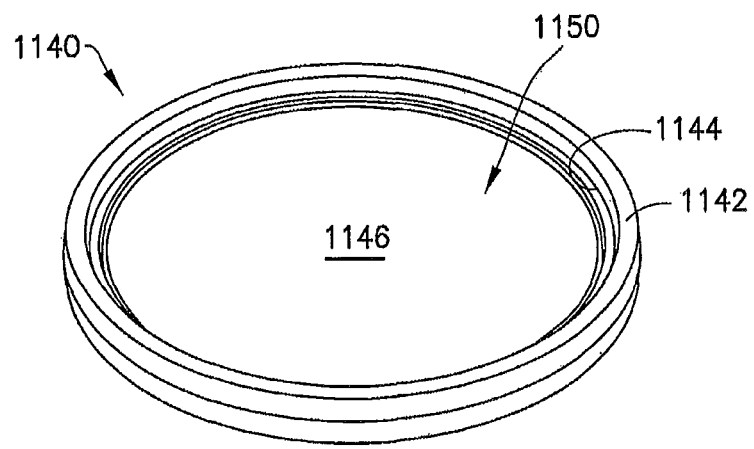
FIGS. 14A-14B are respective perspective and cross-sectional views of a second embodiment of the bladder for the cap-bladder assembly for the bladder syringe of FIGS. 1A-1B.
Figure 14B:
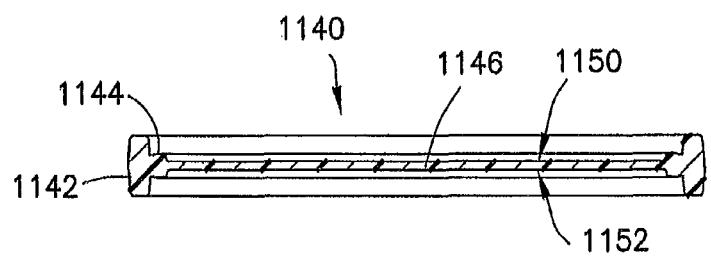

FIGS. 14A-14B show an embodiment of the bladder 1140 that has a membrane portion 1146 that is substantially flat or planar and, thus, this embodiment of the bladder 1140 is non-orientation specific. This embodiment is akin to a flat trampoline and may have the advantage of being installed over a plunger element 50 disposed near or projecting from the distal end 32 of the cylindrical body 30 so that it protrudes from the cylindrical body 30. In this configuration, the bladder 1140 may be placed over the distal portion 52 of the plunger element 50 so that the center or tip of the plunger element 50 would contact the bladder 1140 first as the bladder 1140 is installed and, thereby, air is forced out from between the plunger element 50 and the bladder 1140, which could negate the need for the check valves 82 in the plunger element 50.

Figure 15A:
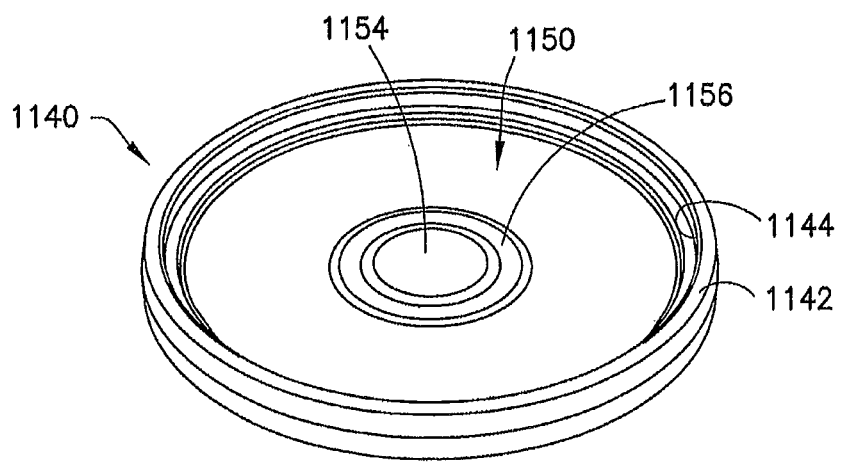
FIGS. 15A-15B are respective perspective and cross-sectional views of a third embodiment of the bladder for the cap-bladder assembly for the bladder syringe of FIGS. 1A-1B.
Figure 15B:
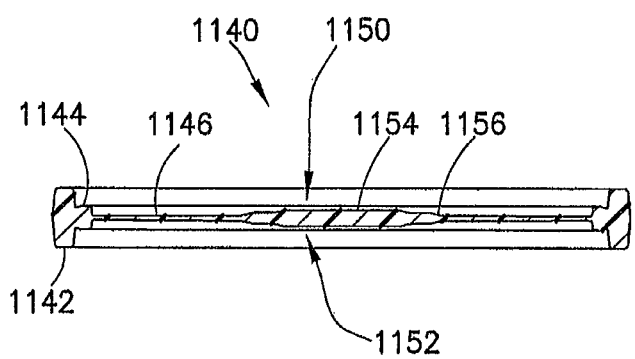

FIGS. 15A-15B shows an embodiment of the bladder 1140 wherein the membrane portion 1146 has a centrally-located solid disc 1154 stacked on and a second solid disc 1156 each disposed centrally on the membrane portion 1146. One or both of the top or distal side 1150 and the bottom or proximal side 1152 of the membrane portion 1146 may have the foregoing solid discs 1154, 1156. Due to the presence of the solid discs 1154, 1156, it will be appreciated that the membrane portion 1146 exhibits a non-uniform cross-section in this embodiment. In this embodiment, there is thicker material in the center of the bladder 1140, particularly the inner one-third (⅓) of the membrane portion 1146. In use, this inner one-third area formed by the solid discs 1154, 1156 is stretched very thin because the outer two-thirds is "vacuumed" to the interior wall 36 of the cylindrical body 30 and contributes little to the stretch. A thicker wall section in the inner one-third area, as present in this embodiment, provides a bladder 1140 with less stress at higher fill volumes and able to deliver fluid under high pressure.

Figure 16A:
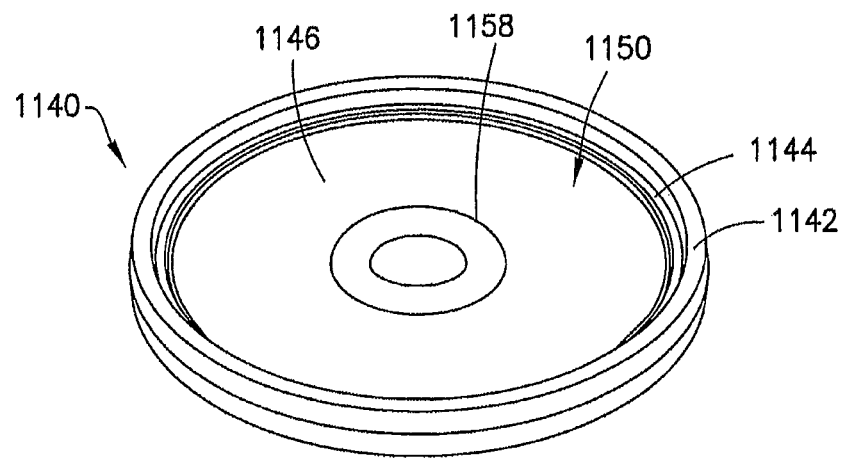
FIGS. 16A-16B are respective perspective and cross-sectional views of a fourth embodiment of the bladder for the cap-bladder assembly for the bladder syringe of FIGS. 1A-1B.
Figure 16B:
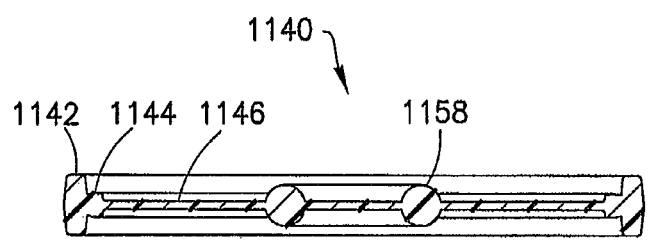

FIGS. 16A-16B show an embodiment of the bladder 1140 with a membrane portion 1146 having a centrally-located solid ring 1158. One or both of the top or distal side 1150 and the bottom or proximal side 1152 of the membrane portion 1146 may have the foregoing solid ring 1158. Due to the presence of the solid ring 1158, it will be appreciated that the membrane portion 1146 exhibits a non-uniform cross-section in this embodiment. In this embodiment, the annular solid ring 1158 in the center of the bladder 1140 contributes to the stretching and filling of the bladder 1140. The embodiment of FIGS. 16A-16B is one of several embodiments in this disclosure that comprise additional material in the center area of the membrane portion 1146 so that, for example, there is an interaction between the distal circular recess 138 and ledge 139 of the plunger element 50 in FIGS. 10A-10B to maintain the bladder material aligned in the cylindrical body 30 during expansion/elongation of the bladder 1140 and thereby enables greater stretching or filling of the bladder 1140; any of the embodiments of the bladder 1140 having extra center material may have this interaction feature.

Figure 17A:
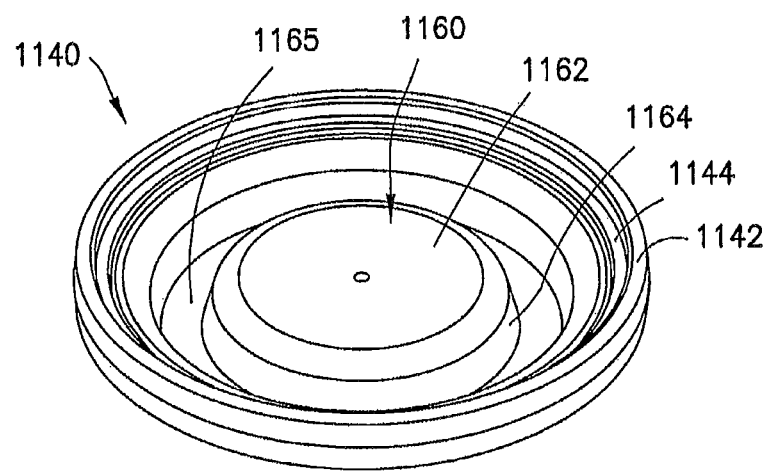
FIGS. 17A-17B are respective perspective and cross-sectional views of a fifth embodiment of the bladder for the cap-bladder assembly for the bladder syringe of FIGS. 1A-1B.
Figure 17B:
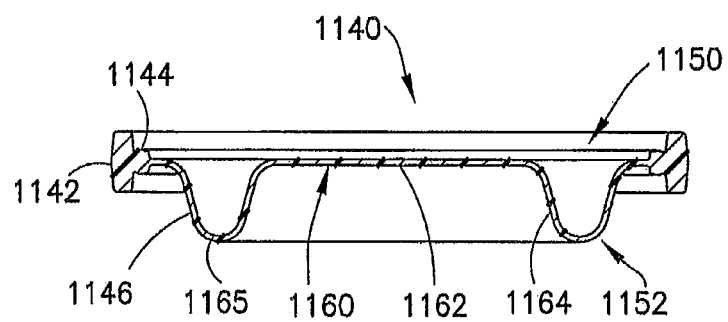

FIGS. 17A-17B illustrate an embodiment of the bladder 1140 having a membrane portion 1146 that includes a W-shaped central well portion 1160. The raised central well portion 1160 has a flat or planar top portion 1162 and a tapering sidewall 1164 leading to an annular outer convolute 1165. The membrane portion 1146 has a generally uniform thickness or cross-section in this embodiment. The "top hat" profile in this embodiment adds material in only one convolute 1165. By adding the convolute 1165 toward the outside radius the area increases quickly by the square of the radius.

Figure 18A:
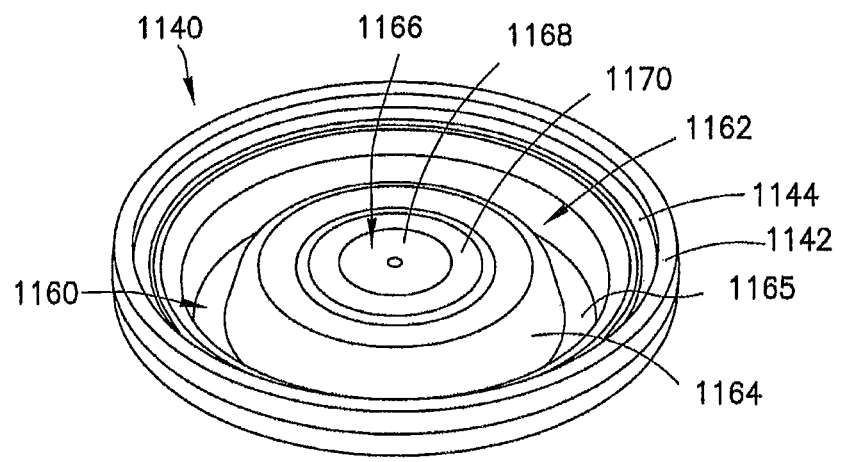
FIGS. 18A-18B are respective perspective and cross-sectional views of a sixth embodiment of the bladder for the cap-bladder assembly for the bladder syringe of FIGS. 1A-1B.
Figure 18B:
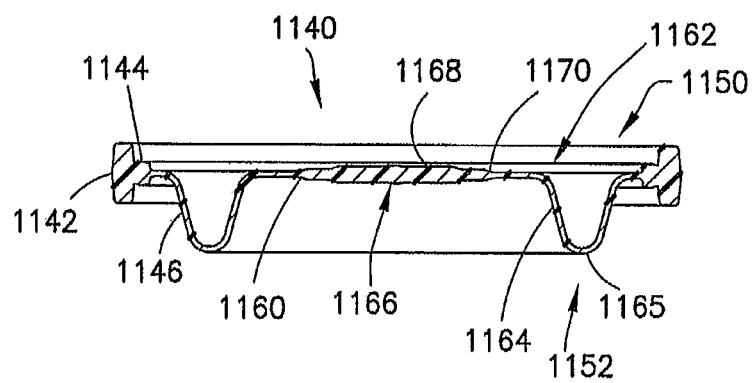

FIGS. 18A-18B illustrate an embodiment of the bladder 1140 having a membrane portion 1146 with a similar W-shaped central well portion 1160 to that shown in FIGS. 17A-17B but further includes a thickened central portion 1166 which may be considered to be formed by two stacked disc portions 1168, 1170 provided on opposing sides 1150, 1152 of the membrane portion 1146. Due to the presence of the thickened central portion 1166, the membrane portion 1146 has a non-uniform cross-section in this embodiment. Extra material in the center of the membrane portion 1146 along with the inclusion of a single outer convolute 1165 provides extra material in the center for dispersion to the interior wall 36 of the cylindrical body 30 and greater fill volumes.

Figure 19A:
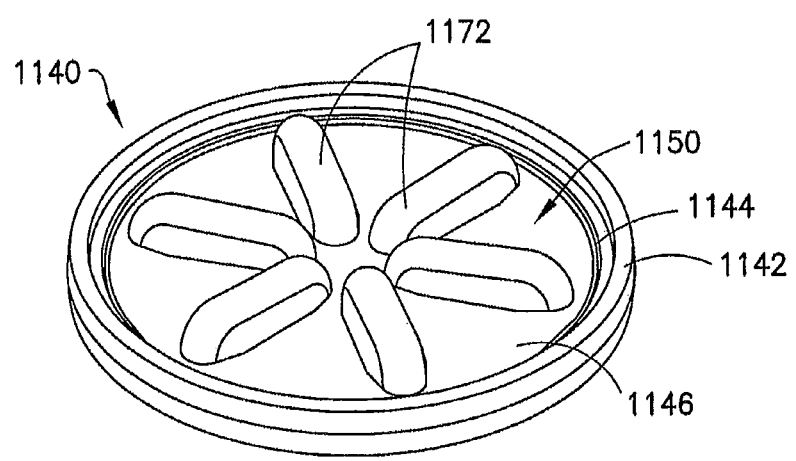
FIGS. 19A-19B are respective perspective and cross-sectional views of a seventh embodiment of the bladder for the cap-bladder assembly for the bladder syringe of FIGS. 1A-1B.
Figure 19B:
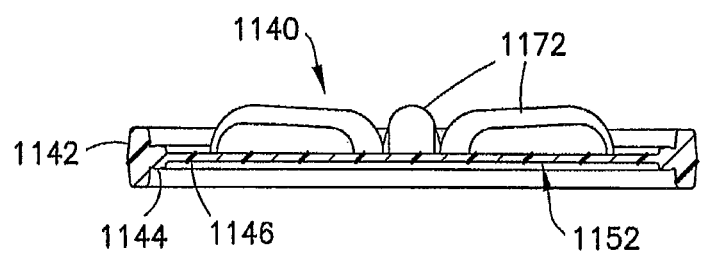

FIGS. 19A-19B illustrate an embodiment of the bladder 1140 having a membrane portion 1146 with a series of radially-directed hollow bulbous portions that define radial convolutes 1172 formed as part of the membrane portion 1146 and which extend upward from the top or distal side 1150 of the membrane portion 1146. The radial convolutes 1172 increase the surface area of the membrane portion 1146 from the center outward. The width of the individual radial convolutes 1172 may be wider as they approach the center of the membrane portion 1146 to provide more material toward the center of the membrane portion 1146.

Figure 20A:
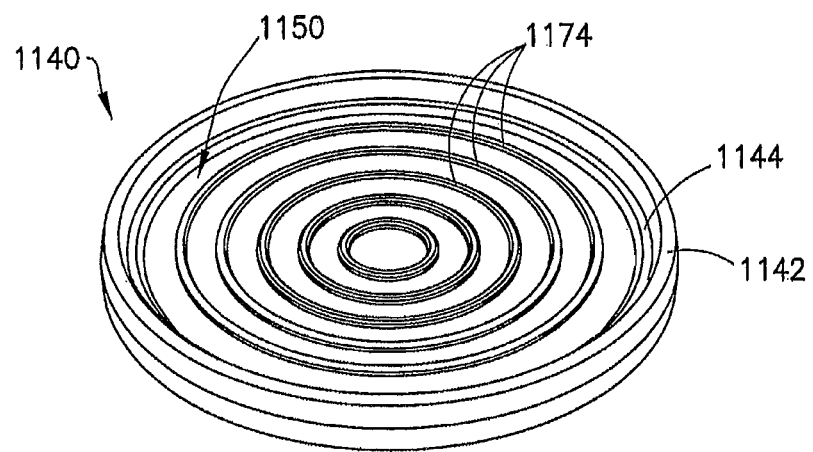
FIGS. 20A-20B are respective perspective and cross-sectional views of a eighth embodiment of the bladder for the cap-bladder assembly for the bladder syringe of FIGS. 1A-1B.
Figure 20B:
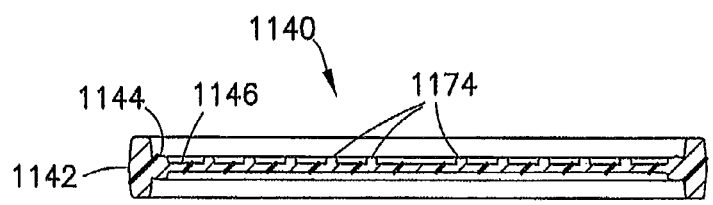

FIGS. 20A-20B illustrate an embodiment of the bladder 1140 having a membrane portion 1146 with a series of concentric friction ribs 1174 formed on the membrane portion 1146. One or both of the top or distal side 1150 and the bottom or proximal side 1152 of the membrane portion 1146 may have the foregoing concentric ribs 1174. Due to the presence of the concentric ribs 1174 on the membrane portion 1146, the membrane portion 1146 has a non-uniform cross-section in this embodiment. The friction ribs 1174 resist sliding down the plunger element 50 and increase friction to slow expansion of the bladder 1140 along the plunger element 50 and retain the thickness of the membrane portion 1146 for a longer period of time during expansion. If the concentric friction ribs 1174 are formed on the bottom or proximal side 1152 of the membrane portion 1146, the distal portion 52 of the plunger element 50 may have opposing annular grooves to engage or interact with the concentric friction ribs 1174.

Figure 21A:
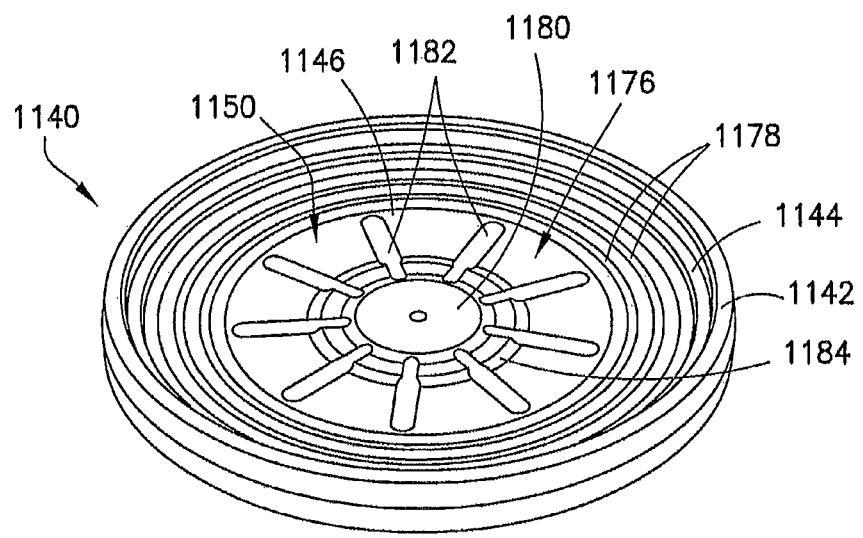
FIGS. 21A-21B are respective perspective and cross-sectional views of a ninth embodiment of the bladder for the cap-bladder assembly for the bladder syringe of FIGS. 1A-1B.
Figure 21B:
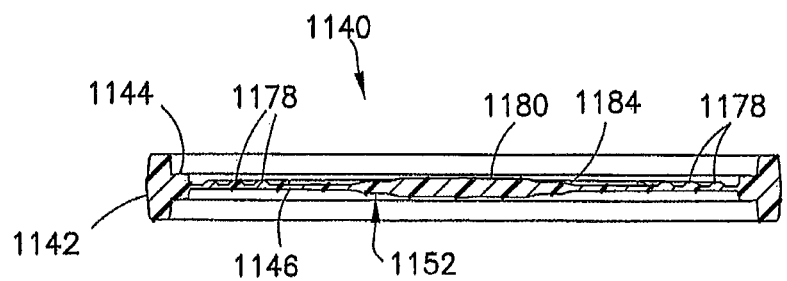

FIGS. 21A-21B illustrate an embodiment of the bladder 1140 in which the membrane portion 1146 has a central "wagon wheel" formation 1176 surrounded by outer concentric solid rings 1178. The wagon wheel formation 1176 includes a central raised disc 1180 and a series of radial spokes or ribs 1182 extending outward from the central raised disc 1180. An inner concentric solid ring 1184 extends concentrically about the central raised disc 1180 to intersect the various radial spokes or ribs 1182. One or both of the top or distal side 1150 and the bottom or proximal side 1152 of the membrane portion 1146 may have the foregoing wagon wheel formation 1176 surrounded by the outer concentric solid rings 1178. The radial ribs 1182 that extend from the center of the membrane portion 1146 add stiffness to the bladder 1140 in this embodiment and retard stretch of material to the interior wall 36 of the cylindrical body 30. Material from the radial ribs 1182 could also be spread out circumferentially to help maintain a minimum thickness of the membrane portion 1146 at extended fill volumes.

FIGS. 22A-22B illustrate an embodiment of the bladder 1140 in which the membrane portion 1146 is folded and twisted like a "Jiffy Pop®" popcorn folded aluminum foil lid The twisted and folded membrane portion 1146 could be on the top side 1150 and/or the bottom side 1152, and by applying a vacuum, the bottom side 1152 could pull down and the top side 1150 expand up. In the present embodiment, the material comprising the bladder 1140 may not have to be resiliently elastic. For simplicity, the details of the outer circumferential rib 1142 and radially-inward extending portion 1144 are omitted in FIGS. 22A-22B.

FIG. 23A-23B illustrate an embodiment of the bladder 1140 having a series of concentric angular-shaped convolutes 1186 in the membrane portion 1146. The use of a series of concentric convolutes 1186, generally triangular-shaped convolutes 1186, increases the surface area of the bladder material. For simplicity, the details of the outer circumferential rib 1142 and radially-inward extending portion 1144 are omitted in FIGS. 23A-23B.

FIGS. 24A-24B illustrate an embodiment of the bladder 1140 in which the membrane portion 1146 is shaped like a flat trampoline with a thinner section 1190 in the center and a thicker outer section 1192 tapering from the thinner center section 1190. The thicker outer section 1192 on the outside of the membrane portion 1146 provides more material for stretching of the bladder 1140 and the thinner inner or center section 1190 creates more stress to cause the thicker outer section 1192 to contribute more to the expansion of the bladder 1140 during operation. For simplicity, the details of the outer circumferential rib 1142 and radially-inward extending portion 1144 are omitted in FIGS. 24A-24B.

Figure 25A:
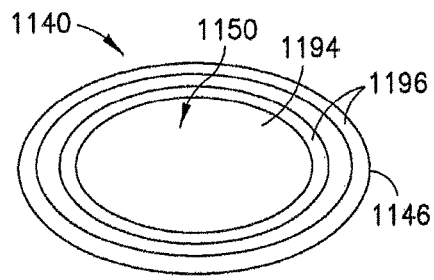
FIGS. 25A-25B are respective perspective and cross-sectional views of a thirteenth embodiment of the bladder for the cap-bladder assembly for the bladder syringe of FIGS. 1A-1B.
Figure 25B:
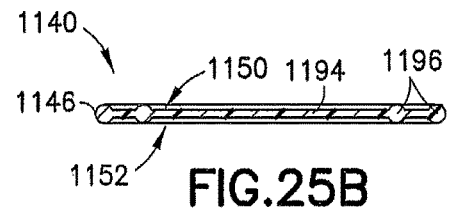
Figure 26A:
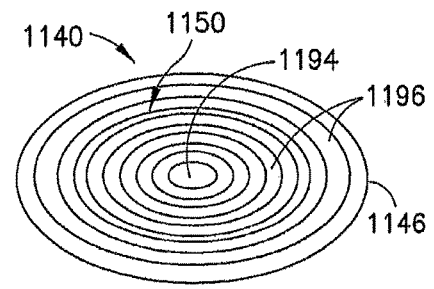
FIGS. 26A-26B are respective perspective and cross-sectional views of a fourteenth embodiment of the bladder for the cap-bladder assembly for the bladder syringe of FIGS. 1A-1B.
Figure 26B:
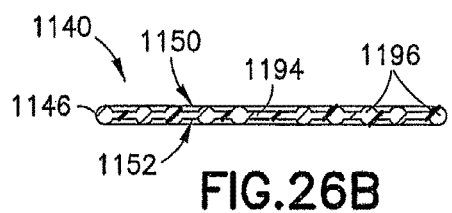

FIG. 25A-25B illustrate an embodiment of the bladder 1140 in which the membrane portion 1146 has a flat trampoline center section 1194 in the center and two outer concentric ribs 1196. The outermost rib 1196 may optionally form the circumferential edge of the bladder 1140 and thus necessitate a change in the shape of the circumferential recess or groove 126 in the cap body 104 which secures the bladder 1140 therein, and a corresponding change in the shape defined by the radial and axial flange 142, 144 of the retainer ring 140. Alternatively, the details of the outer circumferential rib 1142 and radially-inward extending portion 1144 could be included in the membrane portion 1146 of this embodiment, outward from the outermost rib 1196. FIGS. 26A-26B illustrate a variation of the embodiment shown in FIGS. 25A-25B wherein a plurality of concentric ribs 1196 is provided outward from the flat trampoline center section 1194. For simplicity, the details of the outer circumferential rib 1142 and radially-inward extending portion 1144 are omitted in FIGS. 26A-26B.

Figure 27A:
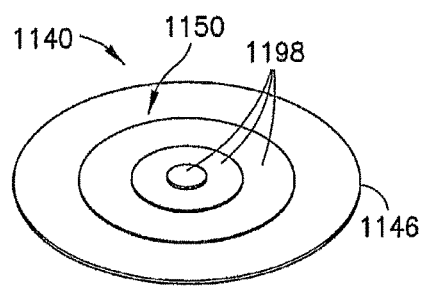
FIGS. 27A-27B are respective perspective and cross-sectional views of a fifteenth embodiment of the bladder for the cap-bladder assembly for the bladder syringe of FIGS. 1A-1B.
Figure 27B:
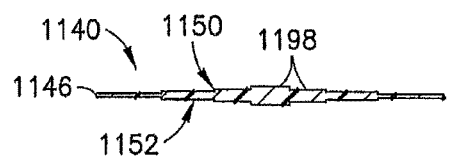

FIGS. 27A-27B illustrate an embodiment of the bladder 1140 in which the membrane portion 1146 has a series of thicker wall sections 1198 near the center of the bladder 1140, with the inner most wall section 1198 having the thickest cross-section. This embodiment allows for more material to be available in the center as the membrane portion 1146 is extended. The wall thickness increase could be a gradual transition rather than the shown stepped configuration. For simplicity, the details of the outer circumferential rib 1142 and radially-inward extending portion 1144 are omitted in FIGS. 27A-27B.

FIGS. 28A-28B illustrate an embodiment of the bladder 1140 in which the membrane portion 1146 defines a central well portion 1200 connected to an outer rim 1202 by a series of frangible webs 1204 that retard the release of bladder material to the interior wall 36 of the cylindrical body 30. Since the webs or ribs 1204 are frangible and tear away after a certain strain is achieved, the bladder 1140 in this embodiment is a one-time use component. For simplicity, the details of the outer circumferential rib 1142 (connected to the outer rim 1202) and radially-inward extending portion 1144 are omitted in FIGS. 28A-28B.

FIGS. 29A-29B illustrate an embodiment of the bladder 1140 in which the membrane portion 1146 has a second material molded-in or adhered to the outside surface to reduce the sliding along the plunger element 50. This material could have a higher coefficient of friction and could be friction bands 1206 around the membrane portion 1146, or could be in the form of friction pads 1206 provided on the bottom side 1152 of the membrane portion 1146 as illustrated. For simplicity, the details of the outer circumferential rib 1142 and radially-inward extending portion 1144 are omitted in FIGS. 29A-29B.

FIGS. 30A-30B illustrate an embodiment of the bladder 1140 in which the membrane portion 1146 has extra material 1208 on the outside circumference. This extra material 1208 is rolled-up like a condom instead of having one or more convolutes. The extra material 1208 unrolls as a vacuum draws the bladder 1140 like a rolling diaphragm. There may be a thicker section of material (not shown) in the center of the membrane portion 1146 to allow for additional stretch at extended fill volumes of the bladder 1140. For simplicity, the details of the outer circumferential rib 1142 and radially-inward extending portion 1144 are omitted in FIGS. 30A-30B.

FIGS. 31A-31B illustrate an embodiment of the bladder 1140 in which the membrane portion 1146 is composed of two or more materials. One material could be, for example, polypropylene to reduce friction. Additionally, the membrane portion 1146 could have over-molded ribs 1210 on the bottom side 1152 of the bladder 1140 that help keep the bladder 1140 from sticking to the interior wall 36 of the cylindrical body 30. These over-molded ribs 1210 are operable to lift the bladder 1140 off the interior wall 36 because they are raised surfaces, and may be made of a material with a low coefficient of friction, such as polypropylene, to enable the bladder 1140 to stretch down the interior wall 36. The over-molded ribs 1210 do not have to be continuous and could be short segments as illustrated to allow the bladder 1140 freedom to stretch in all directions. For simplicity, the details of the outer circumferential rib 1142 and radially-inward extending portion 1144 are omitted in FIGS. 31A-31B.

FIGS. 32A-32B illustrate a clam-shaped embodiment of the bladder 1140. In this embodiment, the membrane portion 1146 is shaped like a clam with an undulating surface texture 1212 that creates more surface area for a constrained diameter. This membrane portion 1146 may have a uniform wall thickness or varying wall thickness. For simplicity, the details of the outer circumferential rib 1142 and radially-inward extending portion 1144 are omitted in FIGS. 32A-32B.

FIGS. 33A-33B illustrate an embodiment of the bladder 1140 in which the membrane portion 1146 has a non-symmetric cross-section such as formed by interlinked hourglass shaped sections or beads 1214 with repeated thick and thin sections/beads. For simplicity, the details of the outer circumferential rib 1142 and radially-inward extending portion 1144 are omitted in FIGS. 33A-33B.

Figure 34B:
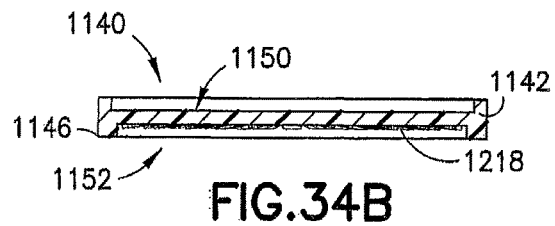
FIGS. 34A-34B are respective perspective and cross-sectional views of a twenty-second embodiment of the bladder for the cap-bladder assembly for the bladder syringe of FIGS. 1A-1B.
Figure 34A:
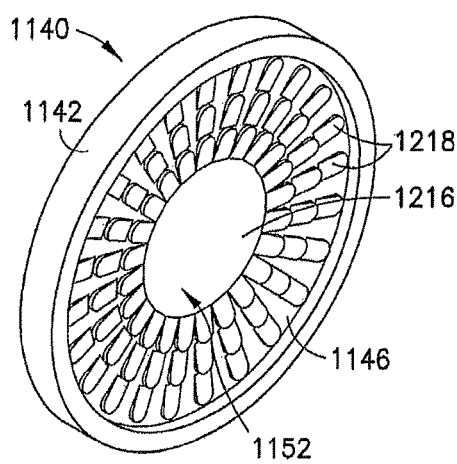

FIGS. 34A-34B illustrate an embodiment of the bladder 1140 in which the membrane portion 1146 has a flat trampoline center section 1216 in the center and a series or plurality of stepped and radially-extending ribs or spokes 1218 extending outward from the center section 1216 to the outer circumferential rib 1142. The stepped and radially-extending ribs or spokes 1218 may be provided on the bottom or proximal side 1152 of the membrane portion 1146, as illustrated, or on both sides.

FIGS. 35A-35B show an embodiment of the bladder 1140 similar to the bladder 1140 shown in FIGS. 34A-34B. In the embodiment shown in FIGS. 35A-35B, the bottom side 1152 of the membrane portion has a flat trampoline center section 1220 in the center and a series or plurality of concentric stepped or ridged portions 1222 around the center section 1220. These concentric stepped or ridged portions 1222 may be adapted to cooperate with corresponding concentric stepped or ridged portions 1224 on the surface of the distal portion 52 of the plunger element 50. In this embodiment, material is present in the center of the bladder 1140 in the unstretched state. Thicker material is present due to the stepped increases in the thickness toward the center of the membrane portion 1146 and the stepped or ridged portions 1224 on the plunger element 50 are disposed to cooperatively engage the corresponding concentric stepped or ridged portions 1222 to retard the distribution of the bladder material to the interior wall 36 of the cylindrical portion 30. As the steps or ridges 1222 lock on the steps or ridges 1224 on the distal portion 52 of the plunger element 50, the bladder material will be pulled until the strain on the bladder 1140 causes the material to thin in the area of the ridge 1224 and it will be released and a new transition or portion will slide down until it "locks" onto the subsequent plunger ridge 1224 until the steps or ridges 1222 ultimately disappear as the bladder 1140 is filled and stretched. The plunger element 50 may have multiple steps or ridges 1224 or only require a singular step or ridge 1224 toward the outside radius thereof.

Figure 36:
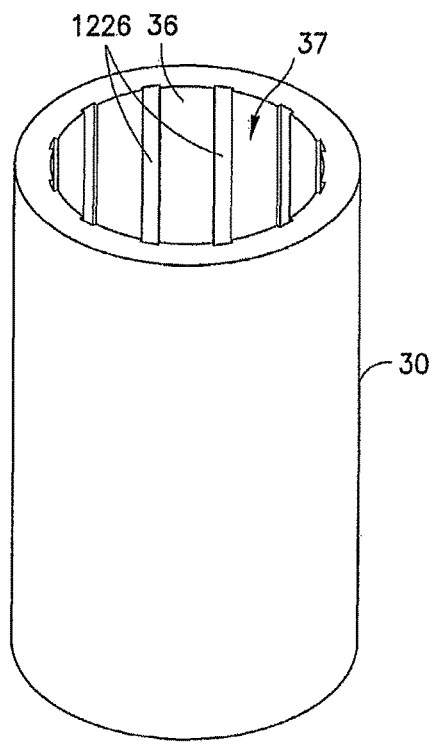
FIG. 36 is a perspective view showing the cylindrical body of the bladder syringe with interior surface texturing to reduce sliding friction between the bladder and the interior wall of the cylindrical body.

Referring next to FIG. 36, vertical grooves 1226 may be provided on the interior wall 36 of the cylindrical body 30 to desirably reduce sliding friction between the bladder 1140 and the interior wall 36 and allow the bladder 1140 to slide more easily along the interior wall 36. The vertical grooves 1226 are operable to lift the bladder 1140 off the interior wall 36 because they reduce the area in surface contact between the bladder 1140 and the interior wall 36. While vertical grooves 1226 are shown in FIG. 36, it is possible to modify the surface finish of the interior wall 36 in other ways to reduce the amount of surface area contact between the bladder 1140 and the interior wall 36. This modification could be done when molding the cylindrical body 30, such as providing the interior wall 36 with straight groove lines, as shown, adding a roughened surface finish, or adding vertical ribs along the interior wall 36 of the cylindrical body 30.

Figure 37:
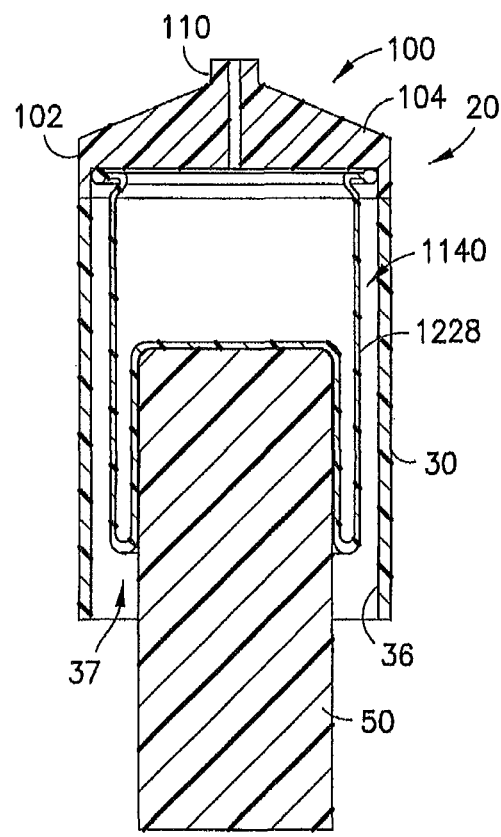
FIG. 37 is a schematic cross-sectional view of the bladder syringe of FIGS. 1A-1B in which the bladder for the cap-bladder assembly is in the form of a rolling diaphragm.

Referring to FIG. 37, an embodiment of the bladder 1140 is shown in which the membrane portion 1146, or body of the bladder 1140, is in the form of a rolling diaphragm 1228. In FIG. 37, the plunger element 50, cylindrical body 30, and cap-bladder assembly 100 of the bladder syringe 20 are shown schematically, and details of the connection/interaction between these elements are omitted but may be similar to that shown in FIGS. 1-2. The rolling diaphragm 1228 is longer in the axial direction in the bore 37 of the cylindrical body 30 and is adapted to fold over onto itself. The plunger element 50 operates as a displacement plunger and does not seal against the interior wall 36 of the cylindrical body 30, and is sized to provide a small annular clearance area between the plunger element 50 and the interior wall 36 of the cylindrical body 30 on the order of two thicknesses of the rolling diaphragm 1228. The rolling diaphragm 1228 may be resiliently elastic or may be not be stretchable in this embodiment. If the rolling diaphragm 1228 is not stretchable, then the rolling diaphragm 1228 is desirably about half the length of the cylindrical body 30.

Figure 38:
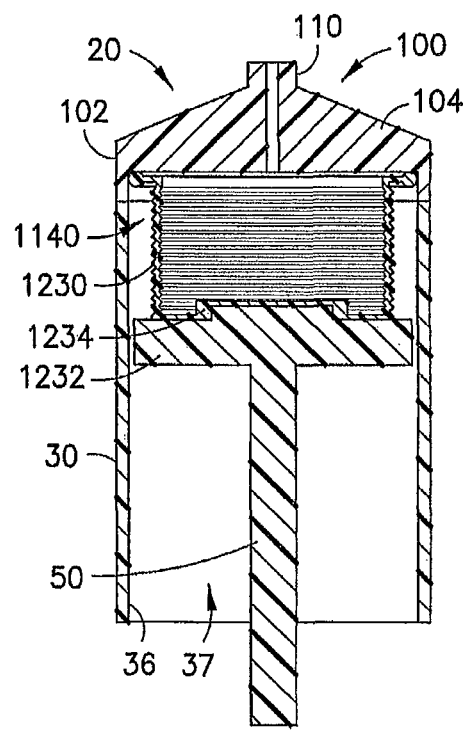
FIG. 38 is a schematic cross-sectional view of the bladder syringe of FIGS. 1A-1B in which the bladder for the cap-bladder assembly is in the form of a bellows.

Referring to FIG. 38, in this embodiment the bladder 1140 has a membrane portion 1146, or body, of the bladder 1140, that is molded out of a non-fellable material, such as thin walled PET. In this embodiment, the membrane portion 1146, or body, of the bladder 1140 is shaped like an open topped cylinder 1230. The walls of the bladder cylinder 1230 are corrugated and folded like a bellows. In FIG. 38, the plunger element 50, cylindrical body 30, and cap-bladder assembly 100 of the bladder syringe 20 are shown schematically, and details of the connection/interaction between these elements are omitted but may be similar to that shown in FIGS. 1-2. The piston element 50 has a large distal disc portion 1232 to support a rigid bottom 1234 of the bladder cylinder 1230 and a fixed or inter-engaging connection may be provided between the bladder cylinder bottom 1234 and the disc portion 1232 to enable the piston element 50 to operate the bladder cylinder 1230 in the forward or distal and rearward or proximal directions in the bore 37 of the cylindrical body 30. The bladder cylinder 1230 may be blow molded in this embodiment and be in other shapes rather than cylindrical, such as a diamond shape (e.g., polygonal).

Figures 39A, 39B:
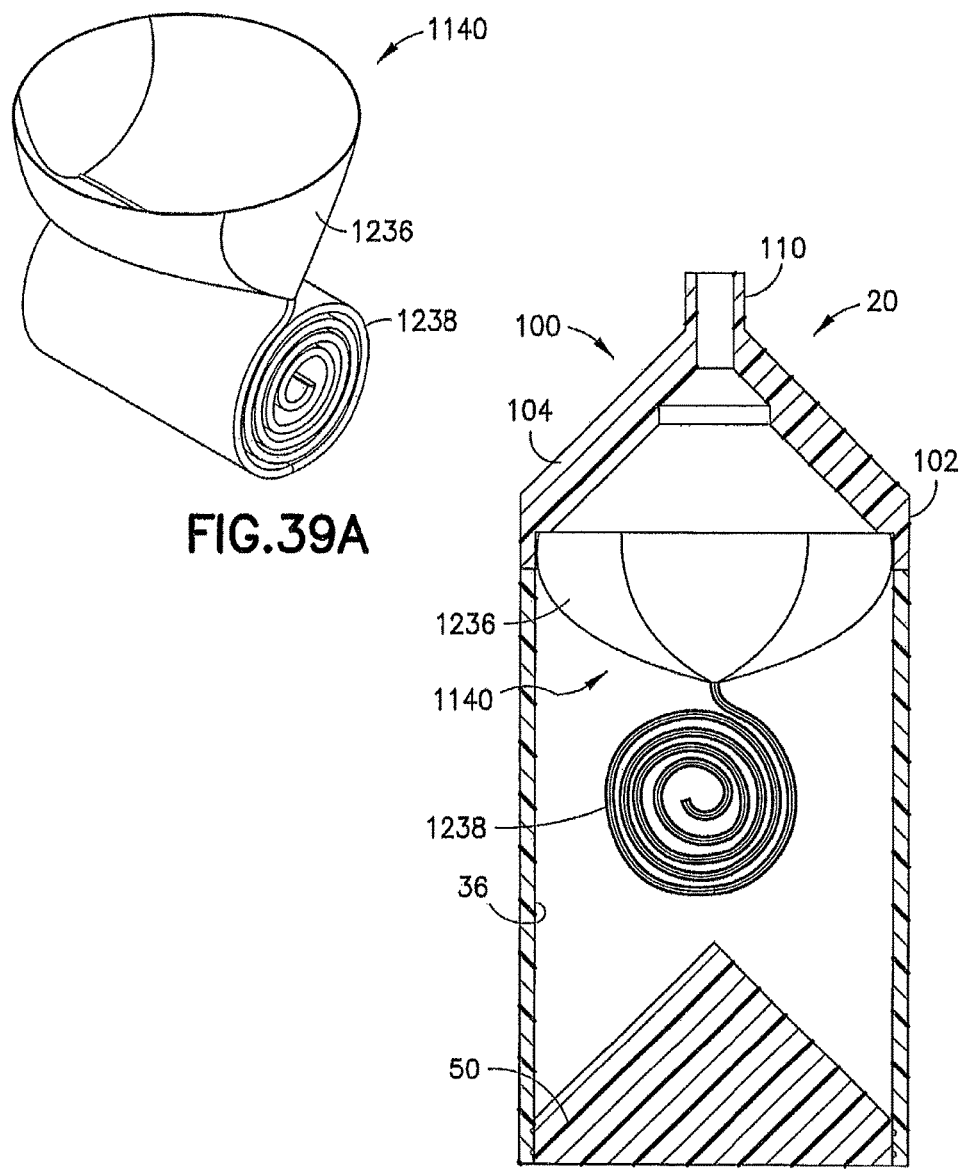
FIGS. 39A-39B are a perspective view of a bladder and a schematic cross-sectional view, respectively, of the bladder syringe of FIGS. 1A-1B in which the bladder for the cap-bladder assembly is in the form of a cup-shaped distal portion having a depending rolled-up portion.

Referring to FIGS. 39A-39B, an embodiment of the bladder 1140 has a membrane portion 1146, or body, of the bladder 1140, that is formed by a cup-shaped distal portion 1236 and a depending rolled-up portion 1238. FIG. 39A shows an isolation view of the bladder 1140 according to this embodiment, and FIG. 39B shows the bladder 1140 associated with the overall bladder syringe 20. In FIG. 39B, the plunger element 50, cylindrical body 30, and cap-bladder assembly 100 of the bladder syringe 20 are shown schematically, and details of the connection/interaction between the cup-shaped portion 1236 of the bladder 1140 and the cap body 104 are omitted but may be similar to that shown in FIGS. 1-2. In use, air is removed from behind the bladder 1140 in this embodiment by advancing the plunger element 50 until the shape of the bladder 1140 is completely flat in the cap body 104 and then the bladder 1140 is filled according to the general procedure described previously using vacuum pressure, which unfurls the depending rolled up portion 1238. The bladder 1140 in this embodiment is stiff enough to expand without vacuum.

Referring next to FIG. 40, an embodiment of the bladder 1140 is shown that is pulled down by operation of the plunger element 50 rather than vacuum-operated. In this embodiment, the membrane portion 1146 is shaped like an open cylinder with a rigid bottom portion 1240 and a flexible sidewall 1242. If desired, the rigid bottom portion 1240 and flexible sidewall 1242 may be integrally molded together and, further, the rigid bottom portion 1240, flexible sidewall 1242, and cap body 104 may all be molded integrally together using co-injection molding techniques to arrive at the schematically illustrated embodiment shown in FIG. 40. In operation, the plunger element 50 is adapted with a connecting element 1244 that is adapted to engage a corresponding connecting element 1246 in the rigid body portion 1240 so that the rigid bottom portion 1240 and plunger element 50 become fixed together. During the reciprocal movement of the plunger element 50, in the directions of arrows $A_1$, $A_2$ described previously, the flexible sidewall 1242 stretches based on the linear movement of the piston element 50. In FIG. 40, the plunger element 50, cylindrical body 30, and cap-bladder assembly 100 are shown schematically, and details of the connection/interaction between the cylindrical body 30 and the cap-bladder assembly 100 may be found in the foregoing.

In FIG. 41, an embodiment of the bladder 1140 is shown in which the membrane portion 1146 matches a tapered profile 1248 of the interior cavity 106 of the cap body 104 and has an open end 1250 with a short sidewall 1252. In this embodiment, the bladder 1140 nests into the interior cavity 106 of the cap body 104 and is protected. In operation, the plunger element 50 (not shown in FIG. 41) is moved forward or distally into the interior cavity to expel air out from between the distal portion 52 of the plunger element 50 and the bladder 1140 and is then drawn backward to cause the bladder 1140 to fill with fluid. As the plunger element 50 retracts vacuum pressure is generated and the membrane portion 1146, which has the shape of the interior cavity 106 of the cap body 104, to enable the bladder 1140 to fill with fluid. In FIG. 41, the cylindrical body 30 and cap-bladder assembly 100 are shown schematically, and details of the connection/interaction between the cylindrical body 30 and the cap-bladder assembly 100 may be found in the foregoing.

In FIGS. 42A-42B, an embodiment of the bladder 1140 is shown in which the membrane portion 1146 is provided in the form of a flexible body that has an outer diameter to fit within the inner diameter of the cylindrical body 30, and the cap body 104 is molded as a solid planar end cap that is adapted to seat onto a planar top rim 45 of the cylindrical body 30. Additionally, the flexible body has a side connector 1254, which is illustrated as a luer connector for connection to a fluid container or tubing set, as examples. The bladder 1140 may be of two-piece construction in which the side connector 1254 is molded of a different material than the flexible cylindrical bladder 1140. For example, the side connector 1254 may be co-injection molded with the flexible bladder 1140 yielding a unitary structure as illustrated in FIGS. 42A-42B. Once the flexible bladder 1140 is placed in the cylindrical body 30, the plunger element 50 (not shown) is moved forward or distally to expel air out from the flexible bladder 1140 via the side connector 1254, and withdrawal of the plunger element 50 draws a vacuum in the cylindrical body 30 and fluid enters the flexible bladder 1140 via the side connector 1254.

Figure 43A:
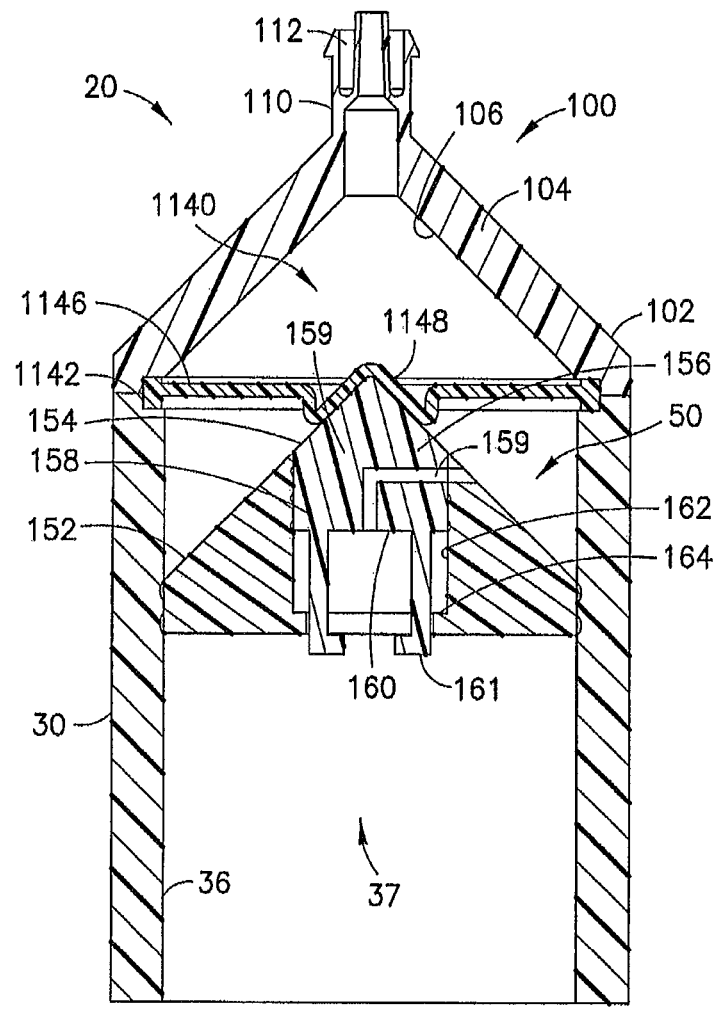
FIGS. 43A-43C are schematic cross-sectional views of another embodiment of the bladder syringe that incorporates a dual vacuum plunger element.
Figure 43B:
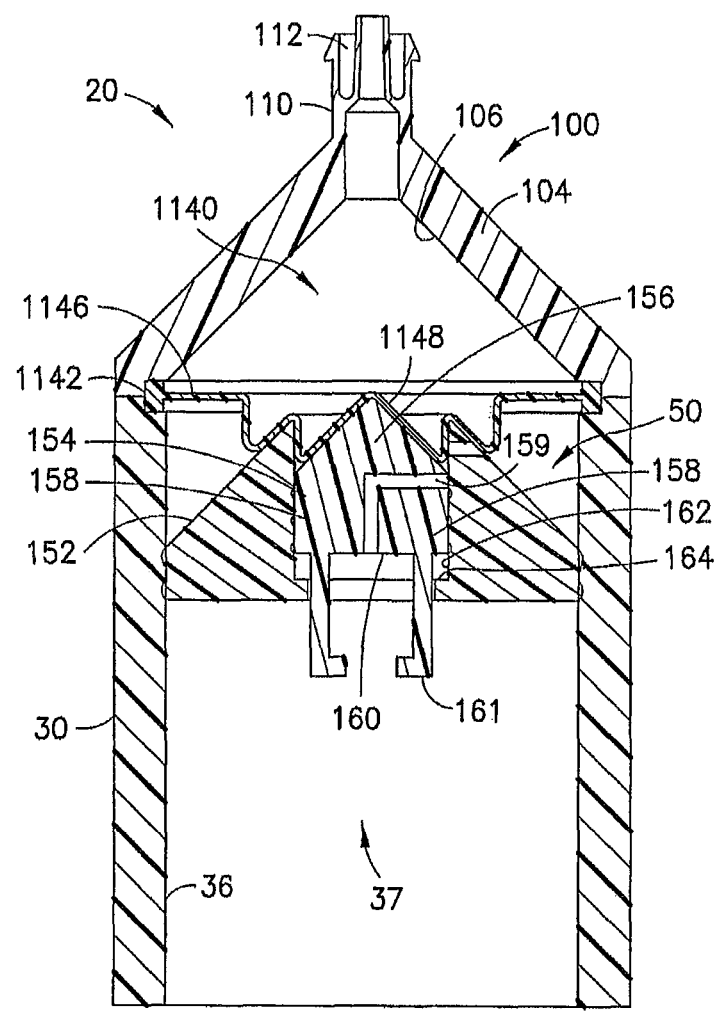
Figure 43C:
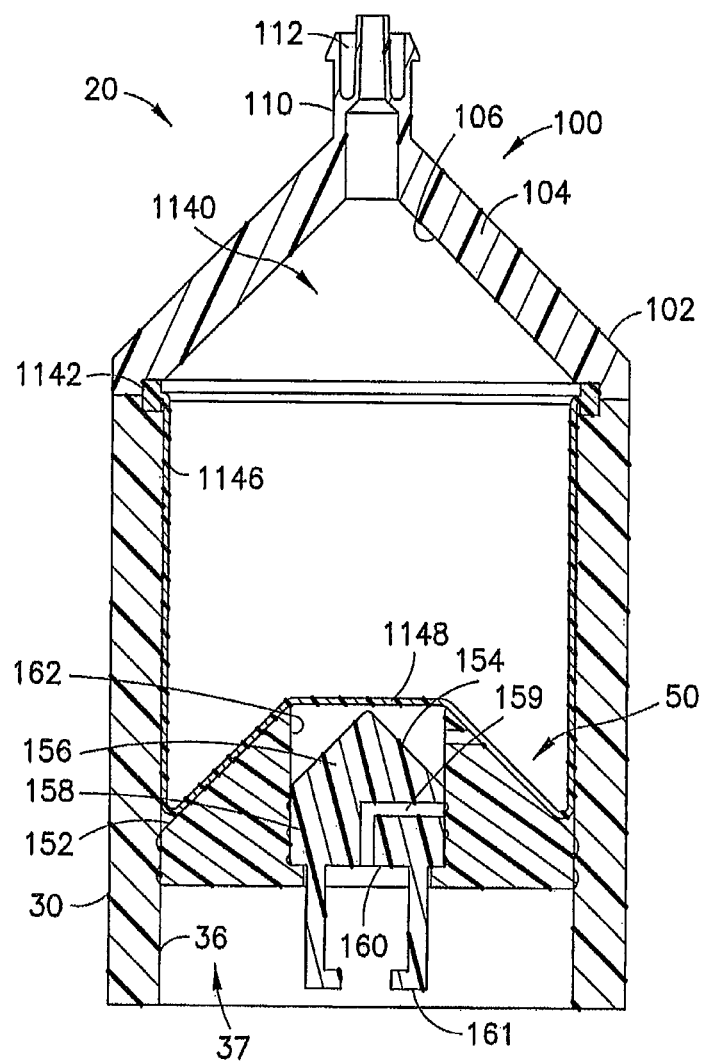

Referring to FIGS. 43A-43C, another embodiment of the bladder syringe 20 is shown that incorporates a dual vacuum plunger element 50. In this embodiment, the bladder 1140 has the general configuration of the bladder syringe 20 shown in FIGS. 12A-12B with the membrane portion 1146 having a general W-shaped convoluted central well portion 1148 so that extra material is present in the center of the membrane portion 1146 to allow for slow release of material to the interior wall 36 of the cylindrical body 30. The dual vacuum plunger element 50 comprises an outer plunger element 152 surrounding an inner plunger element 154, with the inner plunger element 154 being movable relative to the outer plunger element 152. The inner plunger element 154 comprises a conical distal portion 156 generally shaped to engage the center of the W-shaped convoluted central well portion 1148 of the bladder syringe 20, as generally shown in FIG. 43A, and a cylindrical proximal portion 158. An internal vent 159 extends interiorly within the cylindrical portion 158 from the circumferential exterior of the cylindrical portion 158 to a proximal end 160 of the cylindrical portion 158. The proximal end 160 of the cylindrical portion 158 is provided with engagement tabs 161 for engagement with the piston interface tip 16 of the piston element 14 of the fluid injector 12 shown in FIG. 7, discussed previously. In operation, air is expunged from between the bladder 1140 and the cap body 104 by advancing the dual plunger element 50, in the assembled state shown in FIG. 43A, forward so that the conical distal end presented by the assembled dual plunger element 50 seats in the interior cavity 106 of the cap body 104 in a similar manner to the operation of the bladder syringe 20 discussed previously. The internal vent 159 permits air to be vented from the bore 37 of the cylindrical body 30 distal or forward of the dual plunger element 50 as the dual plunger element 50 is advanced.

In the present embodiment, when it is desired to fill the bladder syringe 20, the inner plunger element 154 retracts first relative to the outer plunger element 152, as shown in FIG. 43B, thereby closing the internal vent 159 and drawing in the loose material of the convoluted central well portion 1148 of the bladder syringe 20 into an annular space 162 defined by the outer plunger element 152 wherein the inner plunger element 154 is located, as shown in FIGS. 43B-43C. At this point, the outer plunger element 152 also engages or contacts the bladder 1140. In FIG. 43C, the cylindrical portion 158 of the inner plunger element 154 seats against a shoulder 164 defined by the outer plunger element 152 in the annular space 162 and both the outer plunger element 152 and the inner plunger element 154 thereafter retract together. As the plunger elements 152, 154 retract and the bladder 1140 fills with fluid, and the bladder material in contact with the outer plunger element 152 is drawn out first followed by the loose material at the center of the W-shaped convoluted central well portion 1148 in contact with the inner plunger element 154. Once the bladder 1140 is filled with fluid to the desired volume, the plunger elements 152, 154 may be advanced together by the piston element 14 of the fluid injector 12 shown in FIG. 7. A mechanical pre-stretch of the bladder 1140 could also be performed before operation of the dual plunger element 50 in the foregoing manner. In FIGS. 43B-43C, the connection between the cap-bladder assembly 100 and the cylindrical body 30 is shown schematically. In summary, in the embodiment shown in FIGS. 43B-43C, a co-axial dual plunger element 50 is used to generate a vacuum. As the dual plunger element 50 moves forward, the interior vent 159 is open allowing the air between the bladder 1140 and the piston dual plunger element 50 to escape. When the piston element 14 of the fluid injector 12 draws the dual plunger element 50 back, the inner plunger element 154 withdraws into the outer plunger element 152 closing and sealing the internal vent 159 in the inner plunger element 154 and creating a vacuum. The co-axial dual plunger element 50 pulls bladder material into the center as the annular space 162 is formed or opens between the inner and outer plunger elements 152, 154 to keep the bladder 1140 in a correct position for filling.

Figures 44A, 44B:
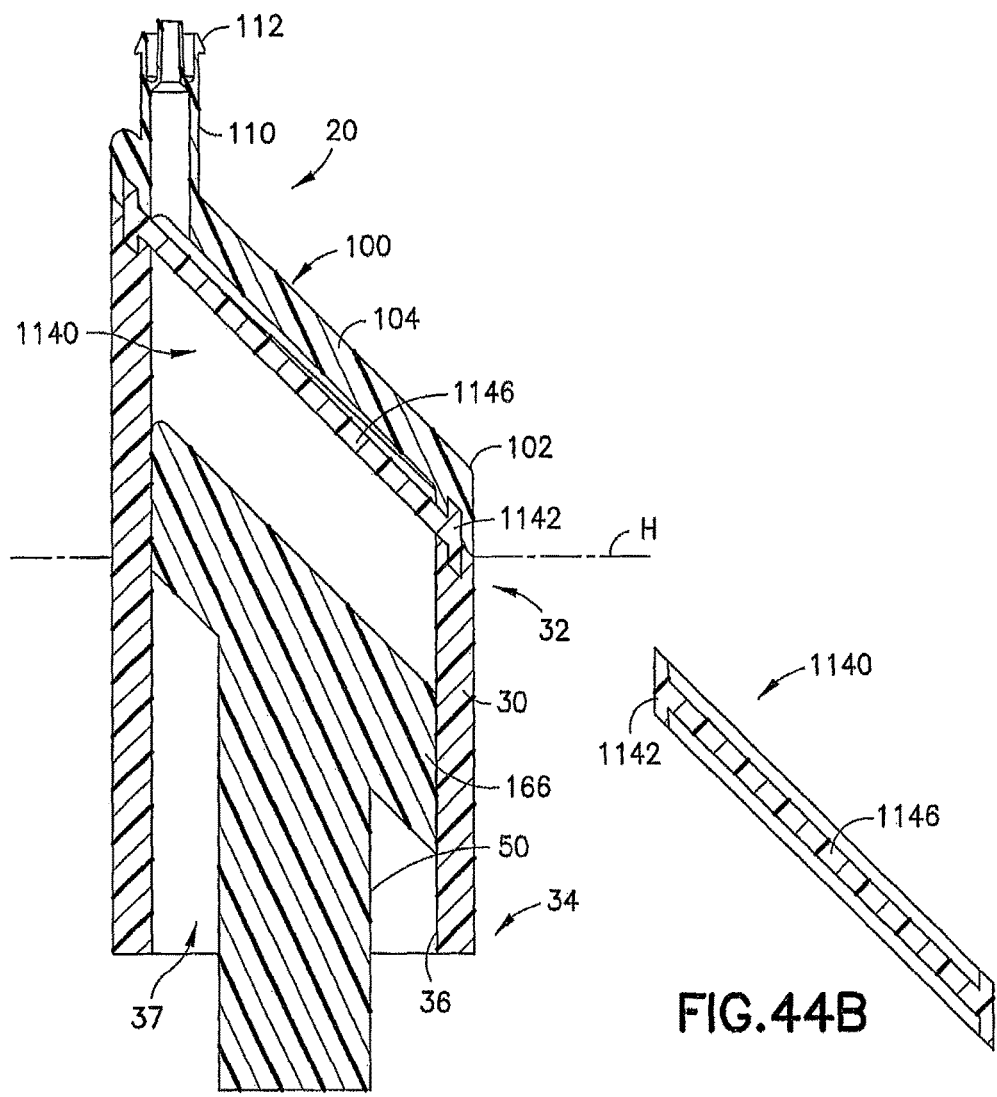
FIGS. 44A-44B are respectively a schematic cross-sectional view and a cross-sectional view of another embodiment of the bladder syringe and a bladder therefor, each set at an angle to allow for more surface area of contact between the bladder and the plunger element.

Referring to FIGS. 44A-44B, another embodiment of the bladder syringe 20 is shown that incorporates a cylindrical body 30, plunger element 50, cap body 104, and bladder 1140 each set an angle to allow for more surface area of contact between the bladder 1140 and plunger element 50. In these figures, the plunger element 50, cylindrical body 30, and cap body 104 of the bladder syringe 20 are shown schematically, and details of the connection/interaction between these elements are omitted but may be similar to that shown in FIGS. 1-2. In this embodiment, the distal end 32 of the cylindrical body 30 and a distal plunger head 166 of the plunger element 50 define corresponding obtuse angles with a horizontal plane H, and the cap body 104 is formed to match the angular shape of the distal end 32 of the cylindrical body 30. The bladder 1140 comprises a planar membrane portion 1146 but the membrane portion defines the same angle as the foregoing components between the circumferential rib 1142. This angular orientation allows more bladder material to be stretched as the angled plunger element 50 is withdrawn in the cylindrical body 30 during filling of the bladder 1140. The bladder 1140 is also placed at an obtuse angle to the interior wall 36 of the cylindrical body 30, as opposed to perpendicular as in previous embodiments, and this obtuse angle provides a greater surface area for contact between the bladder 1140 and plunger element 50, and the angular orientation increases the surface area of available bladder material as well as the surface contact area with the plunger element 50. The greater contact surface area means less strain on the bladder 1140 as it is stretched to extended fill volumes. The distal plunger head 166 of the plunger element 50 is generally shaped to accommodate this obtuse angle, and could also be square or round depending on the cross-sectional shape of the cylindrical body 30, which need not be horizontal and circular in cross-section in this embodiment. A further alternative for this embodiment mounts the bladder 1140 at an obtuse angle but is provided to have a shape to match the conical interior cavity of the conical cap body 104 shown in previous embodiments. In FIGS. 44A-44B, the connection between the cap-bladder assembly 100 and the cylindrical body 30 is shown schematically.

Figure 45A:
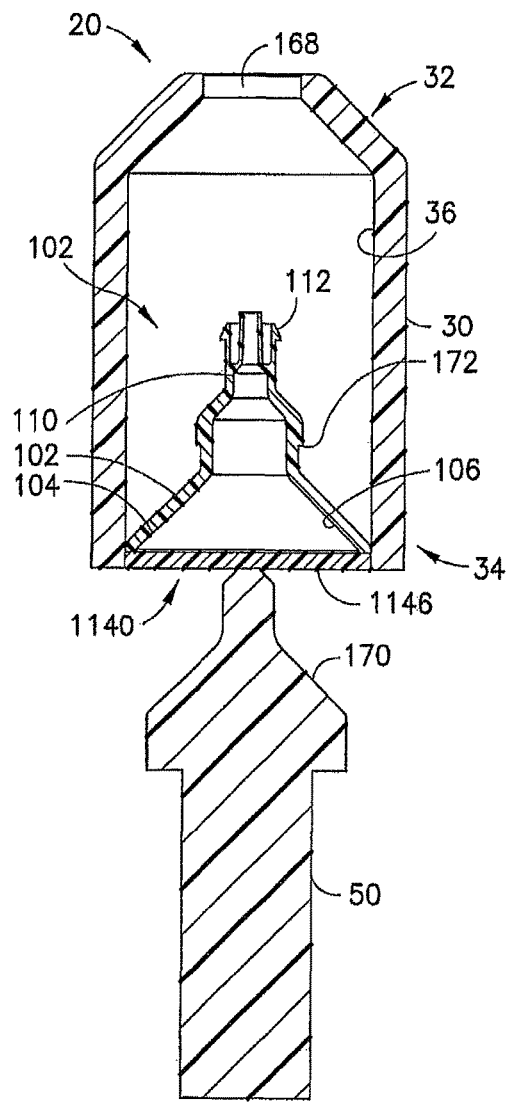
FIGS. 45A-45B are respective schematic cross-sectional views of another embodiment of the bladder syringe in which the cap-bladder assembly is breach-loaded into the cylindrical body of the bladder syringe.
Figure 45B:
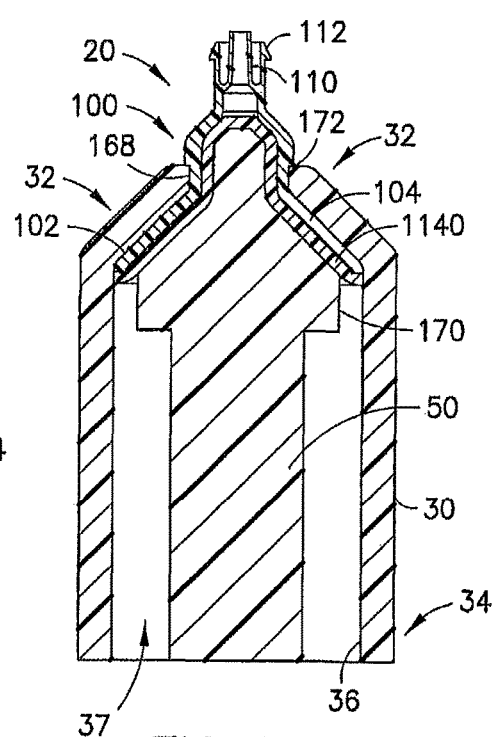

Referring to FIGS. 45A-45B, another embodiment of the bladder syringe 20 is shown schematically in which the cap body 104 and bladder 1140 are breach-loaded into the bore 37 of the cylindrical body 30. Prior to use, the cap body 104 and bladder 1140 may be disposed in the bore 37 of the cylindrical body 30 at the proximal end 34 of the cylindrical body 30. In this embodiment, the distal end 32 of the cylindrical body 30 may be conical-shaped and define a distal opening 168. The plunger element 50 has a plunger head 170 that is shaped to match the interior shape of the cap body 104, and the plunger element 50 is used to move the cap body 104 and the bladder 1140 forward in the bore 37 of the cylindrical body 30. The cap body 104 further comprises a locking rim 172 on the discharge conduit 110 that is adapted for engagement with the distal opening 168 so that when the plunger element 50 moves the cap body 104 and bladder 1140 forward to the conical distal end 32 of the cylindrical body 30, the discharge conduit 110 passes through the distal opening 168 and the cap body 104 eventually locks onto the conical shaped distal end 32 of the cylindrical body 30 via the locking rim 172. One of the locking rim 172 and distal opening 168 is desirably capable of a certain degree of resilient flexure, such as providing resilient flexible segments in the distal end 32 of the cylindrical body 30 that define the distal opening 168, so that the locking rim 172 may pass through the distal opening 168 and engage and lock onto the conical distal end 32 of the cylindrical body 30. The distal or forward movement of the plunger element 50 to lock the cap body 104 to the distal end 32 of the cylindrical body 30 also expel air from the space between the bladder 1140 and the cap body 104 via the discharge conduit 110. When the plunger element 50 is withdrawn in the cylindrical body 30, the bladder 1140 is stretched under vacuum pressure in the manner discussed previously and filled with fluid while the cap body 104 remains connected to the distal end 32 of the cylindrical body 30. The bladder 1140 is extended when the plunger head 170 of the plunger element 50 is advanced into interior cavity 106 of the cap body 104.

Figure 46A:
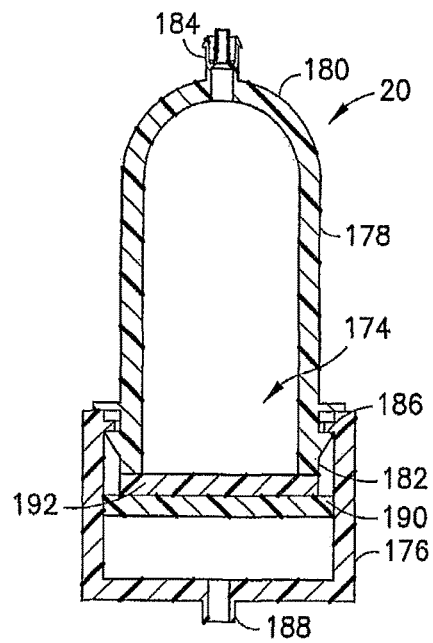
FIGS. 46A-46C are respective schematic cross-sectional views of another embodiment of the bladder syringe in which a dual diaphragm arrangement in the cap-bladder assembly is driven by a fluid displacement actuator.
Figure 46B:
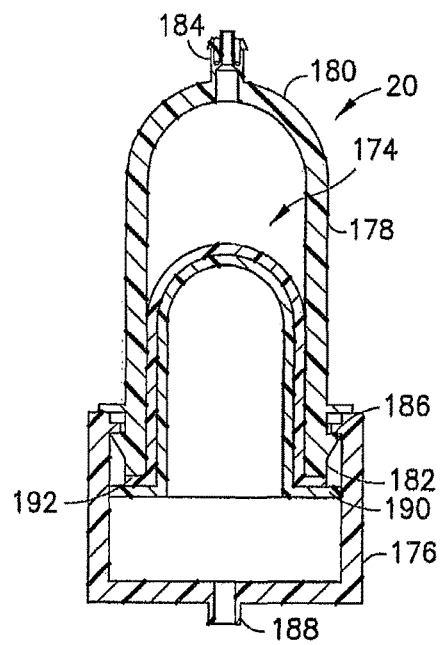
Figure 46C:
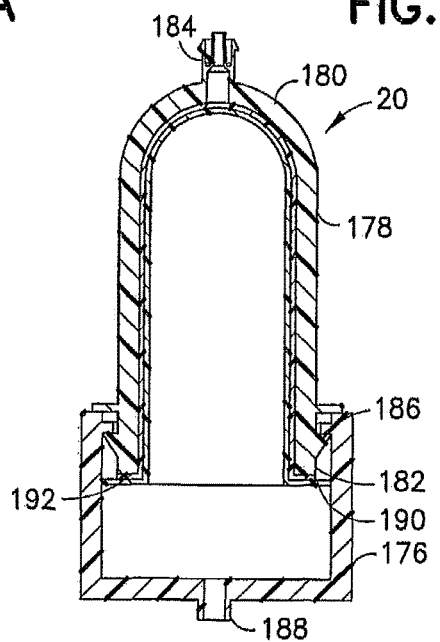

Referring to FIGS. 46A-46C, another embodiment of the bladder syringe 20 is shown schematically and comprising a dual diaphragm arrangement 174 which is driven by a fluid displacement actuator 176. In this embodiment, a syringe body 178 is provided having a closed distal end 180 and an open proximal end 182. The distal end 180 has a discharge port 184 with an end connector. The proximal end 182 of the syringe body 178 is adapted for a releasable fixed connection with the fluid displacement actuator 176, such as may be found in the Medrad, Inc. patents discussed previously, which describe interfacing features for securing a Stellant® CT syringe to a Stellant® fluid injector. The fluid displacement actuator 176 comprises an open interfacing end 186 to accept and connect to the proximal end 182 of the syringe body 178, and further comprises a pressurization port 188 for connection to a fluid pressurizing source used to pressurize the fluid displacement actuator 176. A reusable bladder 190 is provided in the fluid displacement actuator 176 and is adapted to drive a disposable bladder 192 that covers the proximal end 182 of the syringe body 178. The syringe body 178 and attached disposable bladder 192 form the single-use disposable portions of the dual diaphragm system 174 of this embodiment. The disposable bladder 192 may be co-injection molded to the open proximal end 182 of the syringe body 178. As shown in FIGS. 46B-46C, as the fluid displacement actuator 176 is pressurized, the disposable bladder 192 is driven by the reusable bladder 190 to alternately fill the syringe body 178 with fluid and dispense fluid therefrom.

The numerous foregoing shapes of the bladder 1140 provide various embodiments with different characteristics in the way the material of the bladder 1140 is distributed to the interior wall 36 of the cylindrical body 30 during operation of the bladder syringe 20 with the fluid injector 12. The provision of more material in the center of the membrane portion 1146 slows the release of the bladder 1140 to the interior wall 36 of the cylindrical body 30 during withdrawal operation of the plunger element 50 in the bladder syringe 20, as is provided by one or more of the embodiments of the bladder 1140 discussed previously. The provision of more central material generally reduces stress and strain in the bladder 1140 during elongation, up to a point where the extra material becomes too thick to expand/elongate easily. In particular, adding curvature or convolutes C to the membrane portion 1146, such as the embodiment shown in FIGS. 12-13, as an example, reduces stress and strain in the bladder 1140 during elongation.

Suitable materials for the bladder 1140 include any material that would permit a substantially maximum fill of the bladder 1140 and this entails an elongation of the bladder 1140 of between about 800-1800%. A low modulus (15-30 psi at 300% elongation) is also desirable for filling of the bladder 1140 by reducing the amount of vacuum required to expand the bladder 1140 during filling. Thermoplastic Elastomer (TPE) is one suitable and preferred choice for the bladder 1140. This material can be clear or translucent, can have an elongation of over about 1400% with a low modulus/durometer, and can be injection molded. Thermoplastic elastomer (SBS rubber in olefinic matrix) has been demonstrated to work well for the bladder 1140, has successfully reached an 1800% elongation, has a low modulus/durometer, and can be injection molded. Silicone, urethane, and polyisoprene (natural or synthetic) are also suitable choices of materials for the bladder 1140. A material with clarity for air bubble detection is also desirable and this requirement is met by the foregoing materials. Further, while mentioned in connection with certain embodiments, it is also possible within the teachings of this disclosure to eliminate the use of the retainer ring 140 and have the bladder 1140 co-injection molded with the cap body 104, with the cap body 104 and bladder 1140 being formed of different materials.

It is desirable in accordance with this disclosure to co-injection mold the bladder 1140 to the cap body 104 of the cap 102, which would eliminate the need for the retainer ring 140. Typically, the cap body 104 of the cap 102 is molded from a rigid thermoplastic material like polyester and, without removing the cap body 104 from the molding tool, the bladder 1140 may be over-molded to the cap body 104. As discussed in the foregoing, the bladder 1140 may be made of soft, highly elastic material, such as TPE, that is molded directly onto the cap body 104. The formed cap body 104 with attached bladder 1140 is ejected from the molding tool as one component with no further assembly required. In the foregoing process, the TPE (or any bladder material described herein) is inhibited from forming a chemical bond with the interior of the cap body 104 by providing suitable surface texturing in the interior cavity 106, by appropriate material selection for the bladder 1140 and the cap body 104, and/or by applying anti-bonding agents between the cap body 104 and the bladder 1140; typically only vacuum pressure is available according to most embodiments described herein to "pull" the bladder 1140 outward from the cap body 104 and fill the bladder syringe 20 with fluid. Molding the bladder 1140 with the cap body 104 provides benefits of low manufacturing cost and lower particulate formulation, and eliminates the need to manually assemble the bladder 1140 to the cap body 104. Additionally, the sterilization cycle time may be reduced. Nonetheless, this disclosure also includes the option of sterile molding of the cap body 104 separate from the bladder 1140, which allows greater flexibility in the design and shape of the bladder 1140 as the bladder 1140 no longer needs to follow the shape of the cap body 104, and this variation includes use of the retainer ring 140. Furthermore, the bladder 1140 may be over-molded onto the retainer ring 140 which is then inserted into the interior cavity 106 of the cap body 104 of the cap 102, (see the arrangement shown in FIGS. 13A-13B as an example). The retainer ring 140 provides a rigid frame to support the bladder 1140 and can isolate the bladder 1140 from assembly torque during installation of the cap-bladder assembly 100 on the cylindrical body 30. In yet a further molding method, the cap body 104 and bladder 1140 may be co-injection molded and use still a retainer ring 140 to support the bladder 1140 in the interior cavity 106 of the cap body 104 of the cap-bladder assembly 100.

Figure 47A:
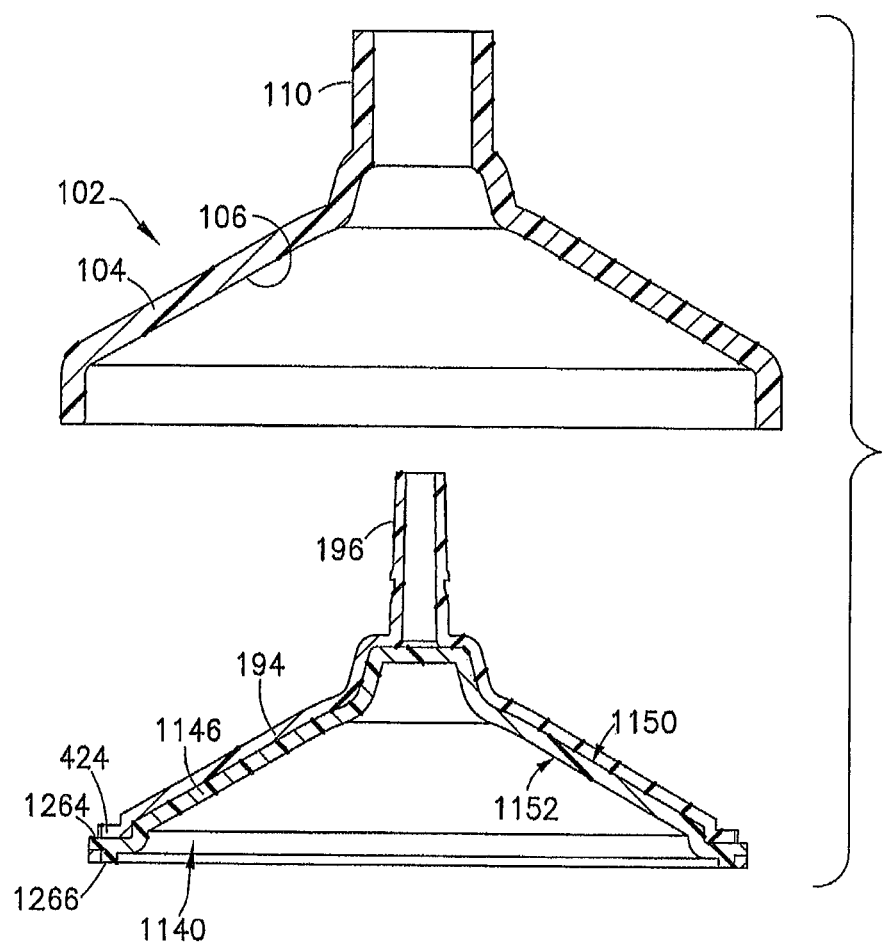
FIGS. 47A-47F are respective schematic views showing variations in forming the cap-bladder assembly according to co-injection molding and/or over-molding techniques.

As an alternative in the foregoing over-molding process, as shown in FIG. 47A, the bladder 1140 may be co-injection molded with a thin inner liner 194 that fits within a reusable cap body 104 that cooperates with the cylindrical body 30 in the manner described previously, and eliminates the need for the retainer ring 140. Thus, in this variation, the bladder 1140 is over-molded to the inner liner 194, which may be made of polypropylene or any other of the plastic materials detailed previously in connection with the cap body 104. Again, the bladder 1140 is prevented from forming a chemical bond with the interior of the inner liner 194. In this embodiment, the cap body 104 comprises a discharge conduit 110 and the inner liner 194 also includes a discharge conduit 196 that fits within the discharge conduit 110. In FIG. 47A, the inner liner 194 has an exterior circumferential rim 424 that is molded to an exterior circumferential rim 1264 of the bladder 1140. Alternatively, the circumferential rims 424, 1264 may be secured by other means such as ultrasonic welding, adhesive, and like joining methods. The exterior rim 1264 on the bladder 1140 comprises a depending rib 1266 adapted for providing a sealing engagement with the distal end or rim of the cylindrical body 30 in an embodiment of the bladder syringe 20 shown in FIGS. 71A-71C described herein.

Figure 47B:
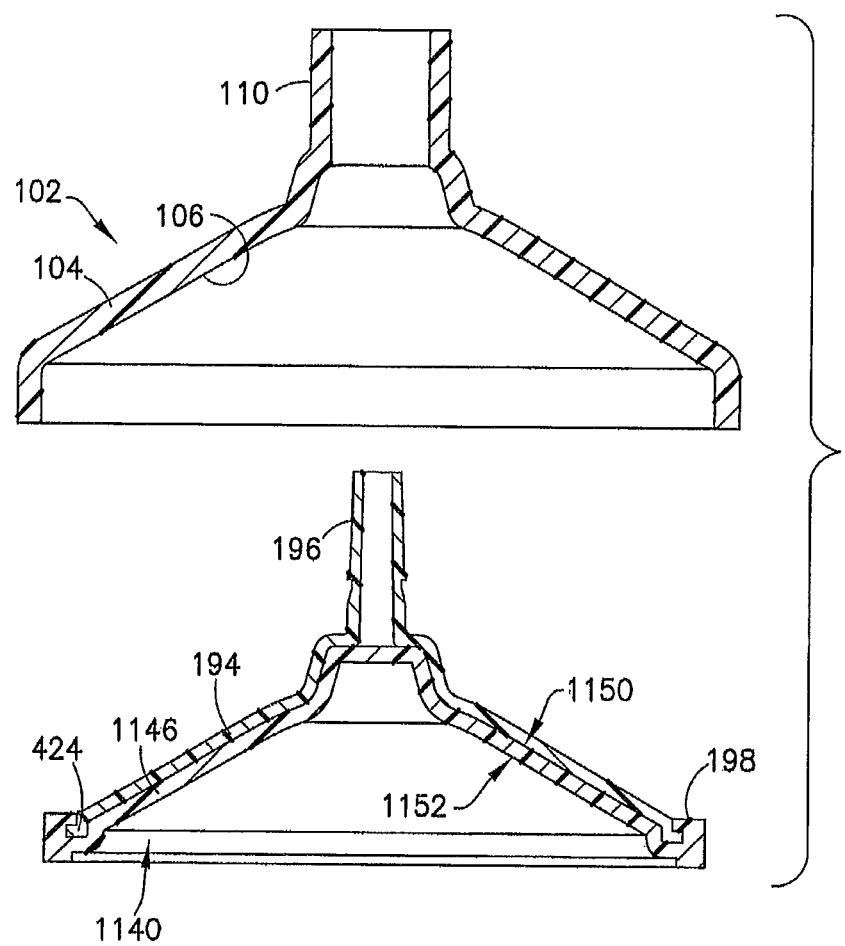

While in FIG. 47A, the bladder 1140 is shown connected to the open end of the inner liner 194, the bladder 1140 may be molded to the inner liner 194 so as to wrap around the exterior of the inner liner 194 as shown in FIG. 47B and, thereby, may be able to form a surface seal 198 against the interior wall of the cap body 104 in the interior cavity 106 thereof. The inner liner 194 may be fitted into the interior cavity 106 of the cap body 104 and held in the interior cavity 106 by a suitable friction fit or snap fit connection, or a mechanical connection. The bladder 1140 provides the surface seal 198 between the interior cavity 106 of the cap body 104 and the inner liner 194. The cap body 104 may further have a cylindrical section that extends beyond the bladder/liner combination that mechanically connects to the cylindrical body 30 and does not require a seal.

Figure 47C:
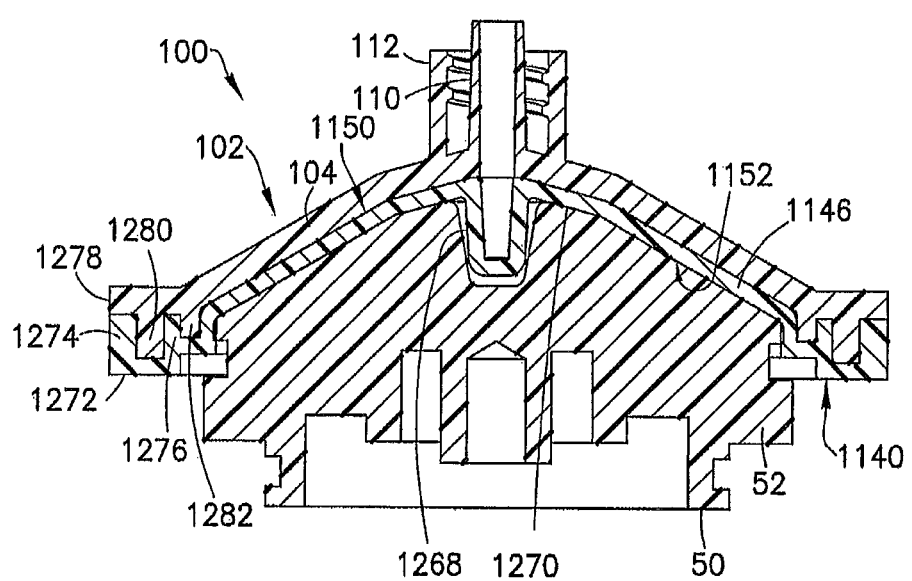

As a further alternative, as shown in FIG. 47C, the reusable cap 102 may have a cap body 104 with a co-injection molded bladder 1140, with the membrane portion 1146 having a central well portion 1268 surrounded circumferentially by a circumferential region 1270, which may be tapered as illustrated. As shown in FIG. 47B, the distal side 1150 of the membrane portion 1146 generally conforms to the internal shape of the interior cavity 106 of the cap body 104 and the opposing proximal side 1152, including the central well portion 1268 and surrounding tapered area or region 1270, defines a profile or shape that matches the profile of the distal portion 52 of the plunger element 50 as shown in FIG. 47C. Additionally, in FIG. 47C, an outer circumferential rim or flange 1272 of the bladder 1140 comprises a pair of circumferential ribs 1274, 1276 and an outer circumferential rim or flange 1278 of the cap body 104 comprises a pair of depending circumferential ribs 1280, 1282 that are adapted to engage the upstanding ribs 1274, 1276, respectively, during the co-injection molding process. As an alternative, the cooperating ribs 1274, 1280 and 1276, 1282 may be joined by other bonding methods such as ultrasonic welding, laser welding, adhesive bonding, and like techniques.

Figure 47D:
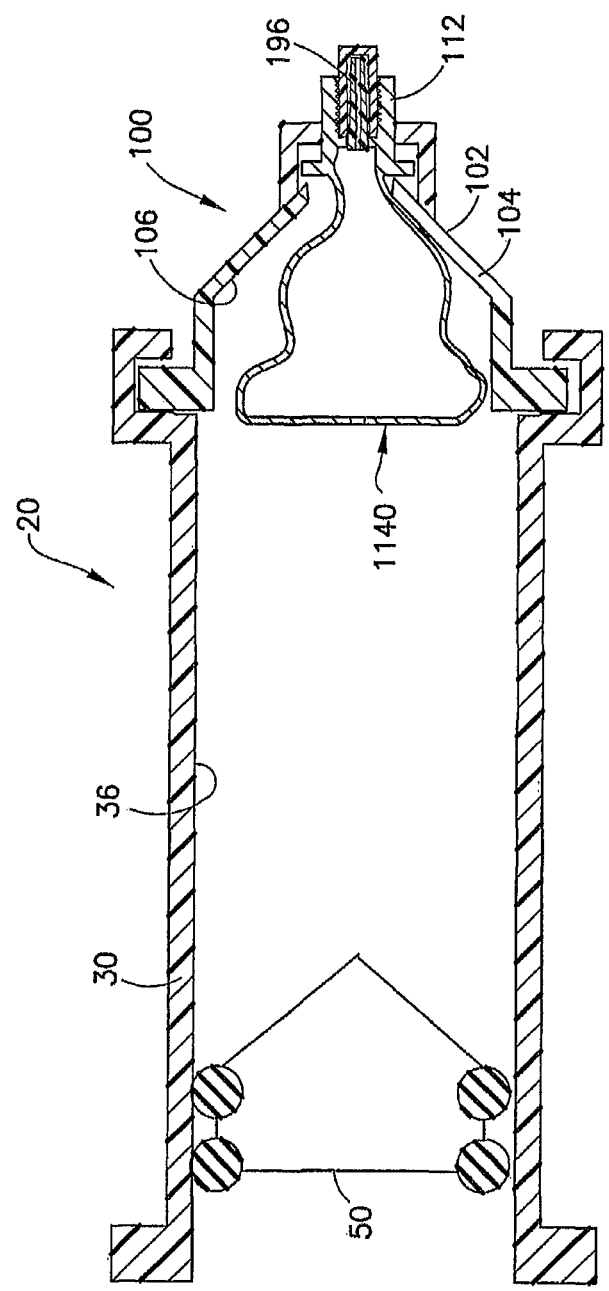

In FIG. 47D, the bladder 1140 is provided with a flexible bag-type membrane body that is co-injection molded with a rigid discharge conduit 196 that may seat within the discharge conduit 110 on the cap body 104 of the cap 102, as schematically illustrated in this figure which provides just the schematic details of the bladder syringe 20.

Figure 47F:
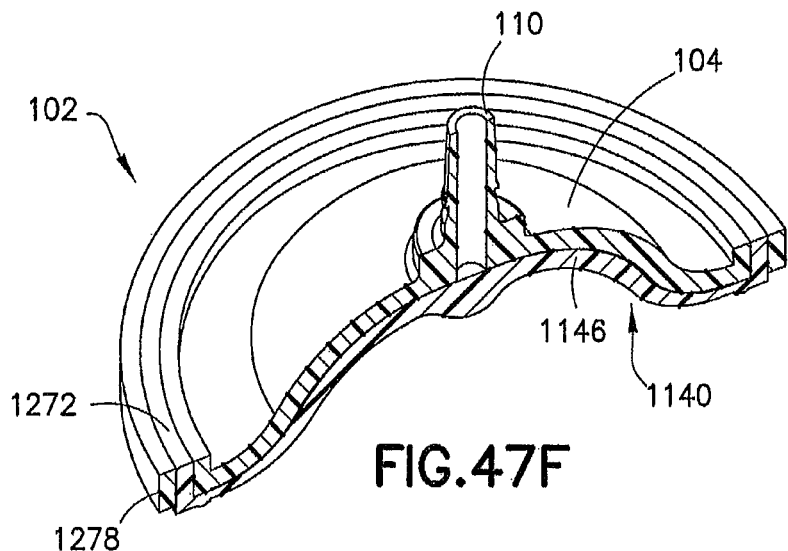
Figure 47E:
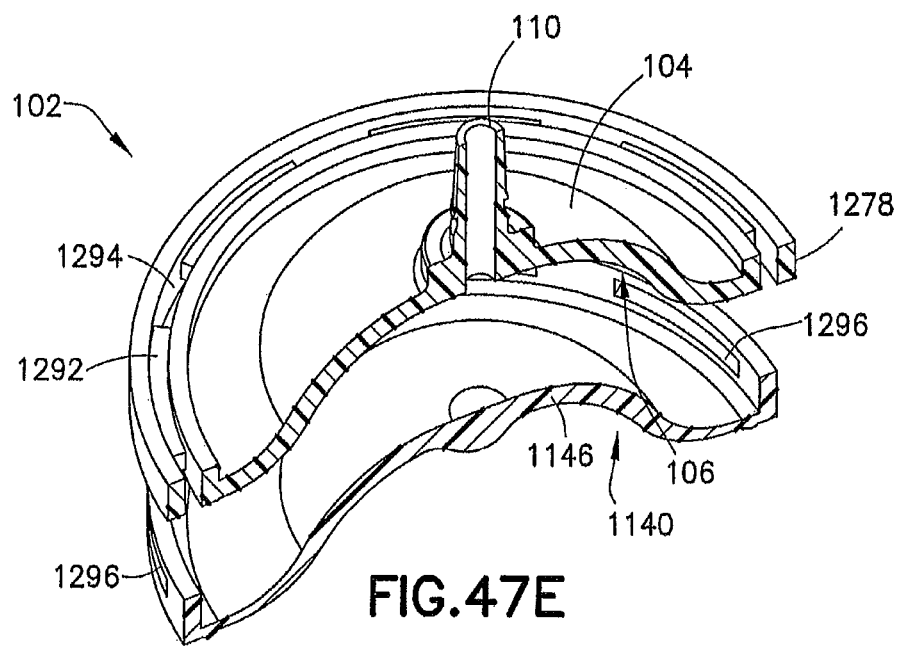

Referring to FIGS. 47E-47F, when over-molding the bladder 1140 to the cap body 104 of the cap 102, as in the embodiment shown in FIG. 47C, as an example, it is desirable prevent the membrane portion 1146 from sticking to the interior of the cap body 104. Thus, when a vacuum is generated in the cylindrical body 30 by action of the plunger element 50, the bladder 1140 may be easily pulled from the interior cavity 106 of the cap body 104 of the cap 102. However, it is also advantageous to have the outer circumferential rim or flange 1272 of the bladder 1140 fixed to the outer circumferential rim or flange 1278 of the cap body 104 so that the bladder 1140 does not separate from the cap 102 during shipping and handling. Also, it is also desirable to have the outer circumferential rim or flange 1272 of the bladder 1140 in solid contact or fixed with the outer circumferential rim or flange 1278 of the cap body 104 to prevent leaking during removal of the cap 102 from the cylindrical body 30 when fluid is present in the bladder 1140. In FIGS. 47E-47F an embodiment is shown that illustrates that during the over-molding of the bladder 1140, bladder material may flow from below the cap body 104 and into a recess 1292 in the outer circumferential rim or flange 1278 of the cap body 104 through through-holes 1294 defined in the outer circumferential rim or flange 1278, and this bladder material may reconnect with itself above the outer circumferential rim or flange 1278 in the recess 1292. The bladder 1140 is then locked mechanically in the regions between the through-holes 1294, with the added security of a chemical bond as the bladder 1140 reconnects with itself. Additional holes 1296 are shown in the bladder 1140 in FIG. 47E to illustrate where the material of the cap body 104 resides after the over-molding of the bladder 1140 to the cap body 104. FIG. 47E is an exploded view showing the bladder 1140 and the cap body 104 after over-molding so that manufacturing details, such as the through-holes 1294 and the additional holes 1296 may be viewed. The size, shape, and number of through holes 1294 and the recess 1292 may vary as needed to strike a balance between bladder retention and injection mold tooling complexity and part mold-ability.

In yet another variation, the bladder 1140 may be made of soft, highly elastic material, such as TPE, that is molded directly onto the retainer ring 140 that is assembled into the cap body 104 in the manner described previously in connection with FIGS. 13A-13B. The retainer ring 140 provides a rigid frame to support the bladder 1140 and can isolate the bladder 1140 from assembly torque during installation of the cap body 104 on the cylindrical body 30. The bladder 1140 and cap body 104 may be made of any of the materials detailed previously in this disclosure and the bladder 1140 is not limited to TPE as a choice of material. In this variation, it may also be possible to mold the retainer ring 140 and cap body 104 together as one component, wherein the retainer ring 140 and cap body 104 are connected together by, for example, a living hinge. The bladder 1140 may then be co-injection molded to the retainer ring 140 and all that is then required is to fold the retainer ring 140 into the cap body 104 (or vice versa) to complete the assembly of the bladder 1140 to the cap body 104. In the foregoing, a dust cap may also be attached with a living hinge to the cap body 104 so that the dust cap may flip open or closed on the discharge conduit 110 and end connector 112 like a flip top bottle lid, or the dust cap may be molded to be tethered to the discharge conduit 110 of the cap body 104. Several embodiments of a dust cap for the cap body 104 are described herein and may have the foregoing living hinge or tethered connections to the cap body 104.

Figure 48:
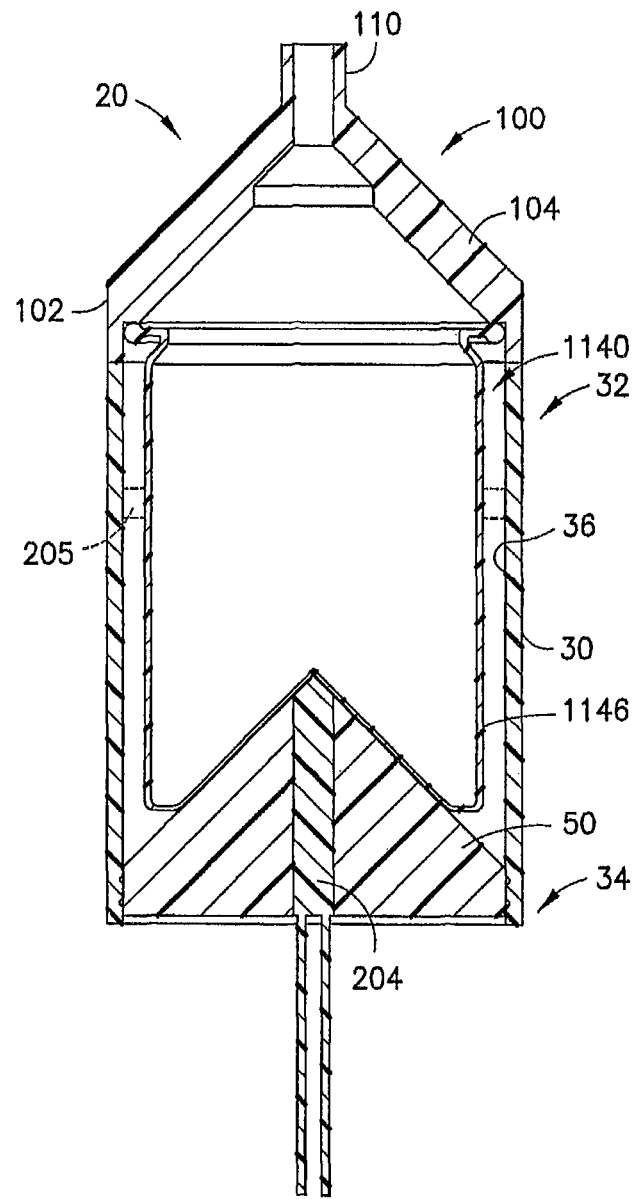
FIG. 48 is a schematic cross-sectional view of another embodiment of the bladder syringe that incorporates a sensor in the plunger element.
Figure 49:
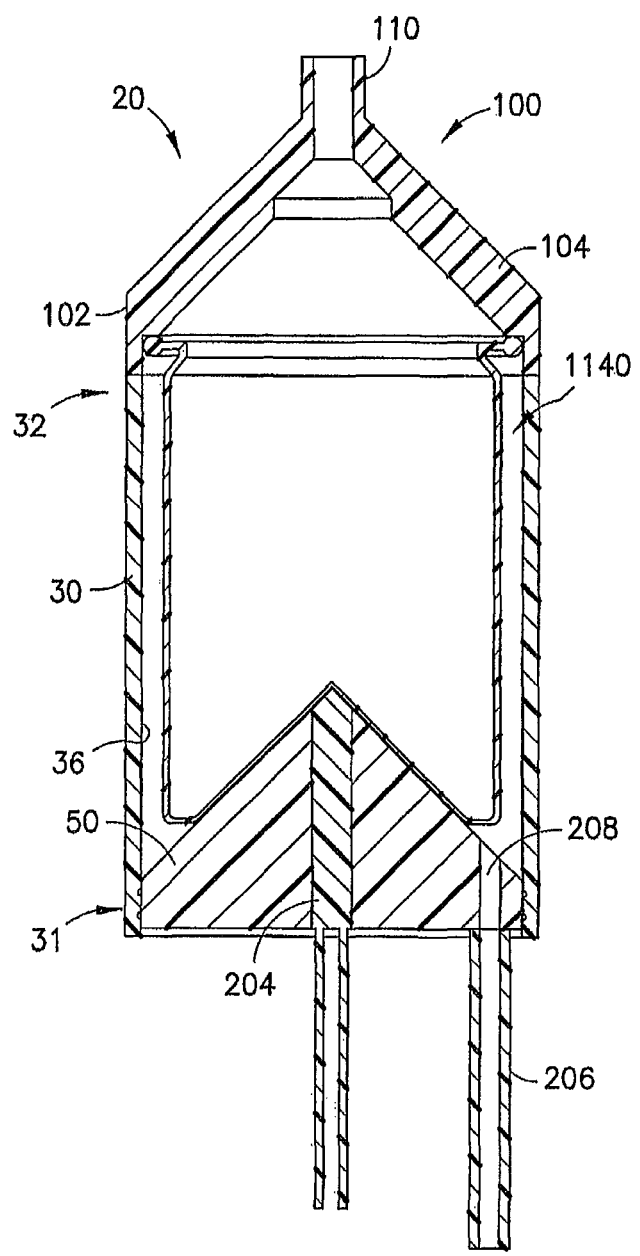
FIG. 49 is a schematic cross-sectional view of another embodiment of the bladder syringe that incorporates a sensor and a vacuum tube in the plunger element.

Referring further to FIG. 48, it is desirable to detect the presence of the cap-bladder assembly 100 on the cylindrical body 30 and/or the bladder 1140 in the cap body 104 of the assembly 100. For this purpose, as first shown in FIG. 48, a sensor 204 (in any of the forms discussed herein) may be provided coaxially in the plunger element 50 to determine whether the cap body 104 and/or bladder 1140 is present on the cylindrical body 30. In the embodiment of the plunger element 50 discussed in connection with FIG. 10A, the sensor 204 (in any of the forms discussed herein) may be disposed as part of the flat nub or ledge 139 or, alternatively, be disposed in the distal circular recess 138 (as shown in FIG. 10A) that surrounds the flat nub or ledge 139. In FIG. 48, and FIG. 49 discussed herein, the cap-bladder assembly 100, cylindrical body 30, and plunger element 50 are shown schematically to illustrate various sensor arrangements and details of the cap-bladder assembly 100, cylindrical body 30, and plunger element 50 are found in the foregoing. The coaxial sensor 204 may be an optical sensor that detects presence of the bladder 1140 and/or the cap body 104 on the cylindrical body 30 through the bladder 1140. In this embodiment, light is emitted from the optical sensor 204 and reflected back to the sensor 204 when the bladder 1140 is in place. The optical sensor 204 also may detect rupture of the bladder 1140 as fluid between the interface of plunger element 50 and the bladder 1140 causes a change in optical properties that is sensed by the optical sensor 204 (e.g., in the presence of air, no light is reflected back but in the presence of a liquid, light is reflected back). In addition to the foregoing, all or part of the interior wall 36 of the cylindrical body 30 and/or the plunger element 50 may be coated with a litmus coating that changes color in the presence of a liquid. In this variation, the optical sensor 204 may be adapted to identify the color change and send a signal indicating the presence of liquid in the cylindrical body 30 distal of the plunger element 50. As a further alternative, the membrane portion 1146 of the bladder 1140 and/or interior wall 36 of the cylindrical body 30 or the plunger element 50 may be coated with a color-changing chemical in the presence of liquid. If the bladder 1140 should leak or rupture, the color-changing chemical, similar to a dye-pack, changes color and this change is registered by the optical sensor 204. The material comprising the bladder 1140 may also incorporate the color-changing dye chemical during manufacturing. Any of the optically determined sensed conditions may also be detected by an external sensing device, such as external sensor device 260 described herein in connection with FIGS. 57-58. Moreover, the coating on the interior wall 36 of the cylindrical body 30, plunger element 50, or the bladder 1140 may be a chemical substance that generates gas bubbles, such as oxygen bubbles, in the presence of liquid that would change the optical properties in the cylindrical body 30 sufficiently to enable the optical sensor 204 to register and send a signal to the controller of the fluid injector 12. The optical sensor 204 (or external sensor device 260) may be a bubble detector as is known the medical field for detecting air bubbles in tubing.

In FIG. 48, the aforementioned full/partial litmus coating is represented as a litmus strip 205. Moreover, in the event of failure of the bladder 1140, leaking fluid will typically leak downward to the plunger element 50 and into the interior of the plunger element 50 via interconnecting passages 64, 66 to reach the check valves 82 (see FIGS. 1B and 4), and through the porous plug 134 (if present). The check valves 82 may be configured to create a low pressure drop so that, if the bladder 1140 breaks or leaks, the path of least resistance is through the check valves 82 and out the plunger element 50 into the fluid injector 12. The presence of fluid in the fluid injector 12 will be immediately noticeable to attendant medical personnel, and a fluid sensor may also be located in the fluid injector housing 18 to detect fluid leakage into the housing 18.

As an alternative, the sensor 204 may be an ultrasonic sensor that detects the presence of the cap body 104 on the cylindrical body 30 and/or detects the presence of the bladder 1140 in the cap-bladder assembly 100. The ultrasonic sensor 204 may further be used to detect whether there is proper contact between the membrane portion 1146 of the bladder 1140 and the plunger element 50 during filling. In this embodiment, sound waves are emitted from the ultrasonic sensor 204 and reflected back to the sensor 204 when the cap body 104 is in place. The ultrasonic sensor 204 also may detect rupture of the bladder 1140 as fluid between the interface of plunger element 50 and the bladder 1140 causes a change in medium properties (air/vacuum to liquid) between the plunger element 50 and bladder 1140 that is sensed by the ultrasonic sensor 204. Moreover, the ultrasonic sensor 204 may also be used to track the position of the bladder 1140 as it is being filled.

In addition to the foregoing, the sensor 204 in FIG. 48 may also be a mechanical type sensor in which the body of the sensor 204 is spring-loaded to extend distally a short distance from the plunger element 50 to the vicinity of the bladder 1140 when the cap body 104 is attached to the cylindrical body 30. Accordingly, as the cap-bladder assembly 100 is placed on the cylindrical body 30, the bladder 1140 makes physical contact with the mechanical sensor 204 and depresses the sensor 204 which provides a signal that the cap-bladder assembly 100 is present. Thus, the bladder 1140 actuates the mechanical sensor 204 during attachment of the cap-bladder assembly 100 and/or during filling of the bladder 1140 when the bladder 1140 extends and makes contact with the plunger element 50. In this embodiment, the mechanical sensor 204 may further be able to determine volume or pressure in the extended bladder 1140 when filled by the degree of physical contact between the bladder 1140 and the mechanical sensor 204. The mechanical sensor 204 desirably has a large surface area head, such as by forming a substantial portion of the distal portion 52 of the plunger element 50, and is backed by a spring with a low spring constant to avoid damage to the bladder 1140 during use. Such a mechanical sensor 204 with a large surface head may be found in U.S. Pat. No. 7,666,169 to Cowan et al. and is incorporated into a plunger element for a syringe; this patent is hereby incorporated herein by reference for this purpose. As an alternative, the plunger element 50 may be spring-loaded to operate as part of the mechanical sensor 204.

Furthermore, fluid dots (not shown) may be provided on the cylindrical body 30 as an indicator of fluid within the bladder syringe 20. Such fluid dots are well-known in the medical field, but because the cylindrical body 30 is intended to be reusable, in the present embodiment, the fluid dots may be darkened or black fluid dots when viewed in the presence of a liquid and would be immediately viewable by attendant medical personnel even from a distance.

Further, FIG. 49 illustrates a variation of the bladder syringe 20 shown in FIG. 48, wherein a vacuum tube 206 is connected to an external vacuum source (not shown) and to a through-port 208 in the plunger element 50. This external vacuum source (not shown) may be used to fill the bladder 1140. As an example, in use, an operator can position the plunger element 50 at any desired axial position in the bore 37 of the cylindrical body 30 and apply a vacuum to draw the bladder 1140, instead of using the seal of the plunger element 50 with the interior wall 36 of the cylindrical body 30 to create the vacuum.

As a further alternative, the sensor 204 in FIGS. 48-49 may further include, or alternatively be provided as, a fluid sensor 204 to detect any leakage of fluid from the bladder 1140 when filled with fluid, or a failure of the bladder 1140 such as a complete rupture thereof. Additionally, the coaxial sensor 204 in FIG. 49 may further include, or alternatively be provided as, a pressure sensor 204 that, in addition to detecting the presence of the bladder 1140, may be used to detect a leak in the bladder 1140 such as a partial or complete rupture thereof. The change in pressure in the cylindrical body 30 and physical separation of the bladder 1140 from the plunger element 50 is registered as a pressure change in the cylindrical body 30 by the sensor 204. The fluid sensor 204 may also be adapted to detect a trace chemical incorporated into the membrane portion 1146 of the bladder 1140 and/or on the interior wall 36 of the cylindrical body 30 that is activated in the presence of a liquid. In the case of a leak or rupture of the bladder 1140, the chemical may be activated and sensed by the fluid sensor 204 which provides a signal to the controller of the fluid injector 12 regarding a leakage/failure situation involving the bladder 1140.

Figure 50:
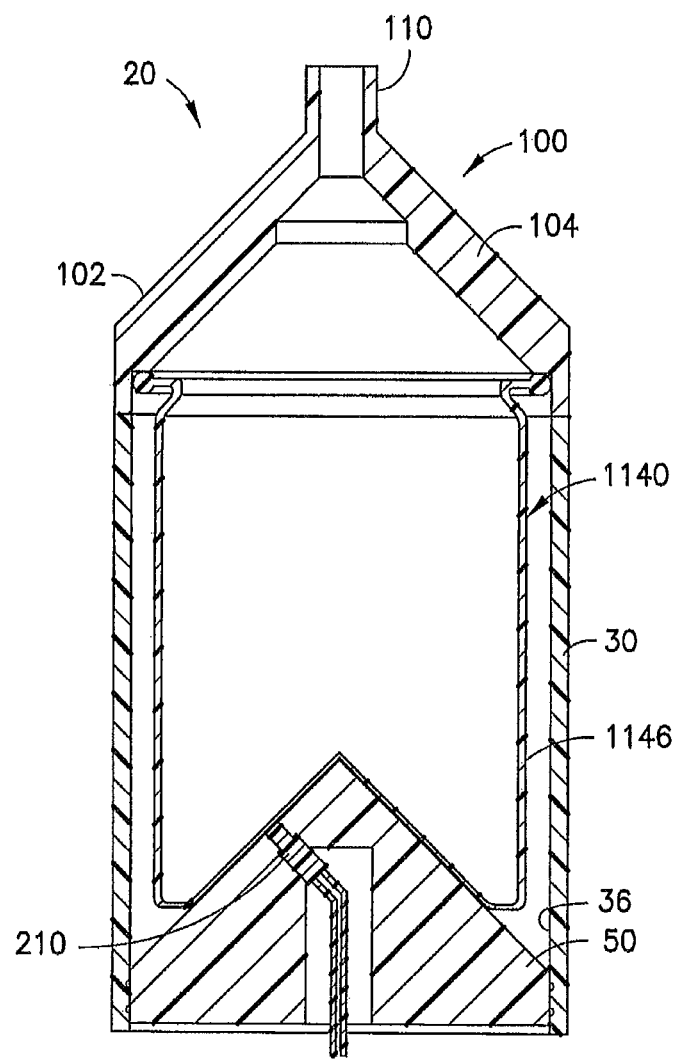
FIG. 50 is a schematic cross-sectional view of another embodiment of the bladder syringe that incorporates a pressure sensor in the plunger element.
Figure 51:
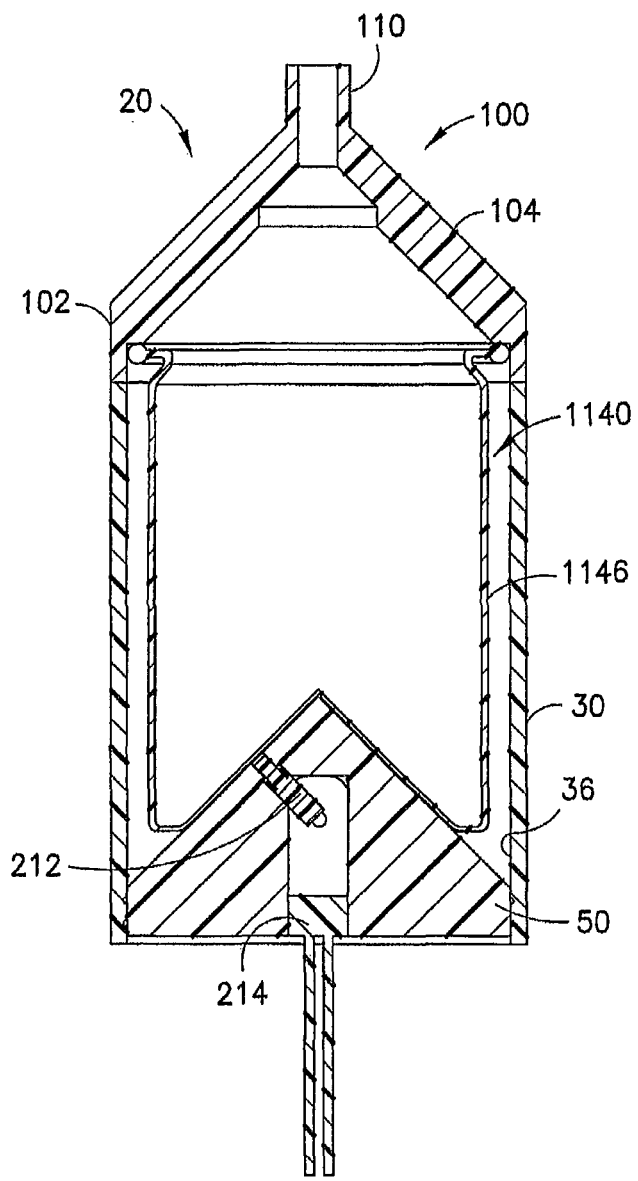
FIG. 51 is a schematic cross-sectional view of another embodiment of the bladder syringe that incorporates a vacuum-activated sensor in the plunger element.

Referring to FIGS. 50-51, a pressure sensor 210 may be provided in the plunger element 50. In FIGS. 50-51, the cap-bladder assembly 100, cylindrical body 30, and plunger element 50 are shown schematically to illustrate various sensor arrangements and details of the cap-bladder assembly 100, cylindrical body 30, and plunger element 50 are found in the foregoing. In one embodiment shown in FIG. 50, the pressure sensor 210 is a pressure transducer that monitors or indicates vacuum pressure in the cylindrical body 30 distal or forward of the plunger element 50 during filling of the bladder syringe 20 and communicates a signal to the controller associated with the fluid injector 12. In another embodiment shown in FIG. 51, the plunger element 50 may further include a vacuum popette 212 that extends to the outer surface of the plunger element 50 and actuates or moves when vacuum pressure is present in the cylindrical body 30 distal or forward of the plunger element 50 during filling of the bladder syringe 20. When this position change occurs, a coaxial sensor 214 disposed in the plunger element 50 registers or senses movement of the popette 212. For example, the sensor 214 may be embodied as an optical sensor that measures a change in position of the popette 212, which indicates the presence and level of vacuum pressure. The pressure sensor 210 may further make physical contact with the bladder 1140, as shown in FIG. 50, and the physical contact may register the pressure in the bladder 1140 when air is expelled and no differential pressure is present.

Figure 52:
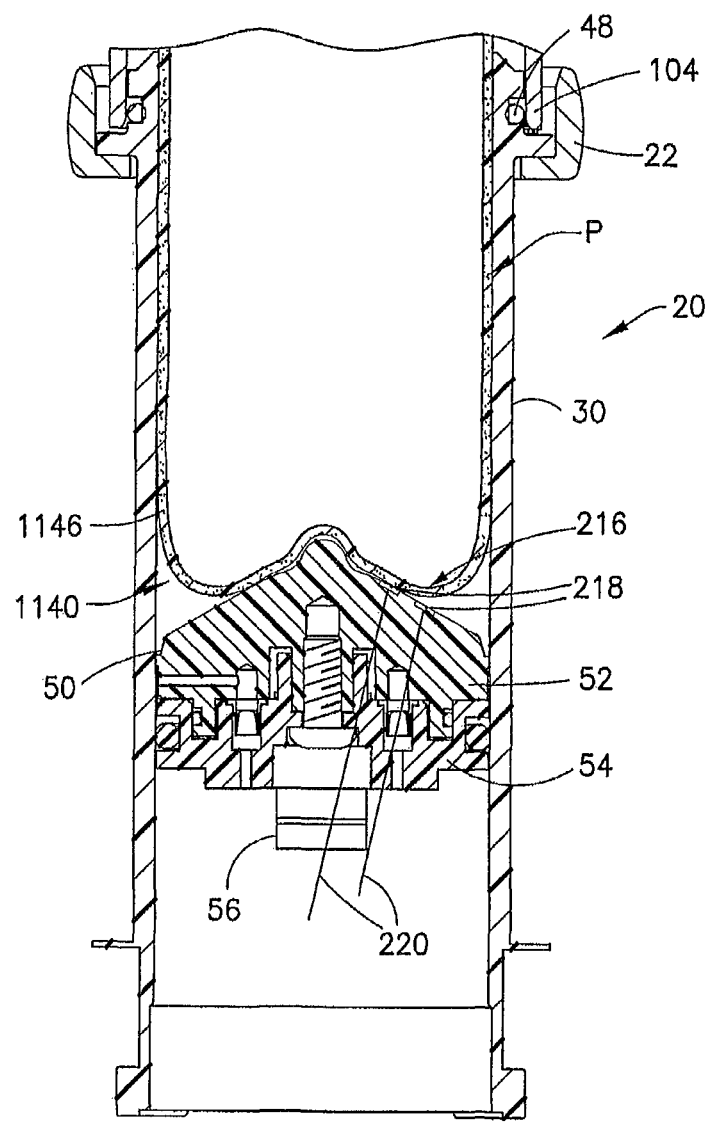
FIG. 52 is a partial cross-sectional view of the bladder syringe of FIGS. 1A-1B having a contact impedance measurement system for detecting presence of the cap-bladder assembly and/or leaking of a bladder in the cap-bladder assembly.

Referring to FIG. 52, a contact impedance measurement system 216 may be associated with the plunger element 50 to determine the presence of the bladder 1140 and/or whether there is a leak in the bladder 1140 of the cap-bladder assembly 100, or a complete rupture of the bladder 1140. Such a system 216 may include placing conductive elements or strips 218 on the distal portion 52 of the plunger element 50 which can detect the presence of liquid on the distal portion 52 which completes an electrical circuit between the conductive elements or strips or flex circuits 218 and, thus, a leak or rupture of the bladder 1140. Lead wires 220 may be routed through the plunger element 50 to connect to a controller associated with the fluid injector 12 so that leakage/rupture of the bladder 1140 may be detected by the controller and further operations involving the installed cap-bladder assembly 100 may be halted for replacement with a new cap-bladder assembly 100. The conductive elements 218 are adapted to detect the sharp rise in conductivity or capacitance associated with fluid from a leaking or burst bladder 1140. In another embodiment, the conductive elements or strips 218 may alternatively be electrical resistance sensors that measure electrical resistance of the bladder 1140. Embedded conductive particles P, as shown in FIG. 52, or a thin, easily breakable ductile wire (not shown) may be provided within the membrane portion 1146 of the bladder 1140 during manufacturing that create varying resistance readings depending on the amount of stretch as the particle density decreases with increased stretch. The electrical resistance elements or strips 218 detect the varying resistance when the bladder 1140 is expanded or contracted. The electrical resistance elements or strips 218 may be used to determine several pieces of information and communicate the same to the controller associated with the fluid injector 12. This information may include, for example, the amount of expansion or stretch of the bladder 1140 and, thus, fluid volume, the presence of the bladder 1140, and/or vacuum pressure within the cylindrical body 30 forward or distal of the plunger element 50. Furthermore, in case of a rupture of the bladder 1140, the electrical resistance element or strips 218 detect the sharp change in conductivity or impedance associated with the stretching of the conductive particles or conductive wire or the breakage of the conductive wire and register the same as a failure of the bladder 1140.

While the foregoing discussion provides the conductive elements, strips, or flex circuits 218 in association with the plunger element 50, these may be provided on the interior wall 36 of the cylindrical body 30 and which are embedded in the interior wall 36 to be flush. A suitable electrical lead connection may pass through the cylindrical body 30 to connect to the controller of the fluid injector 12. Furthermore, a radio-frequency identification (RFID) tag may be embedded into the material forming the bladder 1140 during manufacturing and, in the case of a leak or rupture of the bladder 1140, the RFID tag may activate or deactivate to indicate to the controller of the fluid injector 12 alerting to the leak/rupture.

Figure 53:
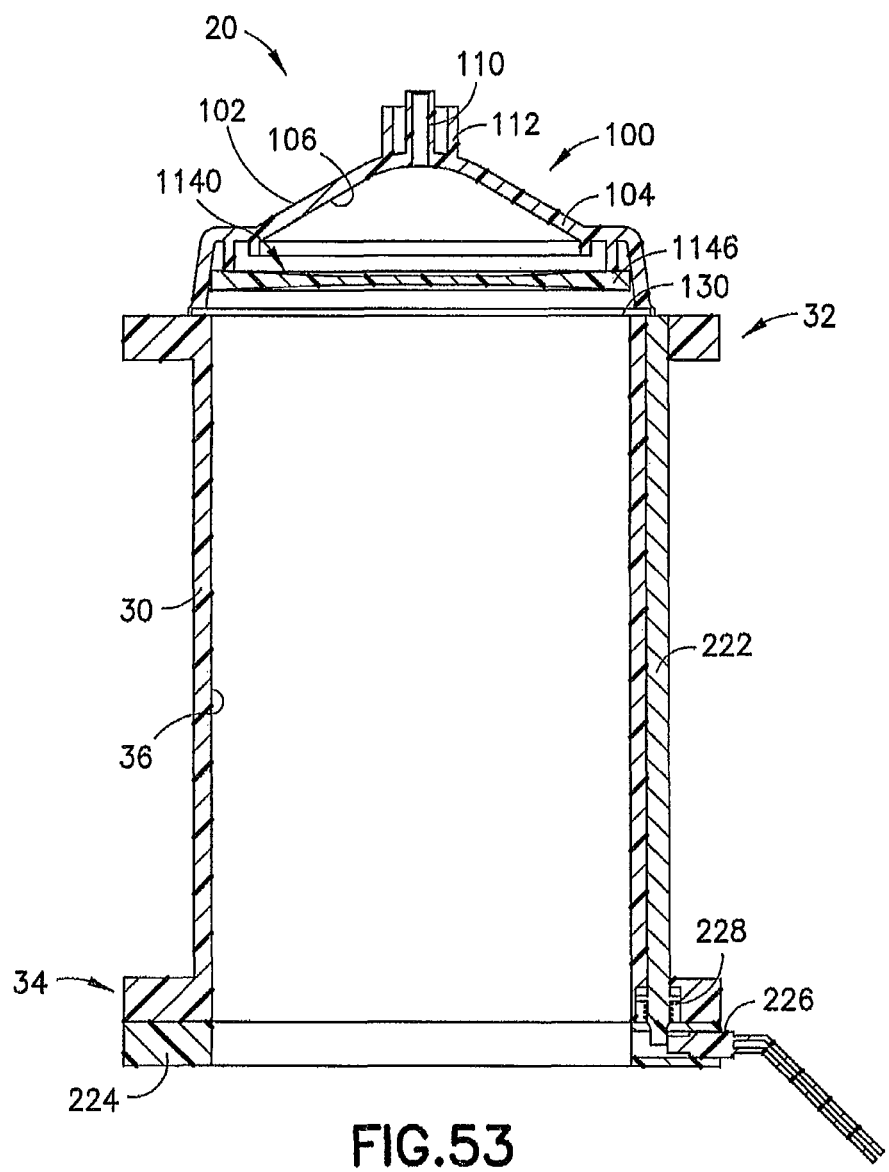
FIG. 53 is a schematic cross-sectional view of another embodiment of the bladder syringe having a sensing arrangement to mechanically sense the presence of the cap-bladder assembly on the cylindrical body of the bladder syringe.

Referring to FIG. 53, a sensing arrangement is provided to mechanically sense the presence of the cap-bladder assembly 100 on the cylindrical body 30. In this embodiment, a long pin 222 is supported between the distal and proximal ends 32, 34 of the cylindrical body 30. A sensor base 224 is attached to the proximal end 34 of the cylindrical body 30 and supports a mechanical sensor 226 that detects movement of the pin 222. The pin 222 may be spring-biased toward the distal end 32 of the cylindrical body 30 by a spring 228 as shown. As the cap-bladder assembly 100 is attached to the distal end 32 of the cylindrical body 30, the pin 222 is depressed against the mechanical sensor 226 by the cap body 104 of the cap-bladder assembly 100. The mechanical sensor 226 registers the presence of the cap-bladder assembly 100 and sends a signal to the controller associated with the fluid injector 12. In FIG. 53, the cap-bladder assembly 100 and cylindrical body 30 are shown schematically to illustrate various sensor arrangements and details of the cap-bladder assembly 100, cylindrical body 30, and plunger element 50 are found in the foregoing.

Figure 54:
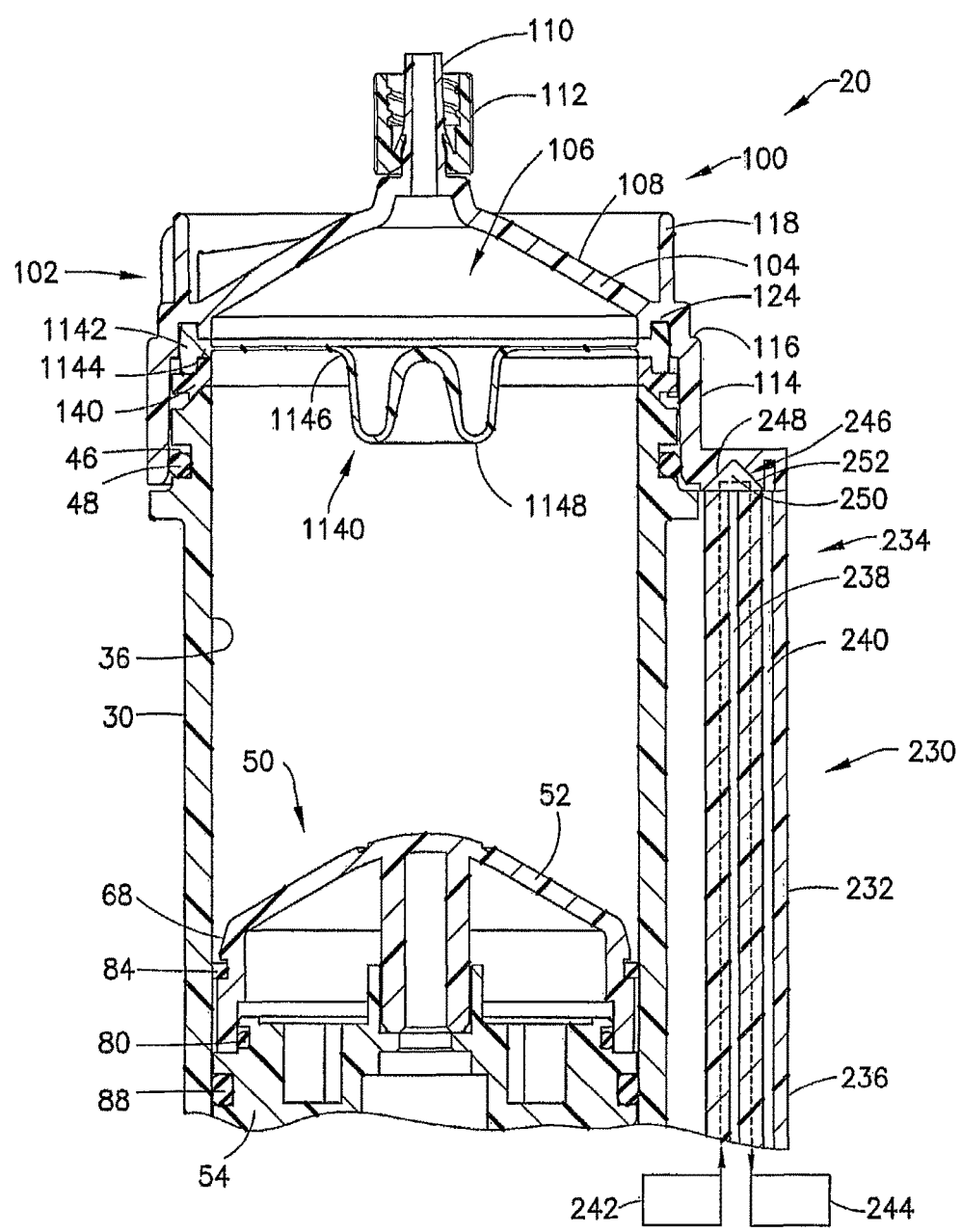
FIG. 54 is a partial cross-sectional view showing the bladder syringe of FIGS. 1A-1B with an additional light pipe assembly for detecting the presence of a cap-bladder assembly on the cylindrical body of the bladder syringe.
Figure 55:
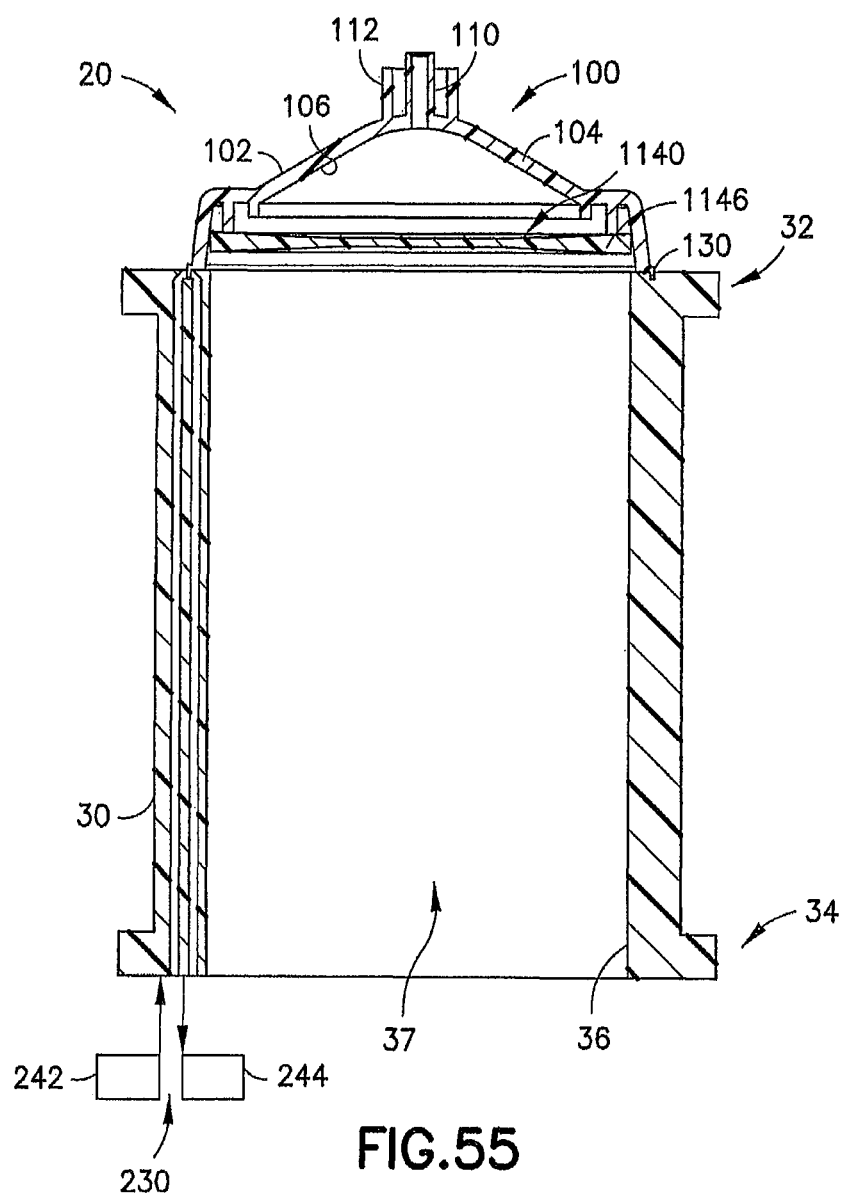
FIG. 55 is a schematic cross-sectional view of the bladder syringe of FIG. 54 with an alternative embodiment of the light pipe assembly.

Referring to FIG. 54, the bladder syringe 20 may have an external light pipe assembly 230 for detecting the presence of a cap-bladder assembly 100. The light pipe assembly 230 includes a light housing 232 having a distal end 234 and a proximal end 236 and carrying two light pipes 238, 240 extending between the distal and proximal ends 234, 236. The light housing 232 is desirably molded as part of the cylindrical body 30 and extends axially along the cylindrical body 30, but also may be separate from the cylindrical body 30 and secured thereto by any desirable mechanical arrangement. The light housing 232 carries two light pipes 238, 240 to carry light from a light emitter 242 and to a light receiver 244, respectively. The cap body 104 includes a reflector element 246 that extends radially outward from the cap body 104 to interface and connect with the distal end 234 of the light housing 232. The reflector element 246 has a first reflector 248, typically a 45° reflector, which directs the light beam from the light emitter 242 and is carried by the light pipe 238 across a gap 250 to a second reflector 252, typically a 45°reflector, which directs the return light beam to the opposing light pipe 240 which carries the light beam down the length of the light housing 232 to the light receiver 244. The presence of the cap body 104 completes the light circuit and this information may be utilized by the controller associated with fluid injector 12 to confirm the presence and proper installation of the cap-bladder assembly 100 on the bladder syringe 20. Proper installation of the cap-bladder assembly 100 on the bladder syringe 20 could also be accomplished by providing the light pipe assembly 230 in such a manner that interruption of a light beam by the cap body 104 would indicate the presence and proper installation of the cap-bladder assembly 100 on the bladder syringe 20. FIG. 55 shows a variation of the foregoing light pipe assembly 230 incorporated integrally into the sidewall of the cylindrical body 30 and reference may be made to FIG. 54 for the details of the light pipe assembly 230. In FIG. 55, the cap-bladder assembly 100 and cylindrical body 30 are shown schematically to illustrate various sensor arrangements and details of the cap-bladder assembly 100, cylindrical body 30, and plunger element 50 are found in the foregoing.

Figure 56:
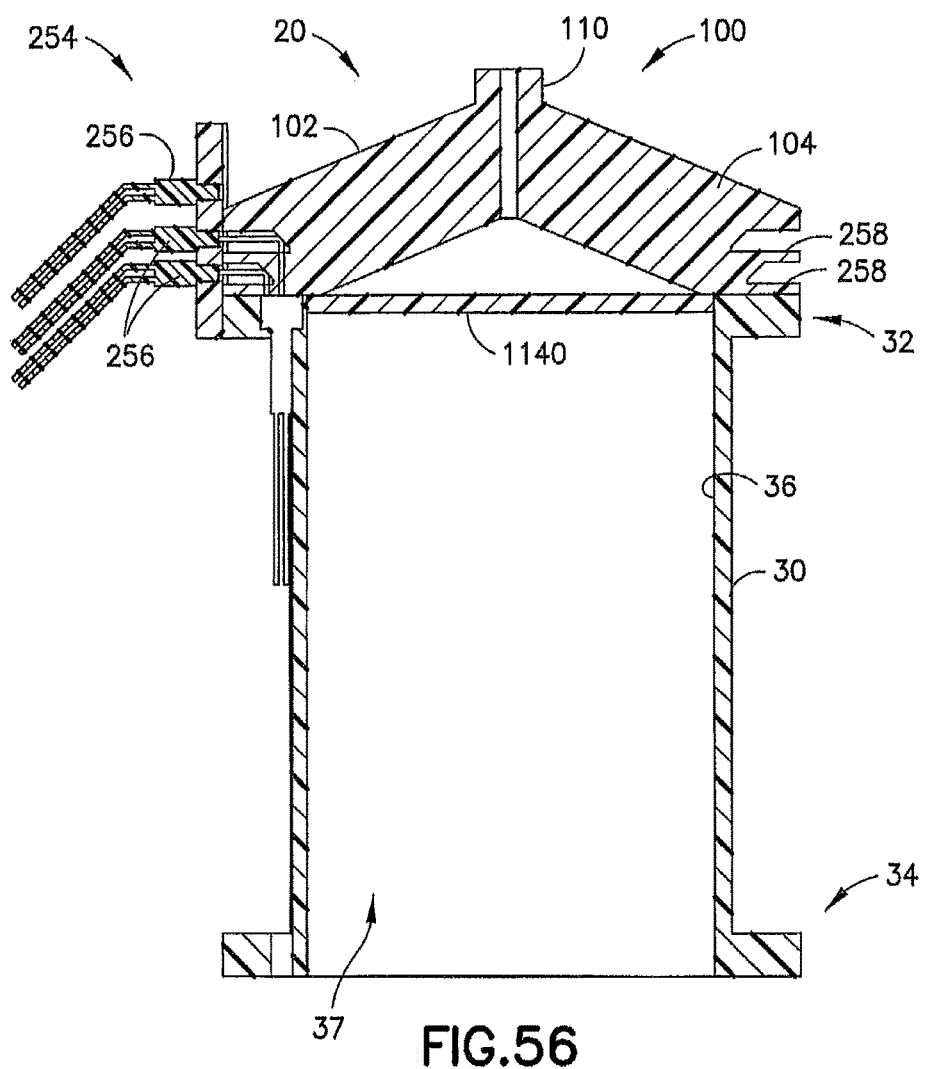
FIG. 56 is schematic cross-sectional view of another embodiment of the bladder syringe having an optical sensor array provided to read grooves in the cap body of the cap-bladder assembly on the cylindrical body of the bladder syringe.

Referring to FIG. 56, an optical sensor array 254 comprising a plurality of optical sensors 256 may be provided to read grooves 258 in the cap body 104 of the cap-bladder assembly 100. In this embodiment, the optical sensor array 254 may sense one or both of the size of the cap body 104 and presence of the cap-bladder assembly 100 on the cylindrical body 30 and sends signal(s) to the controller associated with the fluid injector 12 to convey this information to the controller, and a similar system for size sensing of a syringe may be found in U.S. Pat. No. 7,666,169 to Cowan et al., previously incorporated herein by reference. In FIG. 56, the cap-bladder assembly 100 and cylindrical body 30 are shown schematically to illustrate various sensor arrangements and details of the cap-bladder assembly 100, cylindrical body 30, and plunger element 50 are found in the foregoing.

Figure 57:
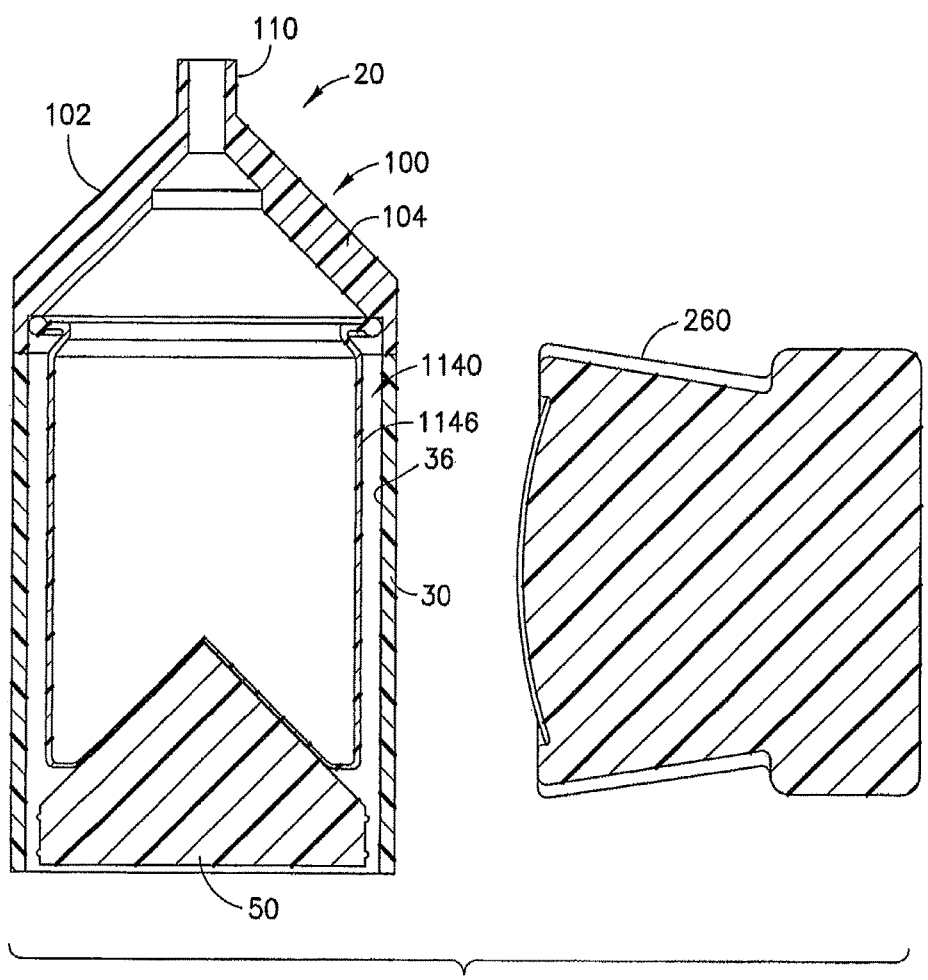
FIGS. 57-58 are respective schematic cross-sectional views of another embodiment of the bladder syringe in which an external sensor device is used to detect the presence and position of the bladder and/or to determine the volume of fluid present in the bladder, or other properties associated with the bladder.
Figure 58:
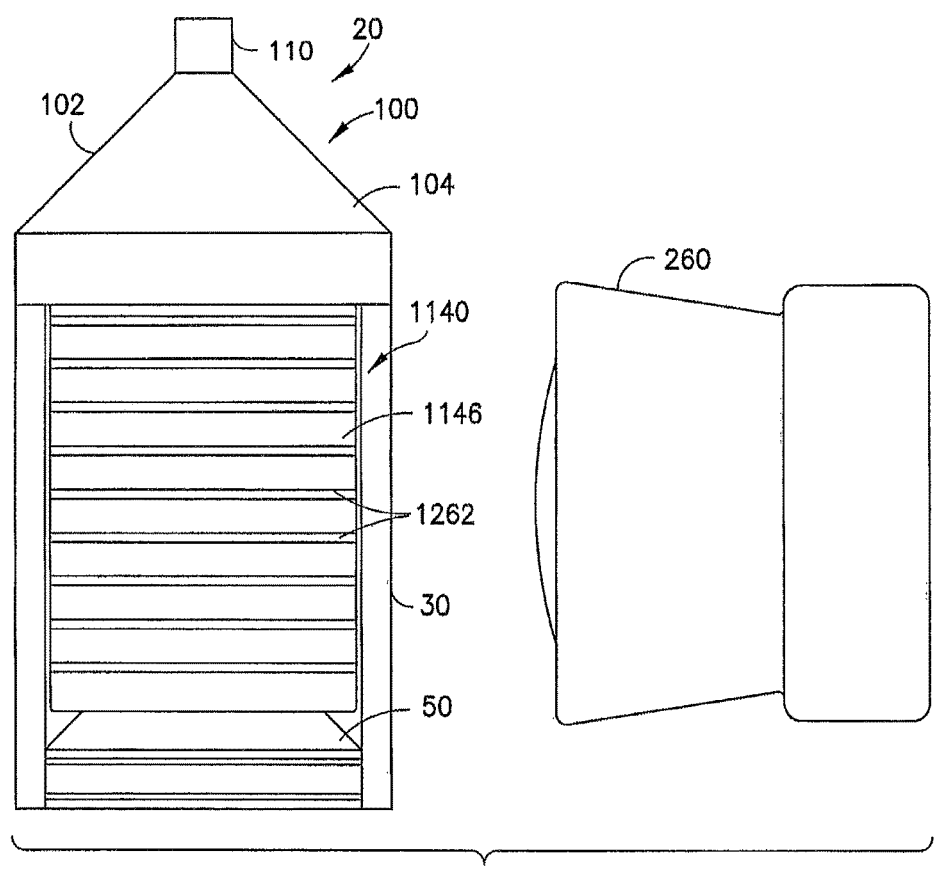

Referring to FIGS. 57-58, a sensor device 260 may be located external to the cylindrical body 30 to detect the presence and position of the bladder 1140 and/or to determine the volume of fluid present in the bladder 1140, or other properties associated with the bladder 1140. The external sensor device 260 may be an optical sensor device 260 that may be used to optically determine the presence and position of the bladder 1140 and/or to determine the volume of fluid present in the bladder 1140. The external sensor device 260 may also be used to sense a leak/rupture of the bladder 1140 as the position of the bladder 1140 changes abruptly when there is a complete rupture and not in sync with movement of the plunger element 50. The external sensor device 260 may also be adapted to read volume or other indicia markings 1262 on the bladder 1140, such as a bar code. The external optical sensor device 260 may alternatively be an ultrasound sensor device 260 that is used to check for liquid and air in the bladder 1140. As described previously, lines, grooves, or markings or other indicia 1100 may be provided in the top or distal side 1150 of the membrane portion 1146 of the bladder 1140 which provide a visual indication to attendant medical personnel of the bladder 1140 being filled with fluid and in a stretched state, and these lines, grooves, or markings 1100 may likewise be read by the external optical sensor device 260 as the bladder 1140 is stretched during filling. In case of failure of the bladder 1140, the external optical sensor device 260 would likewise register the failure. The markings 1100 may be used additionally for decorative purposes or to identify the source or origin of the cap-bladder assembly 100, and may further be a bar code.

Figure 59A:
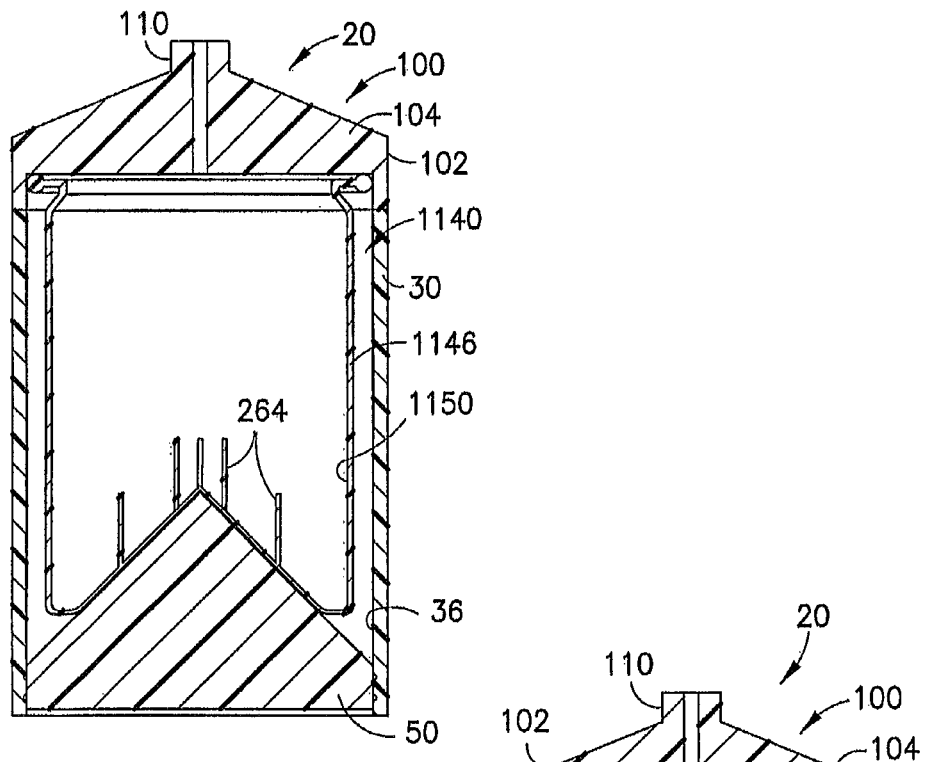
FIGS. 59A-59B are respective schematic cross-sectional views of another embodiment of the bladder syringe in which the bladder is provided with floating fibers.
Figure 59B:
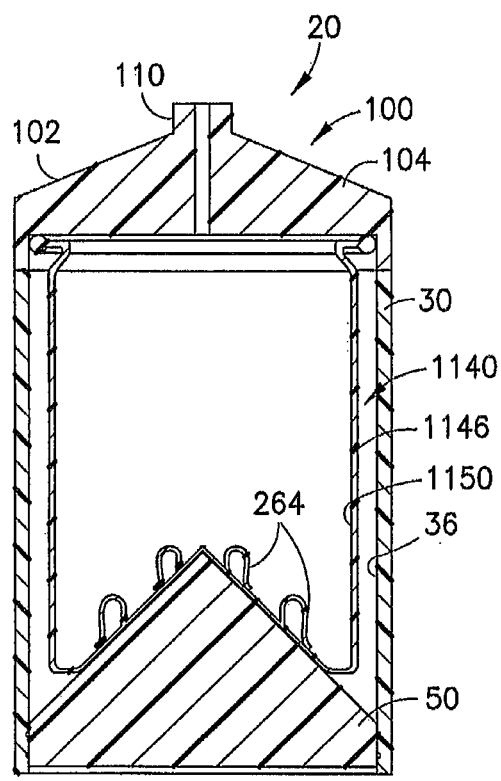

Referring to FIGS. 59A-59B, an embodiment is shown useful for visually determining when there is fluid in the filled bladder 1140. In FIGS. 59A-59B, the membrane portion 1146 of the bladder 1140 is provided with fibers 264 on the on the top or distal side 1150 which float in the presence of fluid, as shown in FIG. 59A. If no fluid is present, the fibers curl over or lie flat against the top or distal side 1150 of the membrane portion 1146 of the bladder 1140, as shown in FIG. 59B. One or more of the sensors described previously, such as the optical sensor 204 and the external optical sensor device 260 may be used as an optical detector to sense the presence of the fibers 264. In FIGS. 59A-59B, the cap-bladder assembly 100, cylindrical body 30, and plunger element 50 are shown schematically to illustrate various sensor arrangements and details of the cap-bladder assembly 100, cylindrical body 30, and plunger element 50 are found in the foregoing.

Figure 60A:
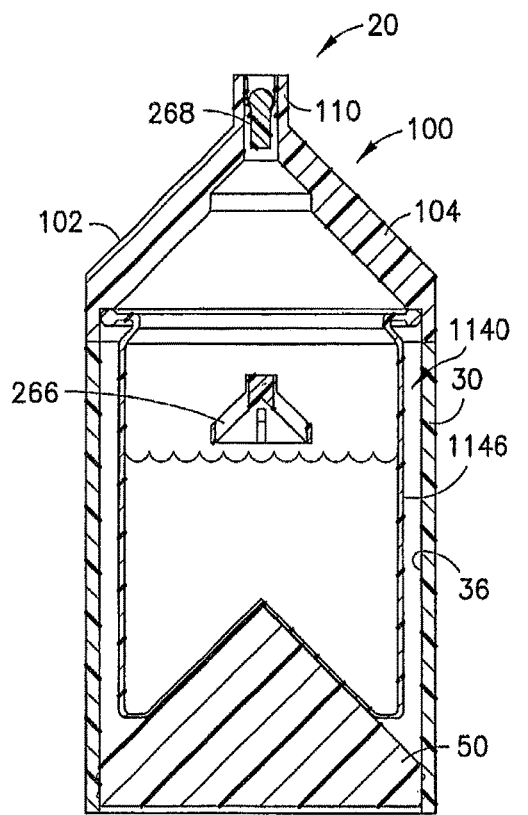
FIGS. 60A-60B are respective schematic cross-sectional views of another embodiment of the bladder syringe in which a floating actuator is provided inside the cap-bladder assembly and which only allows fluid injection if fluid is present in the bladder.
Figure 60B:
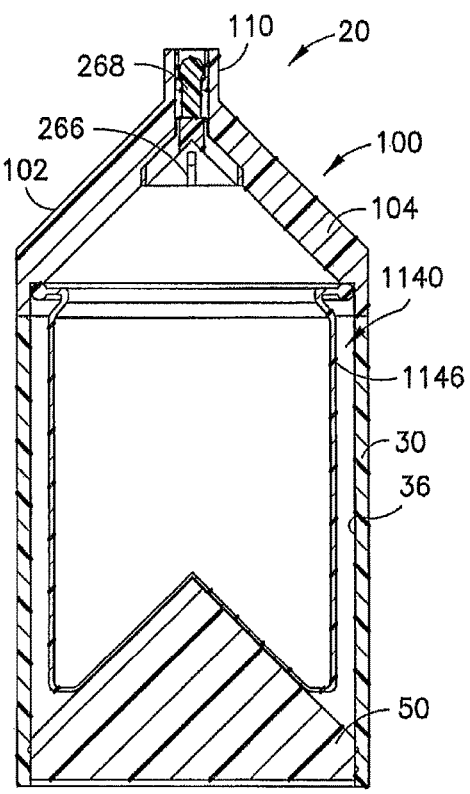

Referring to FIGS. 60A-60B, a floating actuator 266 may be provided inside the cap body 104 which only allows fluid injection if fluid is present in the bladder 1140. In this embodiment, a check valve 268 may be provided in the discharge conduit 110 of the cap body 104 that is normally closed to fluid flow outward from the bladder syringe 20. The outlet check valve 268 permits fluid to enter the bladder syringe 20. The outlet check valve 268 is overridden by the floating actuator 266. The floating actuator 266 comes into contact with the outlet check valve 268 to override the check valve when the bladder 1140 is filled with fluid, as shown in FIG. 60B. Otherwise, the outlet check valve 268 remains closed and prevents the ejection of fluid, either liquid or air, from the bladder syringe 20. In FIGS. 60A-60B, the cap-bladder assembly 100, cylindrical body 30, and plunger element 50 are shown schematically to illustrate various sensor arrangements and details of the cap-bladder assembly 100, cylindrical body 30, and plunger element 50 are found in the foregoing.

Figure 61:
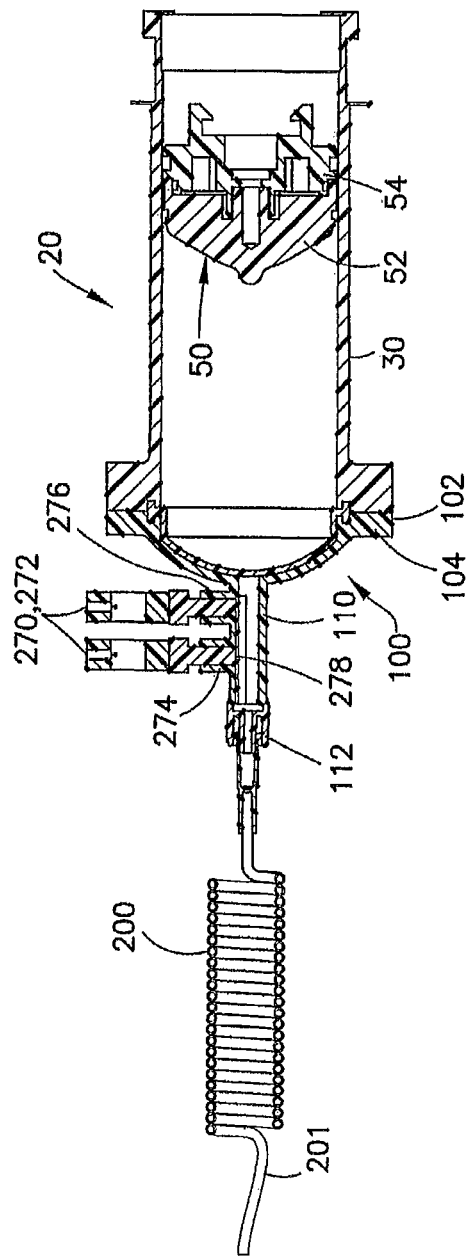
FIG. 61 is a schematic cross-sectional view of the bladder syringe of FIGS. 1A-1B showing the bladder syringe with a fluid transfer set and further having a flow regulation and monitoring capability.

Referring to FIG. 61, the bladder syringe 20 is illustrated with the disposable fluid path or set 200, discussed previously, which is connected to the threaded end connector 112 at the end of the discharge conduit 110 of the cap body 104. The disposable fluid set 200 may include tubing 201 for delivering fluid to a patient and this tubing 201 may include additional fluid carrying arrangements (not shown) for placing the bladder syringe 20 in fluid communication with one or more bottles or bags containing desired injection fluid. With respect to FIG. 61, it has been observed that variations in the volume of entrapped air between the plunger element 50 and the bladder 1140 may cause inaccuracies in fluid delivery. When air is present between the plunger element 50 and the bladder 1140, the initial fluid delivery lags while this air is compressed. After the air is compressed, the volume flow rate behaves as it would in a positive displacement syringe (e.g., a typical syringe used in power fluid injectors). To adjust for the foregoing inaccuracies, as shown in FIG. 61, the bladder syringe 20 may be mated with two pressure transducers 270, 272, for example, by associating the pressure transducers 270, 272 with the discharge conduit 110 of the cap body 104. In particular, the bladder syringe 20 is configured to have the cap-bladder assembly 100 mated with two pressure transducer sensing ports 274, 276 placed on a membrane 278 provided in the discharge conduit 110 of the cap body 104. The pressure transducer sensing ports 274, 276 accept and support the pressure transducers 270, 272. During an injection, while fluid is flowing from the bladder syringe 20 through the tubing 201, there is a pressure difference between the two transducers 270, 272. Using the pressure difference between the transducers 270, 272, the volume flow rate can be calculated. The controller of the fluid injector 12 compares the calculated flow rate with the programmed flow rate and varies the speed of the piston element 14 as needed to achieve the programmed flow rate and volume delivery. This control method minimizes the effects of the air trapped between the bladder 1140 and plunger element 50 since the fluid injector 12 compensates for lower flows (e.g., while the air is being compressed) by increasing the speed of the plunger element 50 interfaced with the piston element 14. The foregoing pressure sensing arrangement using two pressure transducers 270, 272 may be utilized with any syringe having a distal discharge conduit similar to the discharge conduit 110 of the cap body 104 and is not limited to use with bladder syringe 20. Using the arrangement in FIG. 61, the rate and time required to reach a desired pressure can be tracked as can pressure differential over time to determine flow rate.

In FIG. 61, the membrane 278 could also be adapted to provide a known restriction in the outlet path of the bladder syringe 20, such that a known pressure would be required to overcome the restriction. If the fluid injector 12 applied a Fill/Prime sequence to fill the bladder syringe 20 with fluid, the pressure sensing arrangement shown in FIG. 61 may be used to measure the pressure in the discharge conduit 110 of the cap body 104, and the controller associated with the fluid injector 12 can track the rate and time it takes to achieve a desired pressure. If the bladder syringe 20 is filled with a liquid (e.g., an incompressible fluid), the rate and time needed to arrive at the desired pressure should be short and close to instantaneous. If air (e.g., a compressible fluid) is present, there will be a gradual ramp-up in pressure. The controller associated with the fluid injector 12 can track rate and time required to reach the desired pressure and can interpolate if there is air in the bladder syringe 20.

Referring to FIGS. 62A-62B, the interior wall 36 of the cylindrical body 30 and/or the interior cavity 106 of the cap body 104 of the cap 102 in the cap-bladder assembly 100 may be frosted as represented by the alternating shaded lines or regions 298 in FIG. 62A which, when exposed to liquid, becomes clear as represented in FIG. 62B. The frosting may be fine surface texture on the fluid side of the cylindrical body 30 and/or cap body 104. This fine surface texture would be such that it affects light transmission by diffusing light in the presence of air and would not affect light transmission in the presence of a liquid as the liquid fills-in the fine surface texture with liquid and becomes more transparent. The frosted fine surface texturing may also be provided on the distal portion 52 of the plunger element 50 as well. The frosted fine surface texturing may also be provided on any internal surface of a syringe and/or plunger in accordance with this disclosure such as a syringe used in the fluid injector 12 shown in FIG. 7 described previously, or any fluid conveying device such as a pump body, tubing set, or valve body to indicate when liquid is present on the textured surface on the body.

Referring to FIGS. 63A-63B, a sensor array 300 may be provided in the bore of the cylindrical body 30 and on the interior wall 36 thereof in this embodiment of the bladder syringe 20. The sensor array 300 is desirably embedded into the interior wall 36 of the cylindrical body 30. The sensor array 300 may be a capacitive sensor array 300 for determining the position of the bladder 1140 within the cylindrical body 30 during filling and, hence, for determining volume of fluid present in the bladder 1140. The sensor array 300 may further be adapted for linear resistive and/or impedance measurement of the position of the bladder 1140 within the cylindrical body 30 during filling and, hence, for determining volume of fluid present in the bladder 1140. Moreover, the sensor array 300 may further be adapted for capacitive or radio-frequency (RF) impedance measurement of the position of the bladder 1140 within the cylindrical body 30 during filling and, hence, for determining volume of fluid present in the bladder 1140. Furthermore, the sensor array 300 may further be adapted for ultrasonic measurement of the position of the bladder 1140 within the cylindrical body 30 during filling and, hence, for determining volume of fluid present in the bladder 1140. The cap 102 of the cap-bladder assembly 100 is omitted in FIGS. 63A-63B as are specific details of the connection/interaction of the cap-bladder assembly 100 with the cylindrical body 30 for simplicity. The positional and/or volume information regarding the bladder 1140 may be communicated by the sensor array 300 to the controller of the fluid injector 12 for controlling operation of the fluid injector 12. As another alternative, the lines, grooves, or markings 1100 on the bladder 1140, as shown in FIG. 12A discussed previously, or indicia markings 262 discussed previously in connection with FIG. 58 may comprise one part of a radio-frequency (RF) or capacitive circuit, and the second part of this circuit may be part of the sensor array 300, and a sensed change of impedance or capacitance in this circuit is indicative of leakage or failure of the bladder 1140. As a further alternative, the lines, grooves, or markings 1100 on the bladder 1140, as shown in FIG. 12A discussed previously, or indicia markings 262 discussed previously in connection with FIG. 58 may be conductive and, as the bladder 1140 expands during filling, reach the sensor array 300, and the sensor array 300 detects resistance changes along the bladder 1140; a sensed rapid change in this resistance is indicative of leakage or failure of the bladder 1140.

Figure 64:
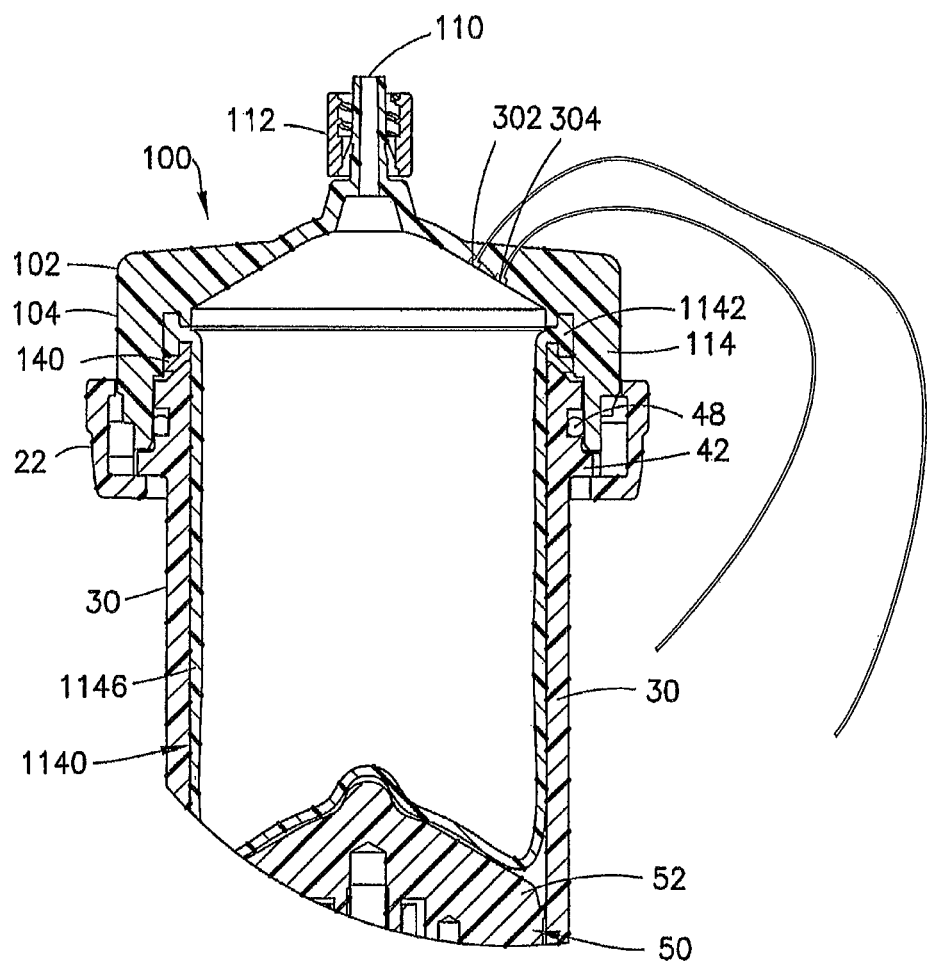
FIG. 64 is a cross-sectional view of the bladder syringe of FIGS. 1A-1B having two (2) sensor elements in the cap of the cap-bladder assembly.

Referring to FIG. 64, fluid detection for fluid in the cap 102 of the cap-bladder assembly 100 may also be provided by devices associated with the cap body 104. In FIG. 64, two (2) electrical leads 302, 304 may be provided in the cap body 104 to read the electrical resistance between the leads. If air alone is present, the resistance is infinite and in the presence of a conductive liquid the, resistance drops. This change in resistance is registered by the controller of the fluid injector 12 and indicates that liquid is present in the interior cavity of the cap body 104. One or both of the electrical leads 302, 304 may alternatively be an electrode and a second electrode may be formed by conductive material placed on the interior wall 36 of the cylindrical body 30 and/or on the plunger element 50 and an amp meter is connected to the electrodes operating at a low, patient-safe current. In the case of a leak or failure of the bladder 1140, a current larger than a threshold current indicates a leak or rupture of the bladder 1140.

Figure 65:
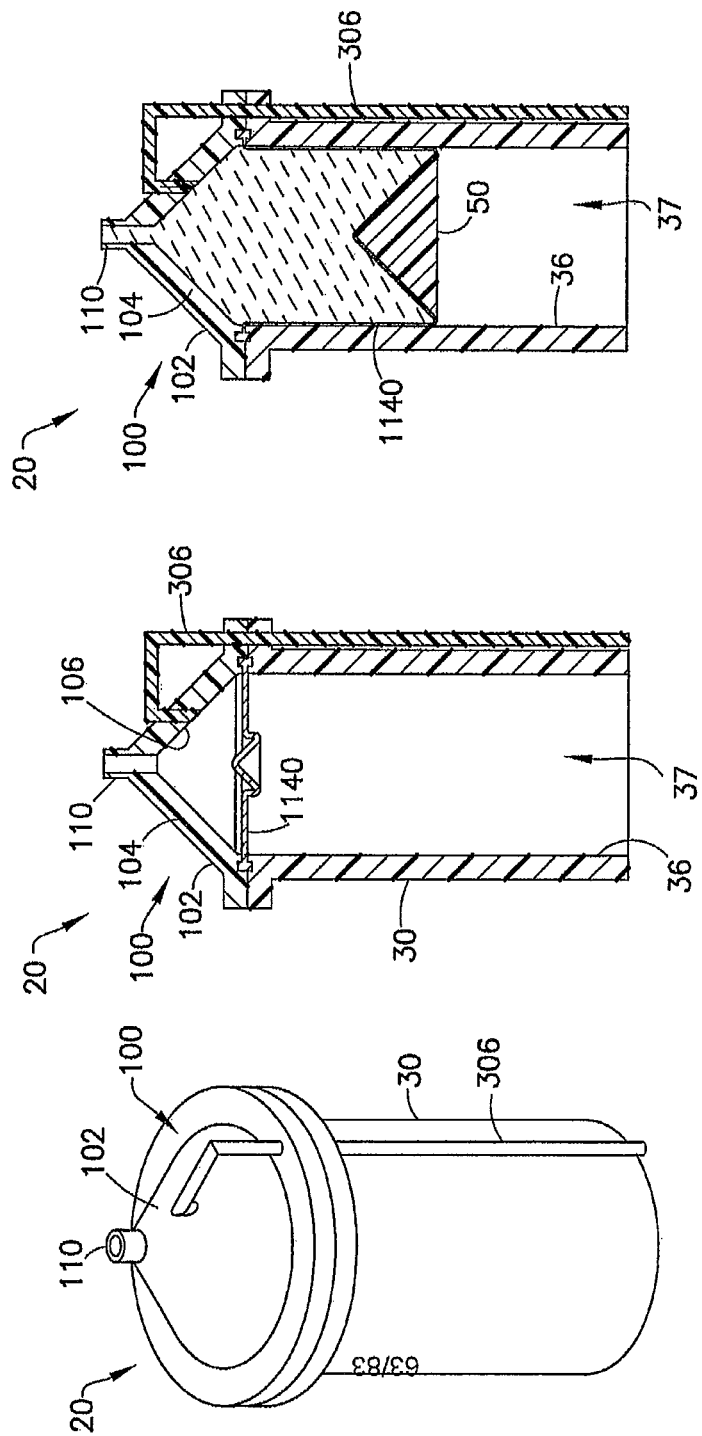
FIGS. 65A-65C are a perspective and two cross-sectional views, respectively, of another embodiment of the bladder syringe in which the cap-bladder assembly has an optical detection assembly that detects light reflectance changes in the presence of fluid in the cap of the cap-bladder assembly.

Referring to FIGS. 65A-65C, another method of fluid detection for fluid in the cap 102 of the cap-bladder assembly 100 comprises optical detection using a light pipe 306 that detects light reflectance changes in the presence of fluid in the cap body 104 of the cap 102. The light pipe 306 conducts light from an external light source, such as located in the housing 18 of the fluid injector 12 and conducts the light to the cap body 104 where the light enters into the cap body 104 at such an angle that the light would be trapped in the light pipe 306 and reflected back to the fluid injector 12 in the presence of air. In the presence of air, as shown in FIG. 65B, the difference between the index of refraction of air and the plastic cap body 104 and the exit angle would be so high that the light would be internally reflected inside the light pipe 306. When liquid is present, as shown in FIG. 65C, the index of refraction is closer to that of the plastic cap body 104 and the light is able to escape, and there is no internal reflection returning to the fluid injector 12. In FIGS. 65A-65B, the cap-bladder assembly 100, cylindrical body 30, and plunger element 50 are shown schematically to illustrate various sensor arrangements and details of the cap-bladder assembly 100, cylindrical body 30, and plunger element 50 are found in the foregoing.

Figure 66:
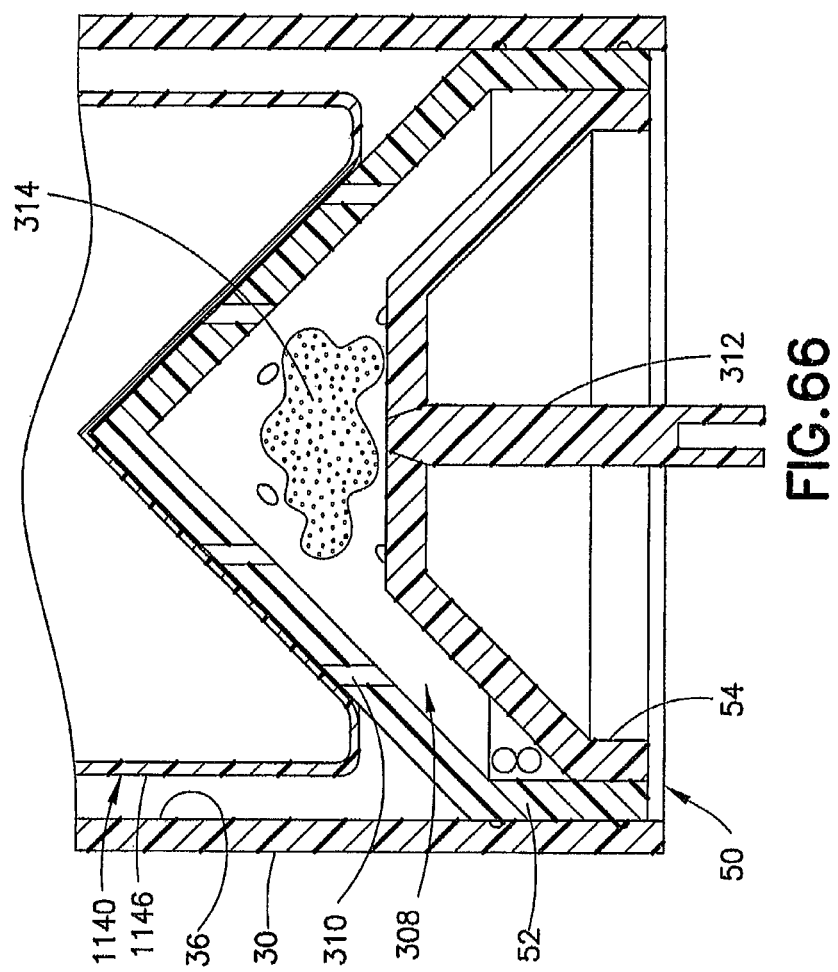
FIG. 66 is a schematic cross-sectional view of another embodiment of the bladder syringe in which the plunger element has a hollow cavity or well.

Referring to FIG. 66, another embodiment of the bladder syringe 20 is shown that incorporates a plunger element 50 in which a hollow cavity or well 308 is provided between the distal portion 52 and the proximal portion 54 of the plunger element 50. The plunger well 308 is in fluid communication with the bore of the cylindrical body 30 by a plurality of apertures 310 in the distal portion 52 of the plunger element 50. In the event the bladder 1140 leaks or ruptures, fluid enters the plunger well 308 via the apertures 310 and, for example, contacts a fluid sensor 312 in the proximal portion 54 of the plunger element 50. The fluid sensor 312 may, for example, register fluid upon the completion of connection. Such an electrical connection may result, for example, by providing the conductive elements 218 described previously in the plunger well 308. Fluid detection in the plunger well 308 using the fluid sensor 312 may be accomplished by any of the foregoing described techniques, such as optical, ultrasonic, electrical connectivity completion, fluid sensor, etc. If desired, the proximal portion 54 of the plunger element 50 may be adapted for limited movement relative to the distal portion 52, and this movement creates the plunger well 308 and, further, causes a vacuum in the plunger well 308 that pulls in fluid into the plunger well 308. The plunger well 308 may contain an absorbent material 314 that is suitable to disperse fluid and allow one or more sensors in the plunger well 308 to register the presence of fluid and a leak or rupture of the bladder 1140.

Figure 67:
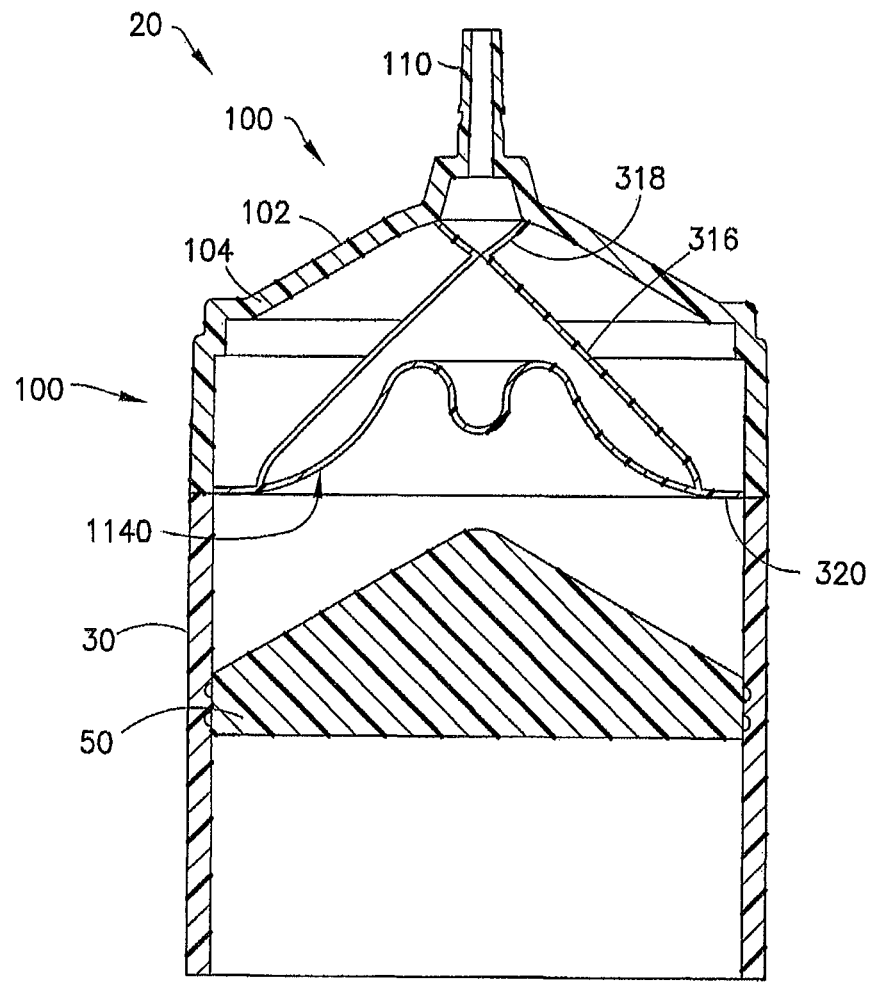
FIG. 67 is a schematic cross-sectional view of another embodiment of the bladder syringe in which a flapper or duckbill valve is incorporated into the cap of the cap-bladder assembly.

In FIG. 67, another embodiment of the bladder syringe 20 is shown that incorporates a flapper or duckbill valve 316 that is attached to the cap 102 of the cap-bladder assembly 100. The flapper or duckbill valve 316 is attached by one circumferential connection 318 to the cap body 104 in the interior cavity 106 thereof and is adapted to mechanically release from the cap body 104 under the stress induced when the bladder 1140 ruptures. As illustrated in FIG. 67, the flapper or duckbill valve 316 is further connected by a second circumferential connection 320 to the bladder 1140 so that when the bladder 1140 ruptures, the flapper or duckbill valve 316 is released and halts any fluid flow from the bladder syringe 20. The controller of the fluid injector 12 automatically experiences a sharp rise in back pressure and ceases operation. Details of the cap-bladder assembly 100, cylindrical body 30, and plunger element 50 are omitted in FIG. 67 and the components are illustrated schematically only.

Figure 68:
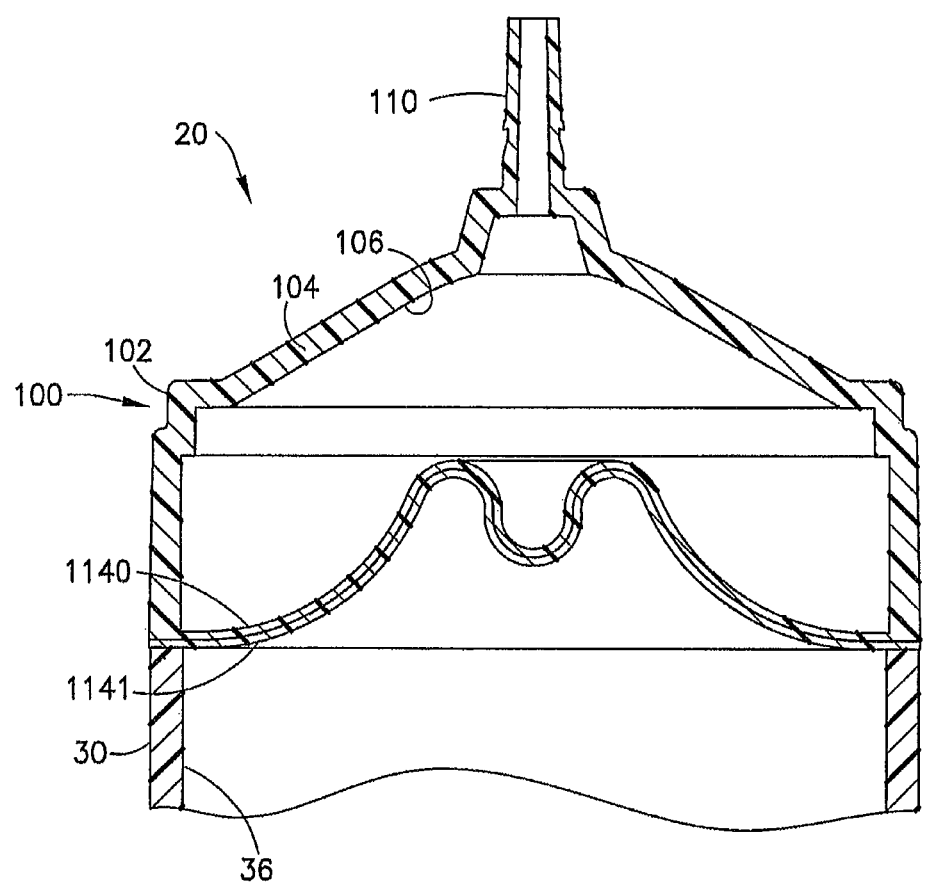
FIG. 68 is a schematic cross-sectional view of another embodiment of the bladder syringe in which the bladder may comprise a second safety liner.
Figures 69A, 69B:
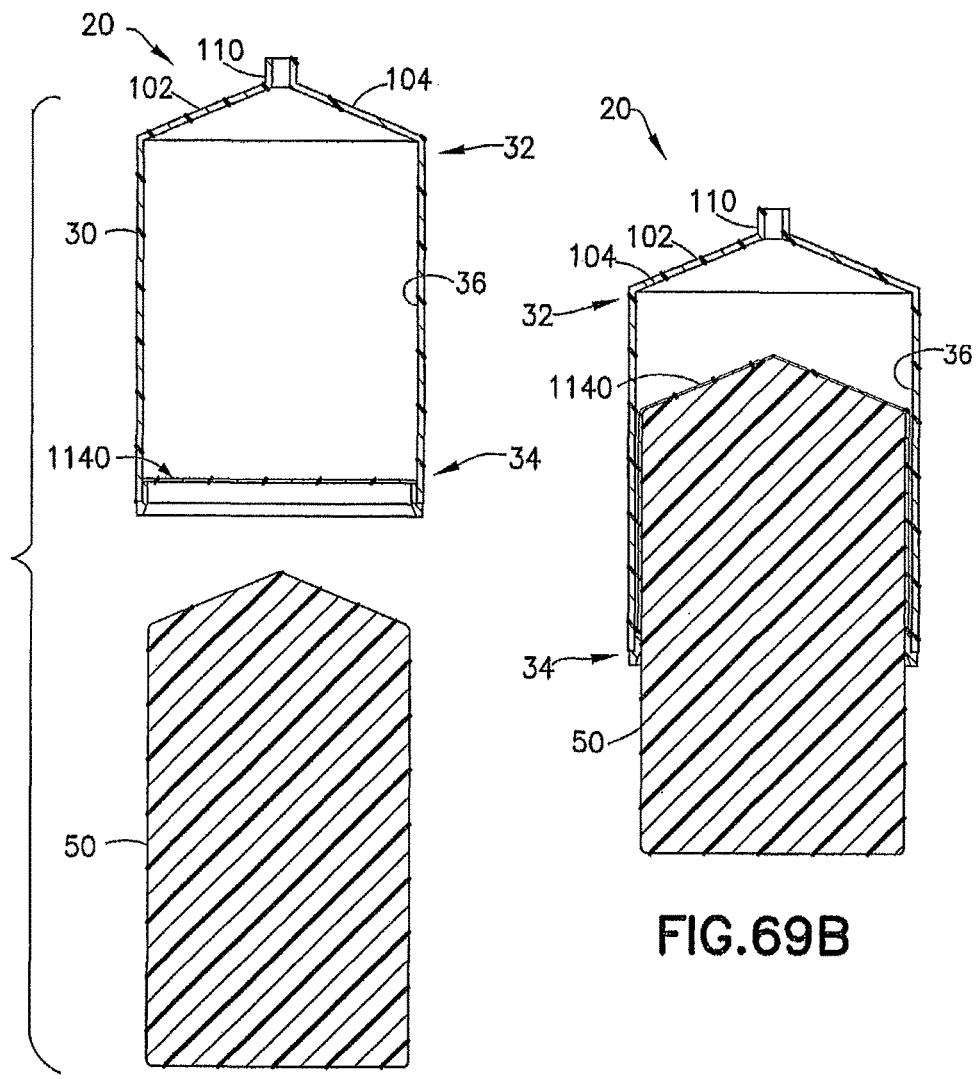
FIGS. 69A-69B are respective schematic cross-sectional views of another embodiment of the bladder syringe in which the bladder covers a rear or proximal end of the cylindrical body of the bladder syringe.

In the numerous embodiments of the bladder 1140 described previously, the bladder 1140 is typically shown as a singular membrane. However, as shown in FIG. 68, the bladder 1140 may comprise a second safety liner 1141 either molded with the bladder 1140 or otherwise incorporated into the cap-bladder assembly 100 as a safety liner in case of failure of the bladder 1140. The safety liner 1141 may be made of latex and like materials. Moreover, in the numerous embodiments of the bladder 1140 described previously, the bladder 1140 is typically shown as part of the cap-bladder assembly 100. However, as shown in FIGS. 69A-69B, the bladder 1140 may also be provided at other locations in the cylindrical body 30, such as covering the proximal end 34 of the cylindrical body 30. The plunger element 50 is operable as a conventional displacement plunger like those used in conventional syringes and air in the cylindrical body 30 distal or forward of the bladder 1140 is exhausted therefrom via the discharge conduit 110 by forward or distal movement of the plunger element 50. Reverse movement of the plunger element 50 draws fluid into the syringe-type cylindrical body 30 in this embodiment. The cap body 104 is integral with the cylindrical body 30 in this embodiment.

Figure 70A:
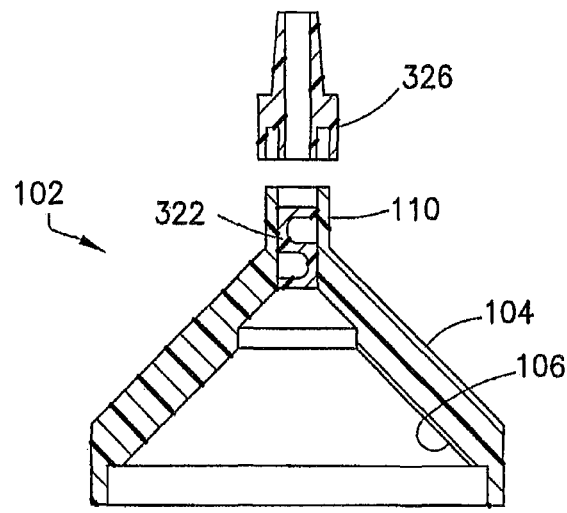
FIGS. 70A-70B are respective schematic cross-sectional views of two (2) embodiments of the cap-bladder assembly having different high-crack pressure bi-directional check valves disposed to control fluid into and from a discharge conduit in the cap of the cap-bladder assembly.
Figure 70B:
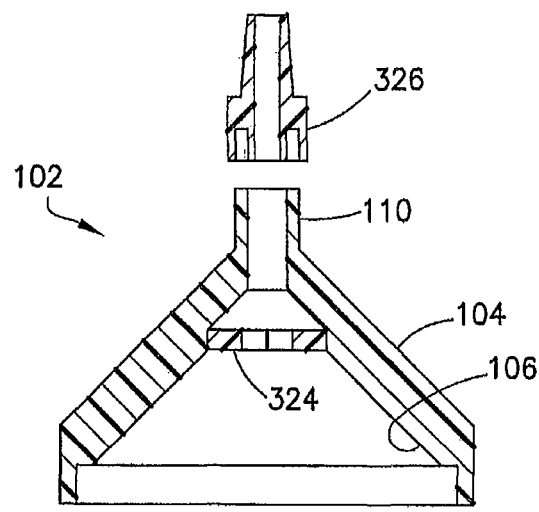

Referring to FIGS. 70A-70B, an embodiment of the cap 102 of the cap-bladder assembly 100 is shown having two (2) different embodiments of high-crack pressure bi-directional check valves 322, 324 disposed to control fluid into and from the discharge conduit 110 and which provide resistance to facilitate purging of air from behind the bladder 1140 as the plunger element 50 moves forward without requiring a separate plug or blocking of the discharge conduit 110. The check valves 322, 324 enable air to be purged from the cap body 104 and reduce or eliminate the possibility of pulling unwanted fluid (e.g., blood) into the cap body 104 and, further, reduce the possibility of unintended discharge of fluid (e.g., a gravity flow condition, etc.) from the cap body 104. In FIG. 70A, the check valve 322 is a collapsible column that collapses at predetermined or preset pressure to allow fluid to pass, and in FIG. 70B the check valve 324 is conventional slit-type check valve. A removable dust cap 326 is also shown in these figures which is suitable for use in any of the embodiments of the cap 102 in this disclosure.

Referring next to FIGS. 71A-71C, another bladder syringe 20 is shown that incorporates an alternative method for securing the cap-bladder assembly 100 to the cylindrical body 30. In this embodiment, the distal end 32 of the cylindrical body 30 comprises an enlarged end flange 400 with a snap closure element 402 that extends upward or distally from the end flange 400. The snap closure element 402 has a barbed end 403. Additionally, the end flange 400 has a distal rim 404 with inner and outer circumferential walls 406, 408 that define an annular recess 410 therebetween. The inner circumferential wall 406 is slightly shorter in height than the outer circumferential wall 408. A cap or cover 412 is connected by a hinge 414 to the end flange 400 on the opposite side from the snap closure element 402. The cap or cover 412 has an overall shape to accept the cap-bladder assembly 100 therein. The cap or cover 412 comprises an interior cavity 416 to receive the cap-bladder assembly 100 and has a tubular end portion 418 that receives the discharge conduit 110 on the cap body 104 of the cap 102. The cap or cover 412 further comprises a proximal rim 420 that is sized to fit over the distal rim 404 on the end flange 400 and, in particular, over and around the outer circumferential wall 408 of the distal rim 404. The proximal rim 420 comprises an attachment tab 422 for engagement by the snap closure element 402 to secure the cap or cover 412 to the end flange 400 during use of the bladder syringe 20 in this embodiment.

In this embodiment, the cap-bladder assembly 100 is modified to operate with the hinged cover 412 and distal rim 404 on the end flange 400. The cap-bladder assembly 100 comprises a cap 102 wherein the cap body 104 and bladder 1140 are, desirably, co-injection molded together, in a similar manner to the embodiment shown and as described previously in connection with FIG. 47A wherein the bladder 1140 was described as being co-injection molded with the inner liner 194. The retainer ring 140 may be eliminated in this embodiment. Further, the cap body 104 is formed without the cylindrical portion 114 described previously. Accordingly, as shown in detail in FIG. 71C, an exterior circumferential rim 424 of the cap body 104 is molded to an exterior circumferential rim 1264 of the bladder 1140. Alternatively, the circumferential rims 424, 1264 may be secured by other means such as ultrasonic welding, adhesive, and like joining methods. The exterior rim 1264 on the bladder 1140 comprises a depending rib 1266 adapted to be received in the annular recess 410 between the inner and outer circumferential walls 406, 408 of the distal rim 404. The engagement of the barbed end 403 on the snap closure element 402 with the attachment tab 422 on the proximal rim 420 of the cover 412 further secures the depending rib 1266 in the annular recess 410 in a fluid-tight connection to enable a vacuum to be drawn in the cylindrical body 30 by the plunger element 50, which is not shown in FIGS. 71A-71C and details of various embodiments the plunger element 50 may be found in the foregoing.

To attach the cap-bladder assembly 100 to the cylindrical body 30 in this embodiment, an attendant medical practitioner typically removes the cap-bladder assembly 100 from its packaging and places the cap-bladder assembly 100 in association with the end flange 400 on the cylindrical body 30 so that the depending rib 1266 on the circumferential rim 1264 of the bladder 1140 is received in the annular recess 410 between the inner and outer circumferential walls 406, 408 of the distal rim 404 on the end flange 400. Next, the user pivots the hinged cover 412 so that the proximal rim 420 fits over the distal rim 404 on the end flange 400 and, in particular, over and around the outer circumferential wall 408 of the distal rim 404. As the hinged cover 412 is pivoted toward the end flange 400, the proximal rim 420 engages the barbed end 403 on the snap closure element 402 and displaces the snap closure element 402 radially outward to enable the proximal rim 420 to seat around the outer circumferential wall 408 of the distal rim 404. The attachment tab 422 on the proximal rim 420 is generally aligned with the barbed end 403 so that as the proximal rim 420 fits over the distal rim 404 on the end flange 400 the barbed end 403 snaps into engagement onto the attachment tab 422 and secures the hinged cover 412 to the end flange 400 and provides a generally or substantially fluid-tight seal between the depending rib 428 in the annular recess 410.

Figure 72A:
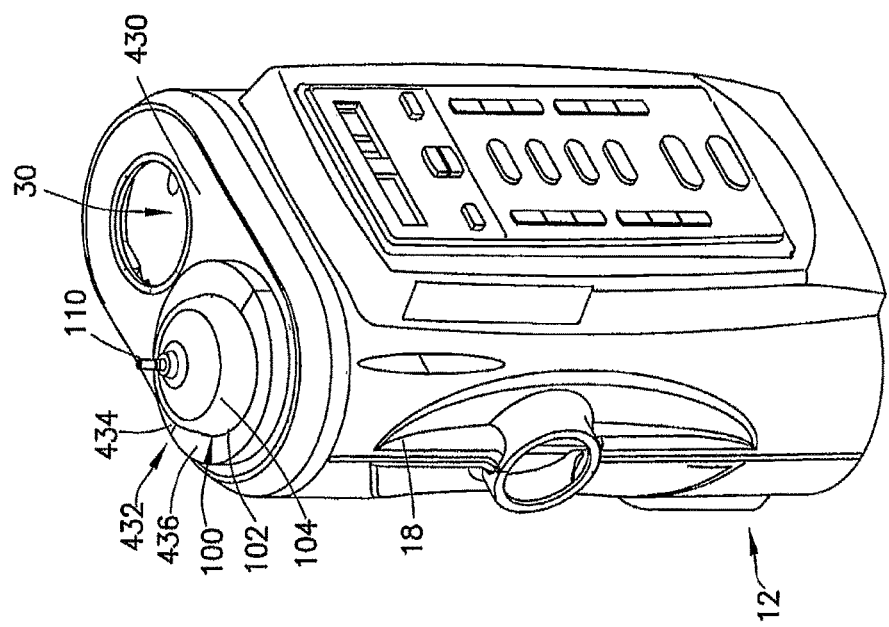
FIGS. 72A-72B are two perspective views of a fluid injector for operating the bladder syringe and show another arrangement for securing the cap-bladder assembly to the cylindrical body of the bladder syringe.
Figure 72B:
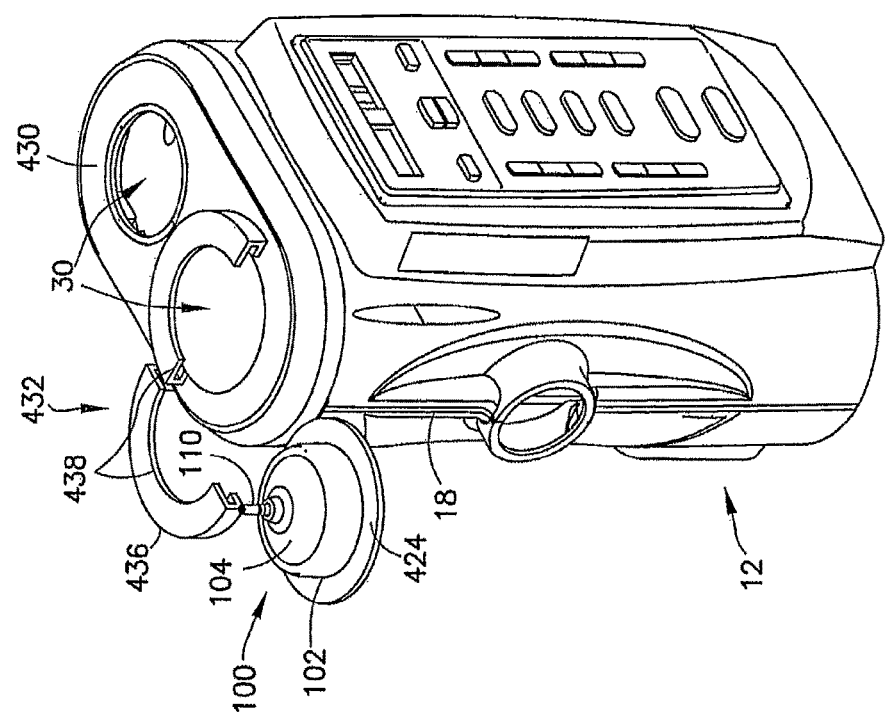

Referring next to FIGS. 72A-72B, another embodiment of the bladder syringe 20 is shown that incorporates the cylindrical body 30 into the interior of the housing 18 of the fluid injector 12 and the cap-bladder assembly 100 is secured directly to the fluid injector housing 18. In FIGS. 72A-72B, the cylindrical body 30 is disposed in the interior of the fluid injector housing 18. A distal end 430 of the fluid injector housing 18 supports a clamping assembly 432 comprising a fixed arm 434 and a pivotal swing arm 436 each defining an arcuate recess 438 therein. The clamping assembly 432 may be automatically operable by the controller associated with the fluid injector 12. As in the embodiment of the cap-bladder assembly 100 discussed above in connection with FIGS. 71A-71C, the cap body 104 in this embodiment is formed without the cylindrical portion 114 described previously. In present embodiment, the exterior circumferential rim 424 of the cap body 104 is molded or otherwise attached to the exterior circumferential rim 1264 (not shown in FIGS. 72A-72B) of the bladder 1140. Additionally, in the present embodiment, the exterior circumferential rim 424 of the cap body 104 is enlarged radially as compared to the embodiment shown in FIGS. 71A-71C to fit within the mating arcuate recesses 438 in the fixed arm and swing arm 434, 436 of the clamping assembly 432. Details of the connection between the cap-bladder assembly 100 and cylindrical body 30 are omitted in FIGS. 72A-72B but may be similar to that described in the foregoing in connection with FIGS. 71A-71C. As illustrated, a user simply mates the cap-bladder assembly 100 to the cylindrical body 30 disposed in the fluid injector housing 18 while further placing the exterior circumferential rim 424 on the cap body 104 into the arcuate recess 438 in the fixed arm 434 and then pivots the swing arm 436 so that the arcuate recess 438 therein likewise engages the exterior circumferential rim 424 on the cap body 104. A lock or other securing connection (not shown) is provided between the fixed arm 434 and swing arm 436 to secure the circumferential rim 424 in the mating arcuate recesses 438 in the fixed arm 434 and swing arm 436.

Referring to FIGS. 73A-73E, another bladder syringe 20 is shown that incorporates another alternative method for securing the cap-bladder assembly 100 to the cylindrical body 30. In this embodiment, the distal end 32 of the cylindrical body 30 comprises an enlarged end flange or rim 440 with inner and outer circumferential walls 446, 448 that define an annular recess 450 therebetween. The inner circumferential wall 446 is slightly larger in height and tapered as compared to the outer circumferential wall 448. Additionally, two (2) axially spaced radial flanges 452, 454 are provided on the cylindrical body 30 axially below the end flange or rim 440. A pair of axial walls 456 extends between the radial flanges 452, 454 which act as rotation stops as described herein. The proximal end 34 of the cylindrical body 30 is formed with a circumferential flange 38 positioned to engage the front end of the housing 18 of the fluid injector 12 to properly seat the cylindrical body 30 relative to the fluid injector 12 as in previous embodiments, and a suitable connecting arrangement for mounting the proximal end 34 of the cylindrical body 30 to a power fluid injector may be found in U.S. Pat. No. 7,450,856 to Hitchins et al., incorporated herein by reference. In FIGS. 73A-73E, a flex-leg connecting assembly 480 is used to secure the cap-bladder assembly 100 to the distal end 32 of the cylindrical body 30.

Figure 73A:
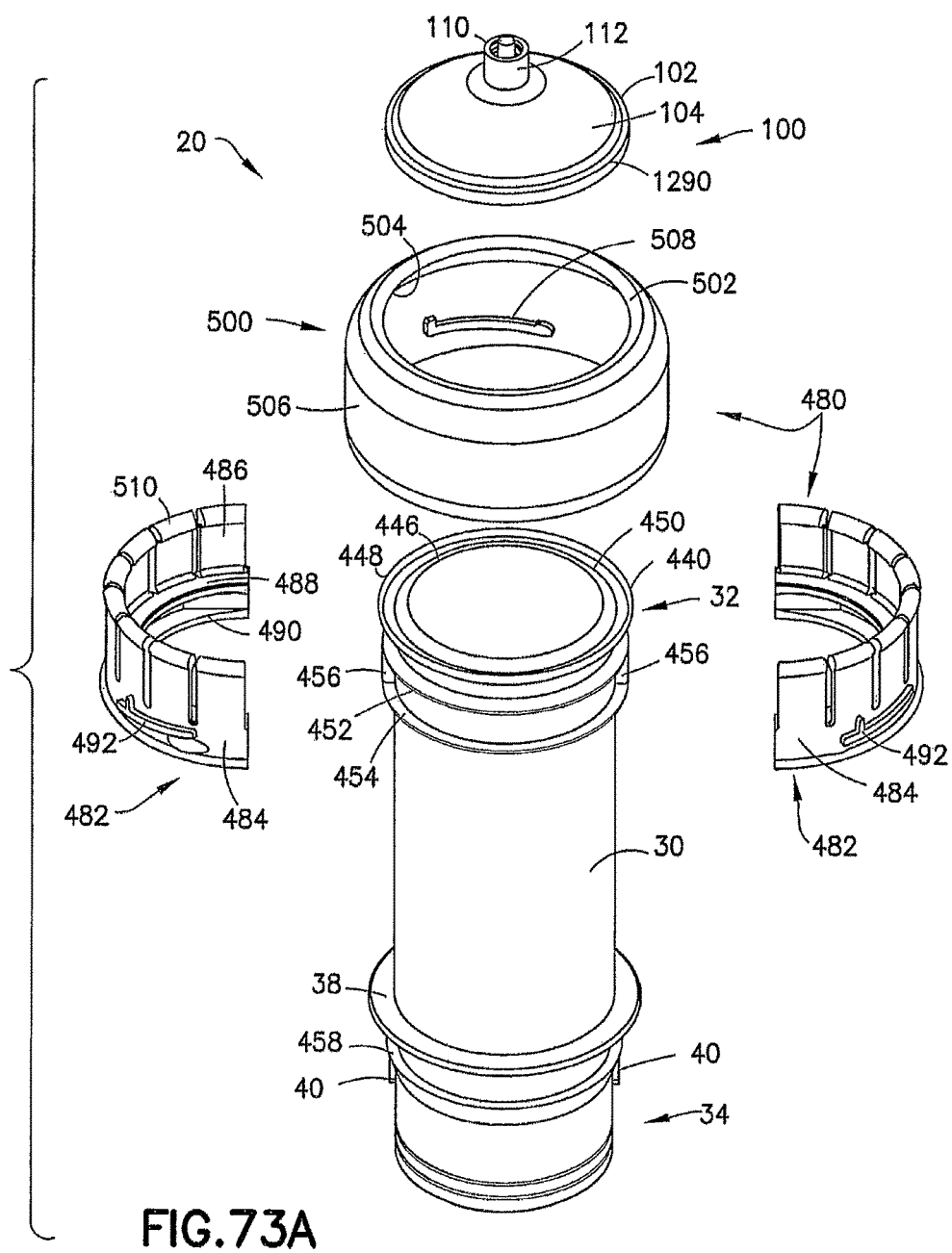
FIG. 73A is an exploded view of another embodiment of the bladder syringe incorporating another arrangement for securing the cap-bladder assembly to the cylindrical body of the bladder syringe.
Figure 73B:
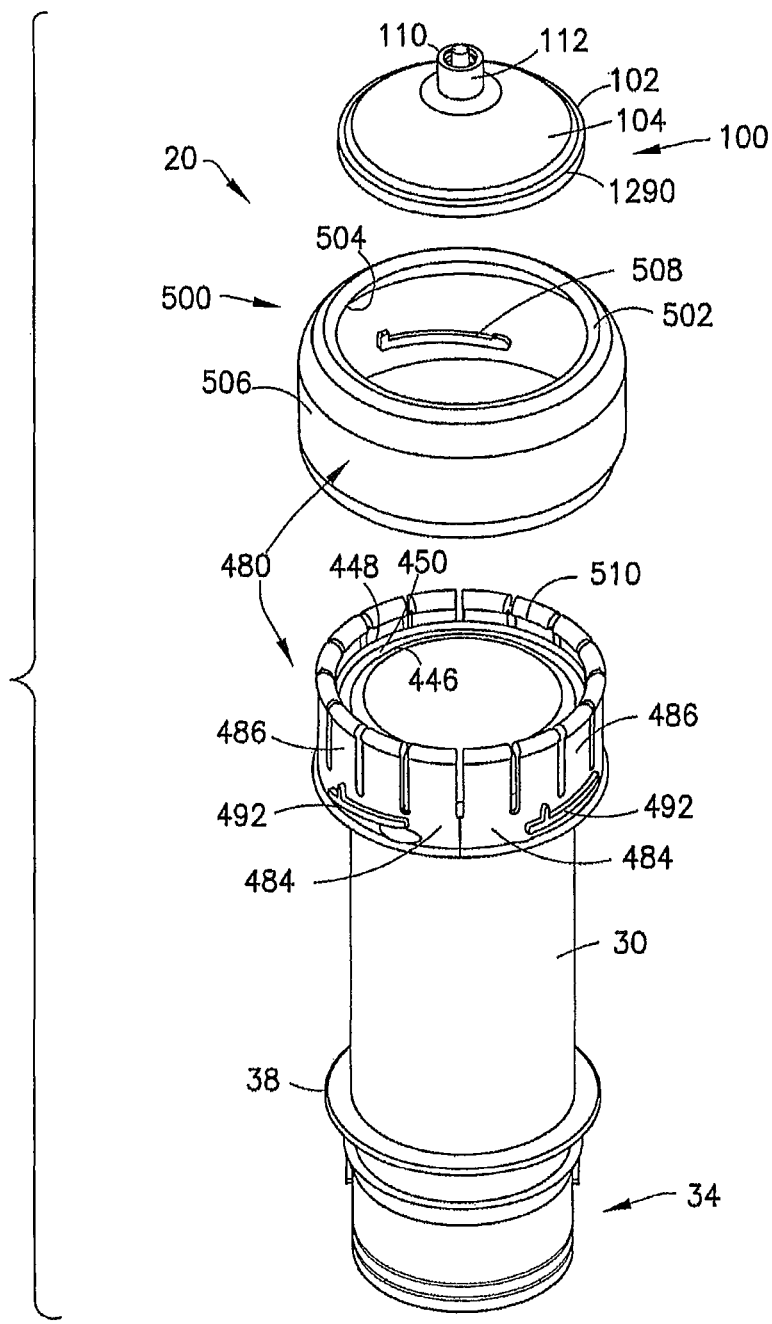
FIGS. 73B-73C are exploded views showing progressive states of assembly for the bladder syringe of FIG. 73A.
Figure 73C:
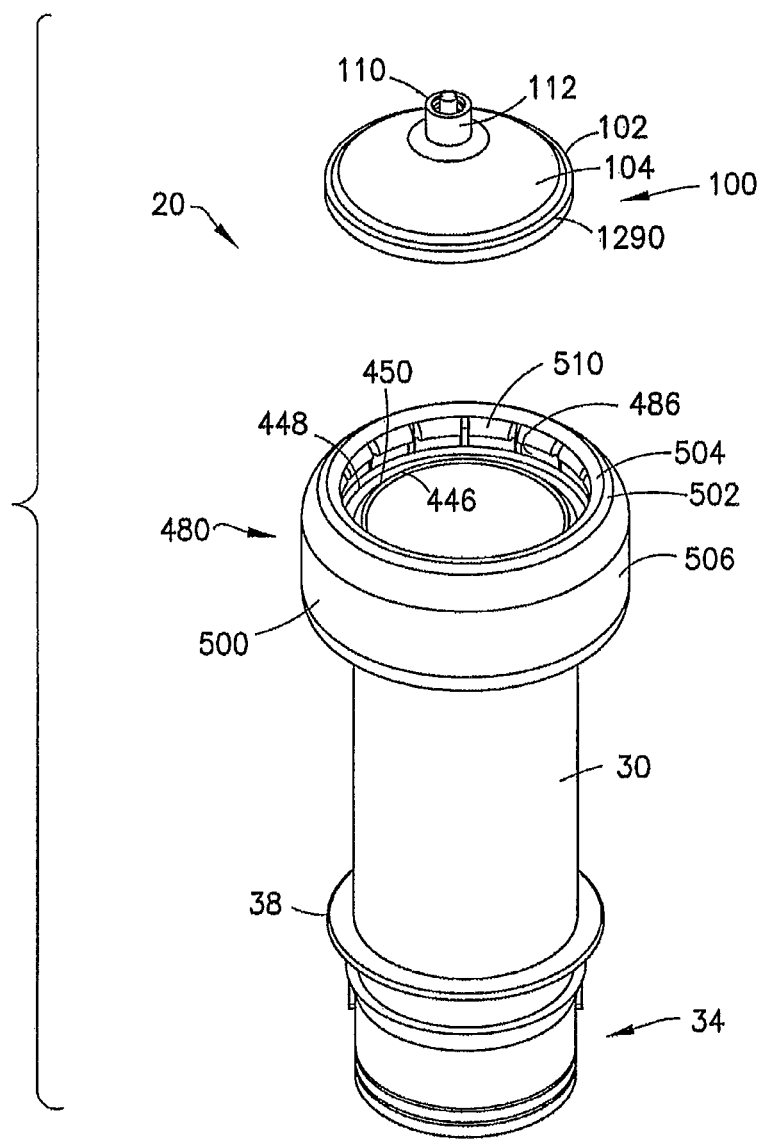
Figure 73D:
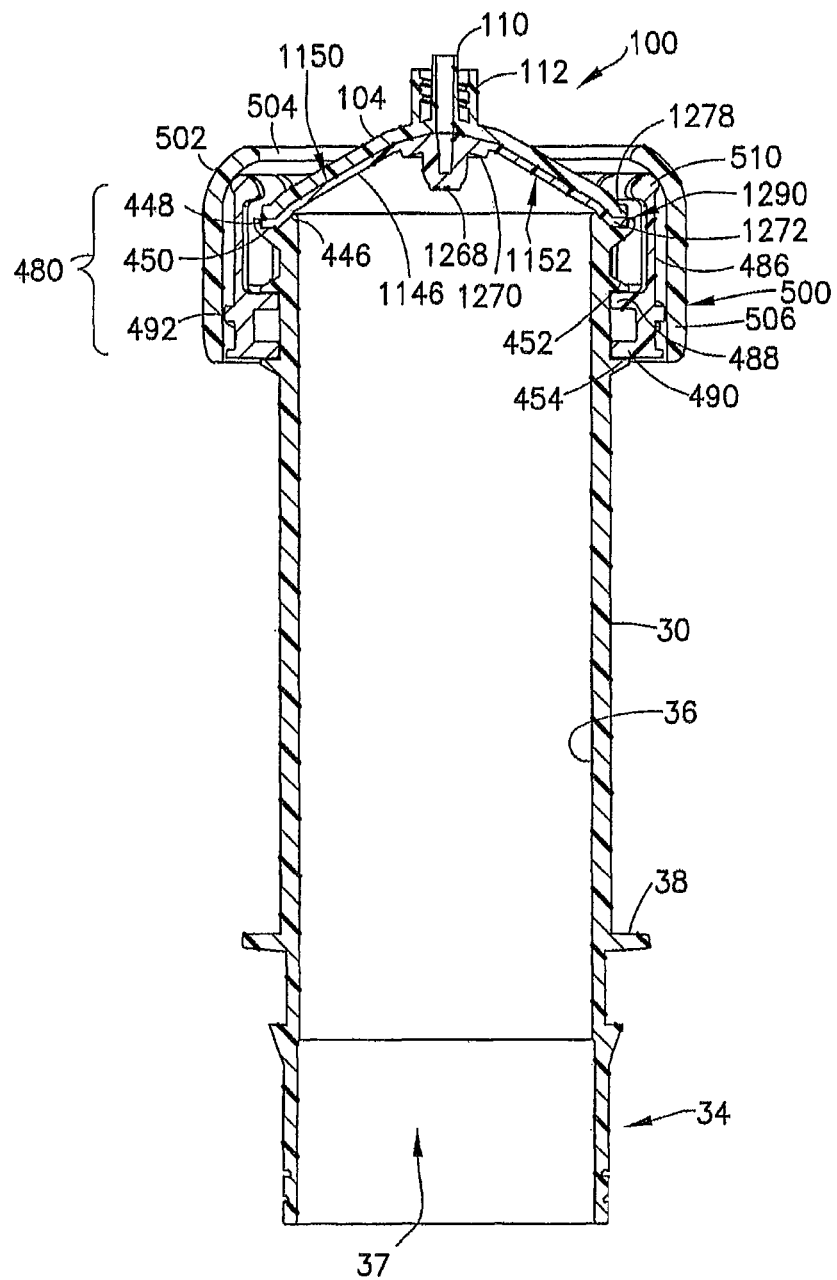
FIGS. 73D-73E are cross-sectional views of the embodiment of the bladder syringe of FIGS. 73A-73C showing, respectively, unlocked and locked states for the cap-bladder assembly on the cylindrical body of the bladder syringe.
Figure 73E:
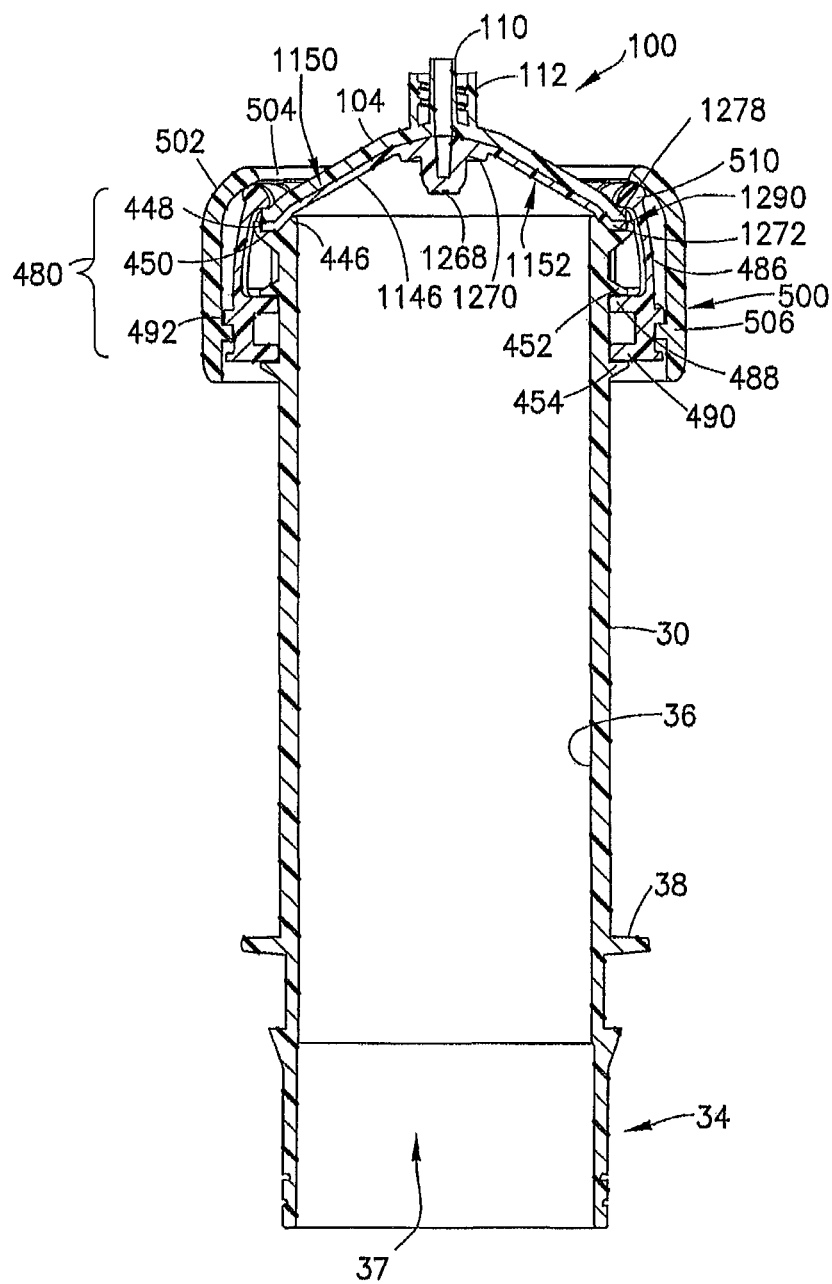

In the present embodiment, the cap-bladder assembly 100 is modified to operate with the flex-leg connecting assembly 480. The cap-bladder assembly 100 comprises a cap 102 wherein the cap body 104 and bladder 1140 are, desirably, co-injection molded together, and the retainer ring 140 may again be eliminated in this embodiment. Further, the cap body 104 is formed without the cylindrical portion 114 described previously. The cap-bladder assembly 100 is substantially similar to the embodiment shown in FIG. 47C discussed previously. In that embodiment, the cap 102 has a cap body 104 with a co-injection molded bladder 1140, with the membrane portion 1146 having central well portion 1268. In the embodiment of FIGS. 73D-73E, the central well portion 1268 is surrounded by a thickened circumferentially region 1270. As shown in FIGS. 73D-73E, the distal side 1150 of the membrane portion 1146 generally conforms to the internal shape of the interior cavity 106 of the cap body 104 and the opposing proximal side 1152, including the central well portion 1268 and surrounding thickened region 1270, defines a profile or shape that matches the profile of the plunger element 50 (see FIG. 47C), which is omitted in FIGS. 73D-73E. Additionally, in FIGS. 73D-73E, the bladder 1140 and the cap body 104 have outer circumferential rims or flanges 1272, 1278, respectively, that are joined together in the co-injection molding process, but these outer circumferential rims or flanges 1272, 1278 lack the mutually engaging ribs 1274, 1280 and 1276, 1282 described previously in connection with FIG. 47C. However, these features may be provided if so desired. As an alternative, the outer circumferential rims or flanges 1272, 1278 may be joined by other joining methods such as ultrasonic welding, laser welding, adhesive joining, and like joining techniques. Accordingly, as shown in FIGS. 73D-73E, an exterior circumferential rim 1278 of the cap body 104 is joined to an exterior circumferential rim 1272 of the bladder 1140 and a composite end flange or rim 1290 defined by this molded joint is adapted to be received in the annular recess 450 defined between the inner and outer circumferential walls 446, 448 of the enlarged end flange or rim 440 on the distal end 32 of the cylindrical body 30.

With continued reference to FIGS. 73A-73E, the flex-leg connecting assembly 480 is comprised by a composite flex legs inner sleeve 482 disposed within a rotating outer sleeve 500. The composite flex legs inner sleeve 482 is a split-ring component formed by two (2) opposing split-ring halves 484 which each have a plurality of distally-extending contact flex legs 486. The interior of each of the split-ring halves 484 has a pair of radially-inward extending flanges 488, 490 adapted to be received and sandwiched between the two (2) radially-outward extending flanges 452, 454 on the cylindrical body 30. The exterior of each of the split-ring halves 484 comprises a series of external threads 492. The opposing free ends of the split-ring halves 484 may be adapted for frictional interengagement, if desired, to secure the two (2) split-ring halves 484 together, or a locking connection (not shown) may be provided to secure the free ends. Desirably, the pair of axial walls 456 that extends between the radial flanges 452, 454 on the cylindrical body 30 engage a recess or groove (not shown) in the interior of the opposing split-ring half 484 and this engagement acts as rotation stops so as to prevent rotation of the composite flex legs inner sleeve 482 once assembled by joining the two (2) split-ring halves 484 together around the cylindrical body 30.

The outer sleeve 500 comprises a curved distal end or portion 502 that defines an opening 504 sized to receive the cap-bladder assembly 100 therethrough, and is adapted to fit over the composite flex legs inner sleeve 482. The outer sleeve 500 has a sidewall 506 extending from the distal end or portion 502 that is of a sufficient axial length to entirely enclose the composite flex legs inner sleeve 482. The interior side of the sidewall 506 comprises mating threads 508 to engage the exterior threads 492 on the exterior of each of the split-ring halves 484. The outer sleeve 500 is connected to the composite flex legs inner sleeve 482 by threaded engagement between the mating threads 492, 508. When the outer sleeve 500 is rotated relative to the inner sleeve 482, the outer sleeve 500 is either drawn axially downward along the inner sleeve 482 or moves axially upward along the inner sleeve 482. In an open position of the flex-leg connecting assembly 480, as shown in FIG. 73D, the outer sleeve 500 is in a position relative to the inner sleeve 482 to radially position the contact flex legs 486 at a radial position that allows the cap-bladder assembly 100 to be inserted through the distal opening 504 and be connected to the cylindrical body 30. In this connection or engagement, the composite end flange or rim 1290 defined by the exterior circumferential rim 1278 of the cap body 104 and the exterior circumferential rim 1272 of the bladder 1140 is received in the annular recess 450 defined between the inner and outer circumferential walls 446, 448 of the enlarged end flange or rim 440 on the distal end 32 of the cylindrical body 30. To secure this engagement, the outer sleeve is rotated, for example clockwise, relative to the inner sleeve 482 to arrive at the closed position, shown in FIG. 73E, wherein the flex legs 486 are displaced radially inward to engage the composite end flange or rim 1290 which secures the cap-bladder assembly 100 in place. As shown in FIG. 73E, the clockwise rotational movement of the outer sleeve 500 causes the mating threads 492, 508 to draw the outer sleeve 500 axially downward along the inner sleeve 482, and this motion causes the internally curved distal end or portion 502 of the outer sleeve 500 to contact an externally curved distal end 510 on each of the flex legs 486 and deflects the flex legs 486 radially inward to engage the composite end flange or rim 1290 on the cap-bladder assembly 100. Reverse rotational movement of the outer sleeve 500 causes reverse movement and releases the flex legs 486 from the locking position shown in FIG. 73E as the outer sleeve 500 moves axially upward along the inner sleeve 482. Once the flex legs 486 disengage from the composite end flange or rim 1290 on the cap-bladder assembly 100, the cap-bladder assembly 100 may be removed for disposal. The flex legs 486 are resiliently flexible to move to the position shown in FIG. 73D when not acted upon by the internally curved distal end 502 of the outer sleeve 500. The flex-leg connecting assembly 480 has numerous advantages. For example, the loading of the cap-bladder assembly 100 is non-orientation specific and does not require rotation during assembly so that the bladder 1140 is not subject to torque or twisting motion. Additionally, all components of the flex-leg connecting assembly 480 may be permanently connected to the cylindrical body 30 during manufacturing and there will be no loose parts for the end user to assemble.

Figure 74A:
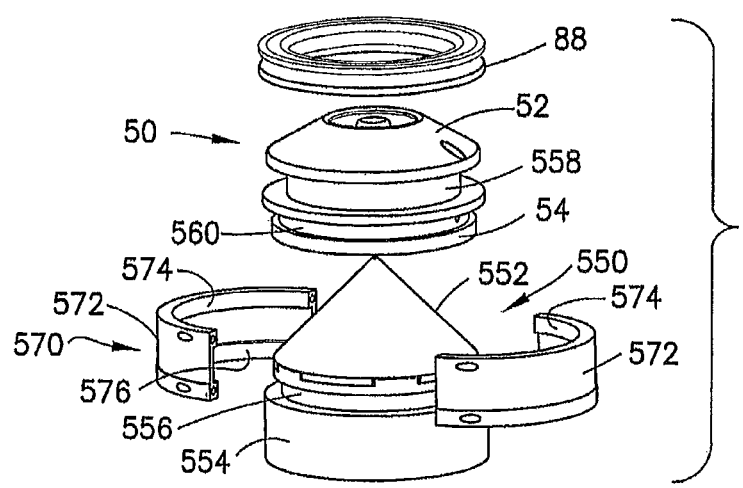
FIG. 74A is an exploded perspective view of an adapter assembly for connecting the plunger element of the bladder syringe to a conventional or known plunger.
Figure 74B:
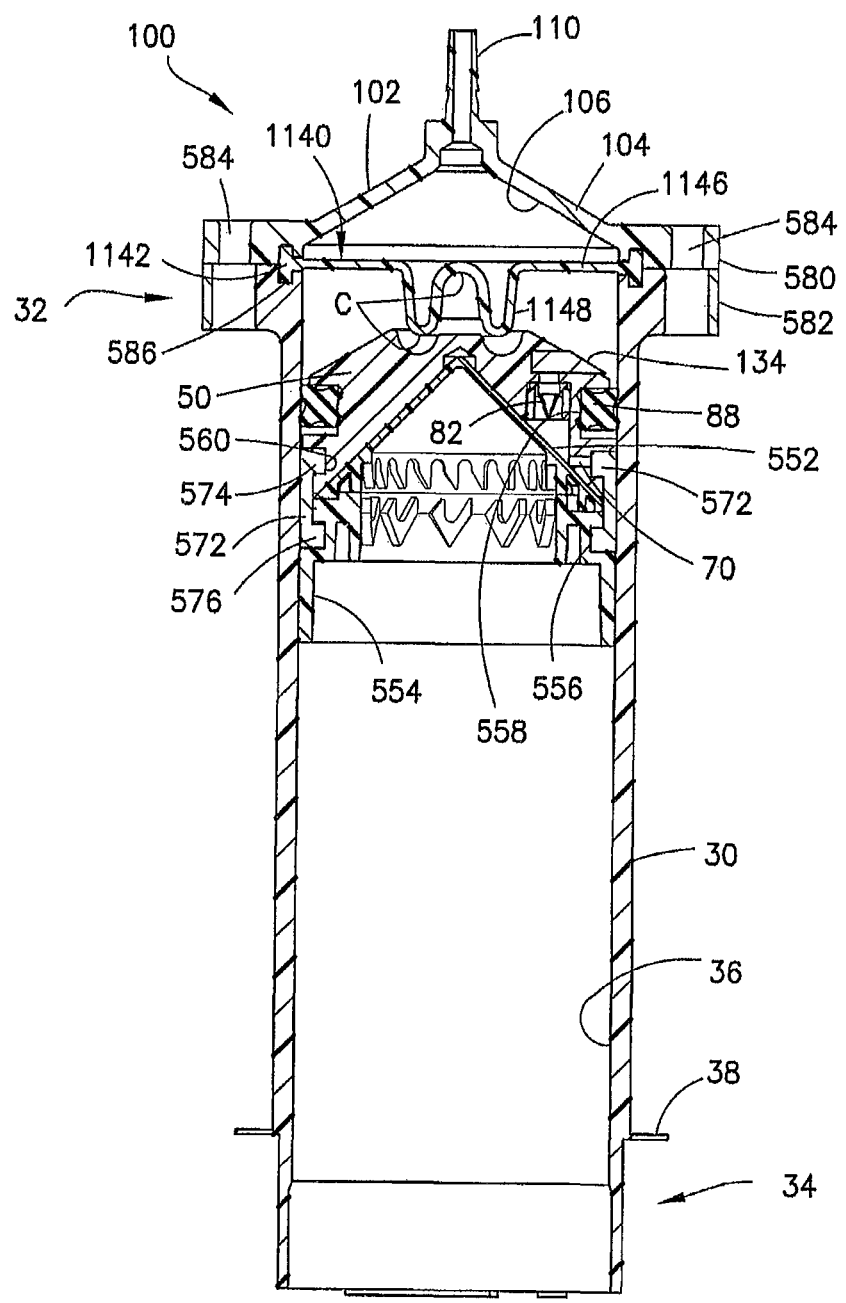
FIG. 74B is a schematic cross-sectional view of an embodiment of the bladder syringe incorporating the adapter assembly of FIG. 74A.

Referring next to FIGS. 74A-74B, an adapter assembly 570 is shown for connecting the plunger element 50, such as the embodiment shown in FIG. 10A, to a conventional or known plunger 550 adapted for connection to a piston element of a power fluid injector, such as the piston element 14 of the fluid injector 12 discussed previously. The depicted embodiment of the plunger 550 may be a plunger manufactured by Imaxeon and provided in a 200 ml syringe used in a power fluid injector sold under the trademark Salient® and shown in International Publication No. WO 2009/036496, incorporated herein by reference. The plunger 550 comprises a conical distal end or portion 552, cylindrical proximal end or portion 554, and an intervening annular recess or groove 556 between the portions 552, 554. The plunger element 50 in this embodiment has a unitary body component with a conical distal portion 52 and a cylindrical proximal portion 54, and a seal ring 88 is disposed in an annular recess or groove 558 defined in the proximal portion 54. However, a two-piece plunger element 50 split at annular recess or groove 558 may also be used in this embodiment. In the embodiment of the plunger element 50 depicted in FIG. 10A, the conical distal portion 52 and the cylindrical proximal portion 54 are separate components that are joined together. In the embodiment of the plunger element 50 shown in FIGS. 74A-74B, the distal portion 52 defines an annular recess or groove 560 proximal of the annular recess or groove 558 that supports the seal ring 88.

The adapter assembly 570 is comprised of two (2) split-ring elements or halves 572 which each have a pair of radially-inward extending flanges 574, 576 adapted to be received, respectively, in the annular recess or groove 560 in the proximal portion 54 of the plunger element 50 and the annular recess or groove 556 in the plunger 550, thereby connecting the plunger element 50 with the plunger 550. The opposing free ends of the split-ring halves 572 may be adapted for frictional interengagement to secure the two (2) split-ring halves 572 together, or a locking connection or mechanism (not shown) may be provided to secure the free ends together. As shown in FIG. 74B, the interior wall 36 of the cylindrical body 30 radially supports the two (2) split-ring halves 572 in an assembled configuration. As this figure shows, the adapter assembly 570 may be used to convert a conventional or known plunger 550 for use as part of the bladder syringe 20. In the bladder syringe 20 of FIG. 74B, the cap-bladder assembly 100 is modified as is the distal end 32 of the cylindrical body 30. The cap body 104 of the cap 102 comprises an enlarged circumferential rim 580 that cooperates with a corresponding circumferential rim 582 on the distal end 32 of the cylindrical body 30. A plurality of apertures 584 may be formed by the connection of the circumferential rims 580, 582 that accept connecting mechanical fasteners and like connecting elements (not shown) to secure these components together. The bladder 1140 of the cap-bladder assembly 100 in this embodiment is generally similar to that discussed previously in connection with FIGS. 12A-12B. The air-venting and vacuum-generating features of the plunger element 50 are generally similar to those shown and discussed in connection with FIG. 10A. The connection of the cap body 104 onto the cylindrical body 30 in this embodiment may be similar to that shown in FIGS. 73A-73E discussed previously.

Figure 75:
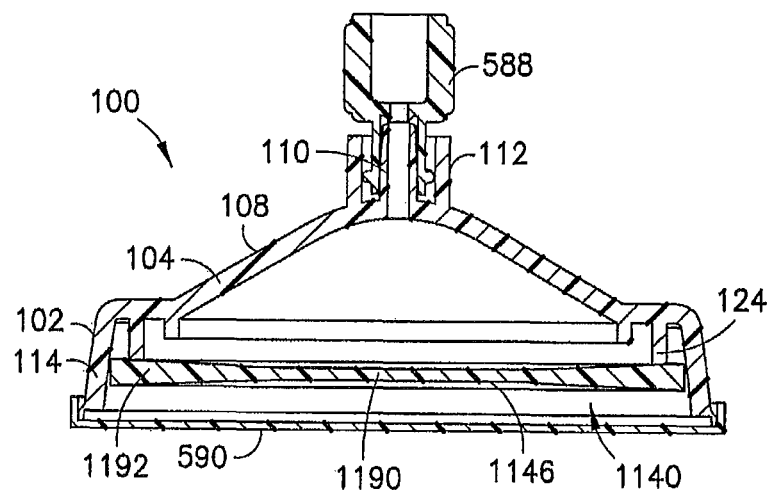
FIG. 75 is a cross-sectional view of the cap-bladder assembly prepackaged with two removable shipping caps.

Referring now to FIGS. 75-81, as noted previously, it is desirable to provide a sterile packaging arrangement for the cap-bladder assembly 100 used in the bladder syringe 20. In FIG. 75, the cap-bladder assembly 100 may be prepackaged with two removable shipping caps 588, 590 for covering, respectively, the end connector 112 on the discharge conduit 110 of the cap body 104 and the second covering the opposing open end of the cap body 104. The depicted and non-limiting embodiment of the bladder 1140 is similar to the embodiment shown in FIGS. 24A-24B in which the membrane portion 1146 is shaped like a flat trampoline with a thinner section 1190 in the center and a thicker outer section 1192 tapering from the thinner center section 1190.

Figure 76:
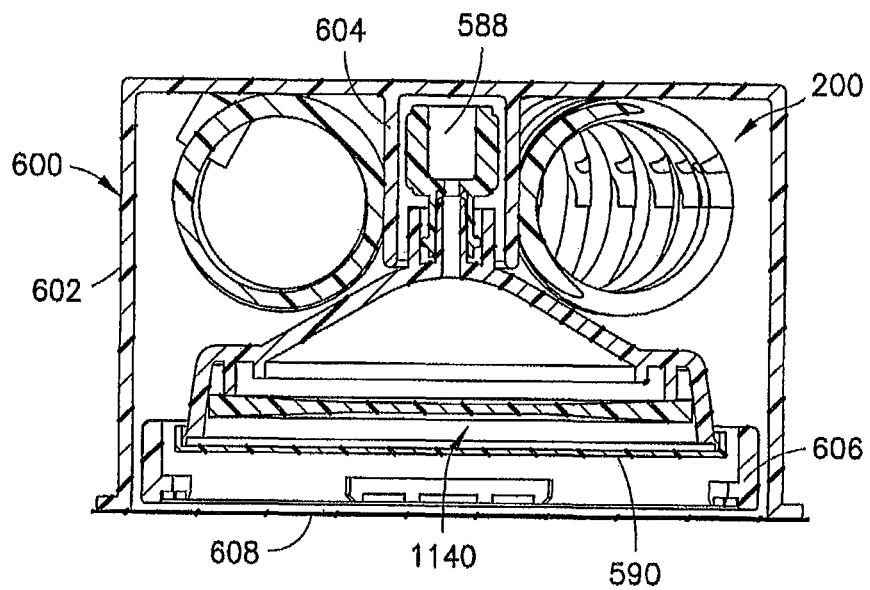
FIG. 76 is a cross-sectional view of a cup-shaped packaging container for the cap-bladder assembly of the bladder syringe.

In FIG. 76, a packaging container 600 is shown with a cup-shaped body 602 that fits over the cap-bladder assembly 100 and comprises opposing internal stabilizers 604, 606 that engage, respectively, the two removable shipping caps 588, 590. The open end of the cup-shaped body 602 comprises a protective seal 608, typically a sterilized seal, that is peeled away to remove the cap-bladder assembly 100. The fluid path set 200 may also be sealed in the packaging container 600.

Figure 77:
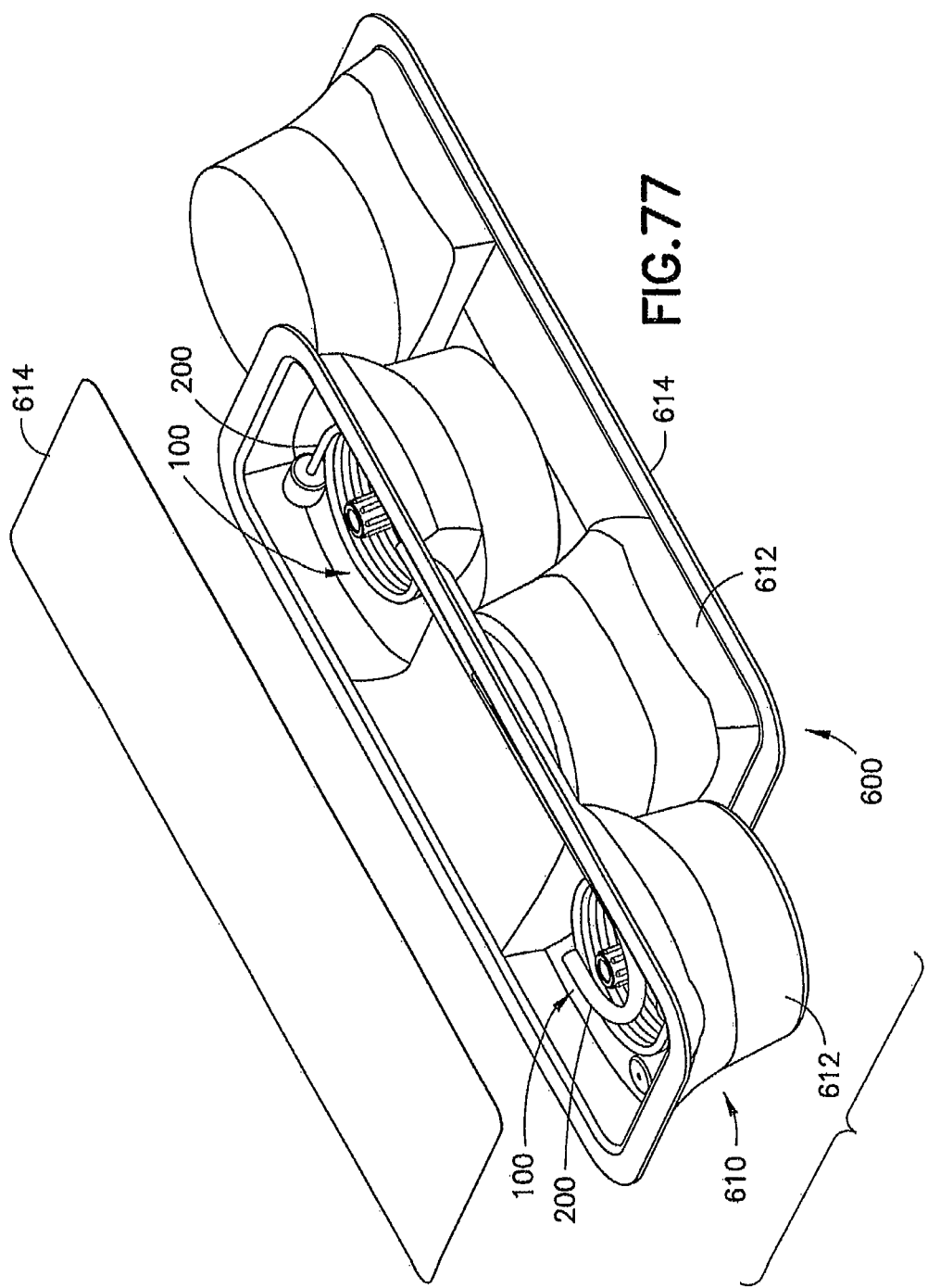
FIG. 77 is a perspective view of a packaging container with a multi-well body for the cap-bladder assembly of the bladder syringe.

In FIG. 77, a packaging container 610 is shown with a multi-well body 612 for receiving several cap-bladder assemblies 100. The multi-well body 612 enables the packaging container 610 to be nested or stacked with another packaging container 610 in an opposed or mirror-image arrangement. The open end of the multi-well body 612 comprises a protective seal 614, typically a sterilized seal, that is peeled away to remove the cap-bladder assemblies 100.

Figure 78:
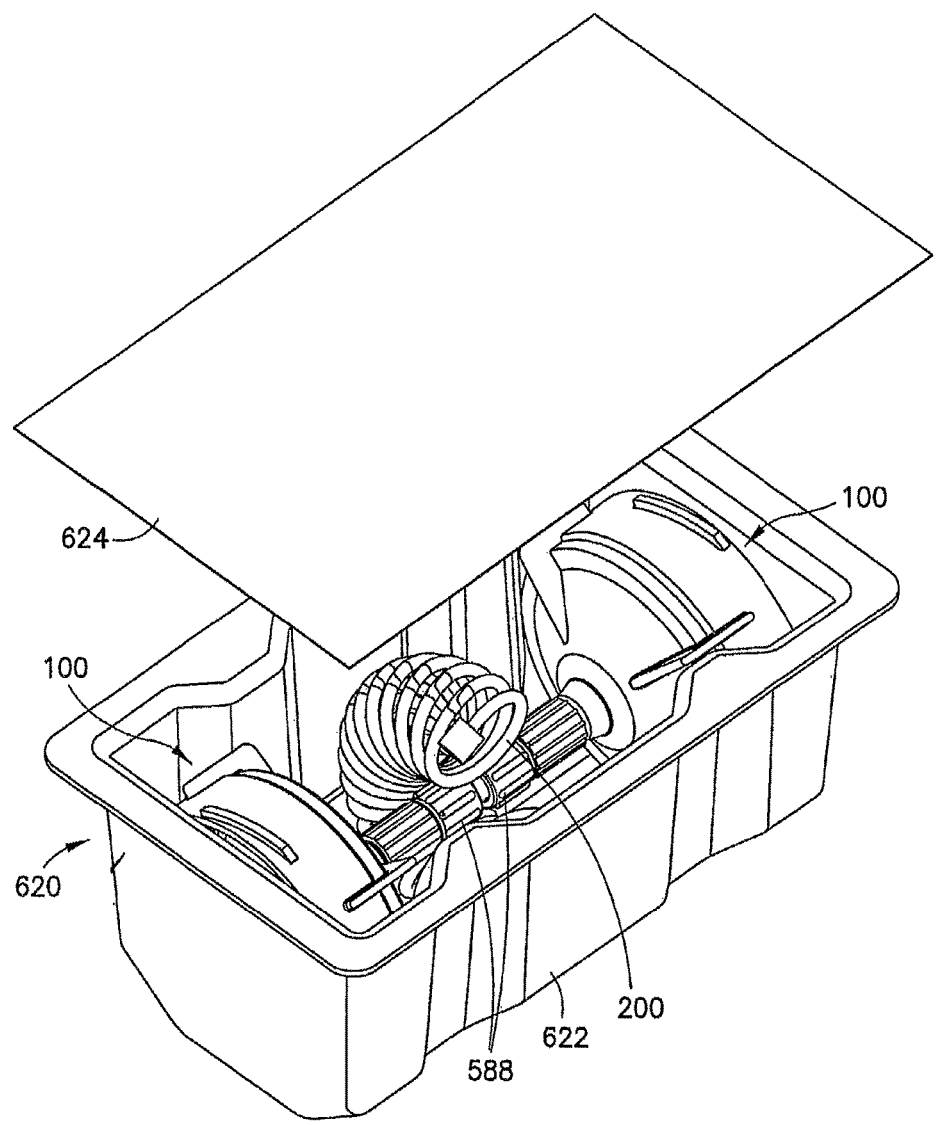
FIG. 78 is a perspective view of a packaging container with a single-well body for receiving several cap-bladder assemblies in an end-to-end relationship, wherein the discharge conduits on the respective cap-bladder assemblies.
Figure 79:
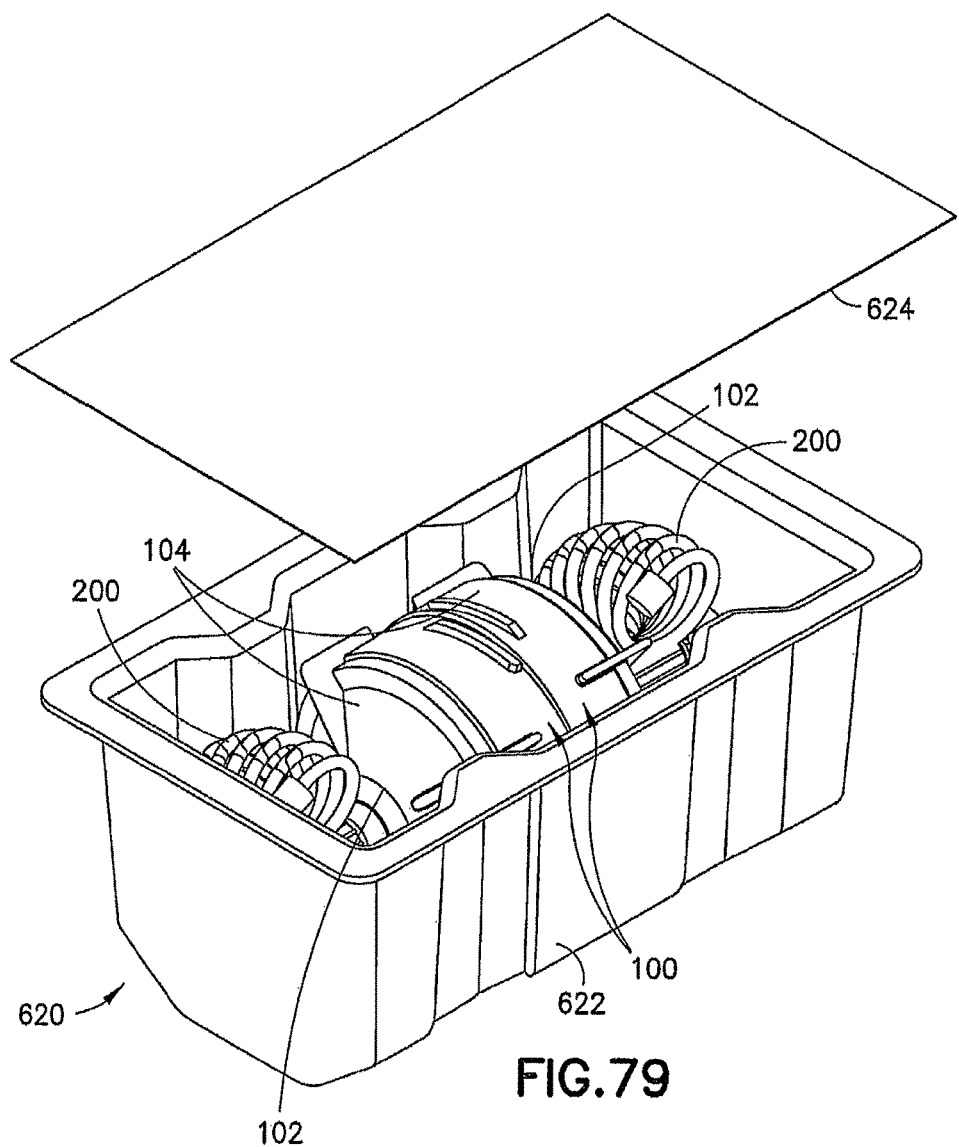
FIG. 79 is a perspective view of a packaging container with a single-well body for receiving several cap-bladder assemblies in an end-to-end relationship, wherein the open ends of the caps of the cap-bladder assemblies face one another.

In FIG. 78, a packaging container 620 is shown with a single-well body 622 for receiving several cap-bladder assemblies 100 in end-to-end relationship, wherein the discharge conduits 110 on the respective cap-bladder assemblies 100 face one another. The open end of the single-well body 622 comprises a protective seal 624, typically a sterilized seal, that is peeled away to remove the cap-bladder assemblies 100. FIG. 79 illustrates a variation of the packaging container 620, wherein the cap-bladder assemblies 100 are in end-to-end relationship, but the open ends of the cap body 104, optionally closed by shipping caps 590 discussed previously, in the respective cap-bladder assemblies 100 face one another.

In FIG. 80, the cap-bladder assemblies 100 are placed on a long bandolier protective strip 626 which serves to protect the open ends of the cap body 104. As a cap-bladder assembly 100 is required, it could just be pulled off the bandolier protective strip 626 that may further be adapted to protect the sterility of the interior of the cap body 104 for each cap-bladder assembly 100. If desired, the shipping cap 590, discussed previously, enclosing the open end of the cap body 104 in each cap-bladder assembly 100 may be affixed to the bandolier strip 626 and then remain with the strip 626 while the remainder of the cap-bladder assembly 100 is removed.

Figure 81A:
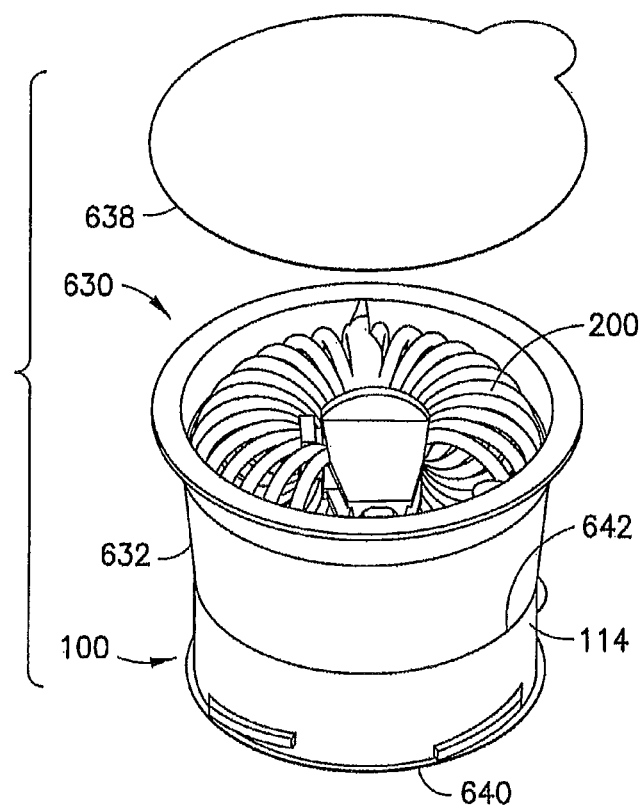
FIGS. 81A-81B are a perspective view and a cross-sectional view, respectively, of a packaging container in which the cap of the cap-bladder assembly forms an integral part of the packaging container.
Figure 81B:
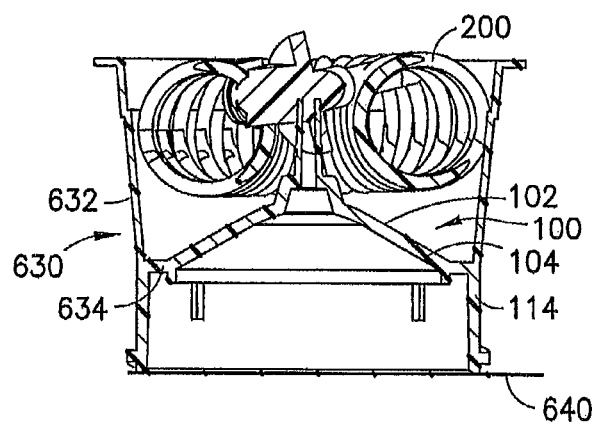

In FIGS. 81A-81B, a packaging container 630 is shown with a cup-shaped body 632 that forms an upper portion of the packaging container 630. The cup-shaped body 632 is further integrally formed with the cap body 104 of the cap 102 of the cap-bladder assembly 100. The cap body 104 comprises a short radial flange or rim 634 that connects to the cylindrical portion 114 of the cap body 104. The cylindrical portion 114 forms a lower part or portion of the packaging container 630. Thus, the cap body 104 and the cylindrical portion 114 thereof form part of the packaging container 630. The open top end of the cup-shaped body 632 is sealed by a protective seal 638, typically a sterilized seal, that is peeled away to remove the cap-bladder assembly 100. Likewise, the open end of the cap body 104 defined by the cylindrical portion 114 is sealed by a protective seal 640, typically a sterilized seal, that is peeled away to access the bladder 1140 in the cap body 104, which is not shown in FIG. 81B for simplicity. Moreover, a score line 642 or other method for detaching the cap body 104 from the cup-shaped body 632 is provided between these components. A plurality of the packaging containers 630 may be stored in end-to-end relationship in a tubular shipping container which may have a suitable end or side opening to permit individual containers 630 to be removed one at a time.

While embodiments of a bladder syringe fluid delivery system and methods of operation thereof were provided in the foregoing description, those skilled in the art may make modifications and alterations to these embodiments without departing from the scope and spirit of the invention. Accordingly, the foregoing description is intended to be illustrative rather than restrictive. The various embodiments described hereinabove are defined by the appended claims and all changes that fall within the meaning and the range of equivalency of the claims are to be embraced within their scope.

The invention claimed is:

1. A bladder syringe for a fluid delivery system, the syringe comprising:

a cylindrical body having a distal end and a proximal end and defining a throughbore;

a cap-bladder assembly adapted for connection to the distal end of the cylindrical body, the cap-bladder assembly comprising:

a cap comprising a cap body defining an interior cavity and a distal discharge conduit, the cap body seated on the distal end of the cylindrical body; and a disc-shaped bladder disposed within the interior cavity and comprising a membrane portion; and a plunger element disposed in the throughbore of the cylindrical body, the plunger element having a seal ring providing a substantially fluid tight seal between the plunger element and the cylindrical body, wherein a distal portion of the plunger element comprises a vent path having a radial passageway with an inlet at a circumferential outer surface of the plunger element distal of the seal ring and a one-way check valve allowing gas to pass through the plunger element to vent a space in the cylindrical body between the cap-bladder assembly and the plunger element during fluid delivery via distal movement of the plunger element toward the cap-bladder assembly.

2. The bladder syringe of claim 1, wherein the cap-bladder assembly further comprises a retainer ring to secure the bladder in the interior cavity of the cap body.

3. The bladder syringe of claim 1, wherein the membrane portion has extra material in a central area of the membrane portion.

4. The bladder syringe of claim 1, wherein the membrane portion defines a convoluted central well portion.

5. The bladder syringe of claim 1, wherein the membrane portion is substantially planar.

6. The bladder syringe of claim 1, wherein the membrane portion comprises a plurality of annular ribs or rings.

7. The bladder syringe of claim 1, wherein the membrane portion comprises a plurality of radial ribs.

8. The bladder syringe of claim 1, wherein the membrane portion has extra material in a central area of the membrane portion and defines a convoluted central well portion.

9. The bladder syringe of claim 1, wherein the membrane portion comprises a series of concentric angular-shaped convolutes.

10. The bladder syringe of claim 1, wherein the membrane portion has a thinner center section and a thicker outer section tapering from the thinner center section.

11. The bladder syringe of claim 1, wherein the membrane portion comprises a series of thicker wall sections near a center of the bladder.

12. The bladder syringe of claim 11, wherein the thicker wall sections are stepped.

13. The bladder syringe of claim 1, wherein the membrane portion has a non-uniform cross-section.

14. The bladder syringe of claim 1, wherein the membrane portion defines a central well portion connected to an outer rim by a series of frangible webs.

15. The bladder syringe of claim 1, wherein the membrane portion is comprised of two or more materials.

16. The bladder syringe of claim 1, wherein the membrane portion has over-molded ribs on a proximal side thereof.

17. The bladder syringe of claim 1, wherein a distal face of the plunger element faces the cap-bladder assembly and the plunger element comprises a proximal portion adapted for connection with a piston element of a power fluid injector.

18. The bladder syringe of claim 1, wherein the plunger element comprises one of an optical sensor, an ultrasonic sensor, and a mechanical sensor to detect a presence of the cap-bladder assembly on the distal end of the cylindrical body.

19. The bladder syringe of claim 1, wherein the distal portion of the plunger element and the membrane portion of the bladder are shaped to interact to maintain a bladder material aligned in the cylindrical body during expansion of the bladder.

20. The bladder syringe of claim 19, wherein the membrane portion defines a convoluted central well portion, and wherein the distal portion of the plunger element defines a distal circular recess to interact with the convoluted central well portion.

21. The bladder syringe of claim 19, wherein the membrane portion defines a series or a plurality of concentric stepped or ridged portions adapted to cooperate with corresponding concentric stepped or ridged portions on a surface of the distal portion of the plunger element.

22. The bladder syringe of claim 1, wherein the distal portion of the plunger element and the bladder interact to restrict movement of the bladder outward toward an interior wall of the cylindrical body to conserve a bladder material thickness in a center of the membrane portion as the plunger element is retracted in the cylindrical body creating vacuum pressure between the plunger element and the bladder.

23. A fluid delivery system, comprising:
a power fluid injector comprising an injector housing and a reciprocally operable piston element; and
a bladder syringe, comprising:
a cylindrical body having a distal end and a proximal end and defining a throughbore;
a cap-bladder assembly adapted for connection to the distal end of the cylindrical body, comprising:
a cap comprising a cap body defining an interior cavity and a distal discharge conduit, the cap body seated on the distal end of the cylindrical body; and
a disc-shaped bladder disposed within the interior cavity and comprising a membrane portion; and
a plunger element disposed in the throughbore of the cylindrical body and comprising a distal portion facing the cap-bladder assembly and a proximal portion adapted for connection with the piston element of the power fluid injector, the proximal portion having a seal ring providing a substantially fluid tight seal between the plunger element and the cylindrical body,
wherein the distal portion of the plunger element comprises a vent path having a radial passageway with an inlet at a circumferential outer surface of the plunger element distal of the seal ring and a one-way check valve allowing gas to pass through the plunger element to vent a space in the cylindrical body between the cap-bladder assembly and the plunger element during fluid delivery via distal movement of the plunger element toward the cap-bladder assembly.

24. The fluid delivery system of claim 23, wherein the cap-bladder assembly further comprises a retainer ring to secure the bladder in the interior cavity of the cap body.

25. The fluid delivery system of claim 23, wherein the membrane portion has extra material in a central area of the membrane portion.

26. The fluid delivery system of claim 23, wherein the membrane portion defines a convoluted central well portion.

27. The fluid delivery system of claim 23, wherein the membrane portion is substantially planar.

28. The fluid delivery system of claim 23, wherein the membrane portion comprises a plurality of annular ribs or rings.

29. The fluid delivery system of claim 23, wherein the membrane portion comprises a series of concentric angular-shaped convolutes.

30. The fluid delivery system of claim 23, wherein the membrane portion has a thinner center section and a thicker outer section tapering from the thinner center section.

31. The fluid delivery system of claim 23, wherein the membrane portion comprises a series of thicker wall sections near a center of the bladder.

32. The fluid delivery system of claim 31, wherein the thicker wall sections are stepped.

33. The fluid delivery system of claim 23, wherein the membrane portion has a non-uniform cross-section.

34. The fluid delivery system of claim 23, wherein the membrane portion defines a central well portion connected to an outer rim by a series of frangible webs.

35. The fluid delivery system of claim 23, wherein the membrane portion is comprised of two or more materials.

36. The fluid delivery system of claim 23, wherein the membrane portion has over-molded ribs on a proximal side thereof.

37. The fluid delivery system of claim 23, wherein the plunger element comprises one of an optical sensor, an ultrasonic sensor, and a mechanical sensor to detect a presence of the cap-bladder assembly on the distal end of the cylindrical body.

38. The fluid delivery system of claim 23, wherein the distal portion of the plunger element and the membrane portion of the bladder are shaped to interact to maintain a bladder material aligned in the cylindrical body during expansion of the bladder.

39. The fluid delivery system of claim 38, wherein the membrane portion defines a convoluted central well portion, and wherein the distal portion of the plunger element defines a distal circular recess to interact with the convoluted central well portion.

40. The fluid delivery system of claim 38, wherein the membrane portion defines a series or plurality of concentric stepped or ridged portions adapted to cooperate with corresponding concentric stepped or ridged portions on a surface of the distal portion of the plunger element.

41. The fluid delivery system of claim 23, wherein the distal portion of the plunger element and the bladder interact to restrict movement of the bladder outward toward an interior wall of the cylindrical body to conserve a bladder material thickness in a center of the membrane portion as the plunger element is retracted in the cylindrical body creating vacuum pressure between the plunger element and the bladder.

* * * * *

UNITED STATES PATENT AND TRADEMARK OFFICE
CERTIFICATE OF CORRECTION

PATENT NO.        : 10,046,106 B2
APPLICATION NO.   : 13/881072
DATED             : August 14, 2018
INVENTOR(S)       : Cowan et al.

Page 1 of 1

It is certified that error appears in the above-identified patent and that said Letters Patent is hereby corrected as shown below:

In the Specification

In Column 31, Line 47, delete "cylindrical portion 30." and insert -- cylindrical body 30. --, therefor.

Signed and Sealed this
Thirteenth Day of November, 2018

Andrei Iancu
*Director of the United States Patent and Trademark Office*